(12) United States Patent
Uchiyama

(10) Patent No.: US 9,658,182 B2
(45) Date of Patent: May 23, 2017

(54) METHOD FOR MEASURING CONCENTRATION OF ANALYTE IN BLOOD SAMPLE, AND BIOSENSOR SYSTEM

(71) Applicant: Panasonic Healthcare Co., Ltd., Ehime (JP)

(72) Inventor: Motonori Uchiyama, Ehime (JP)

(73) Assignee: PANASONIC HEALTHCARE HOLDINGS CO., LTD., Tokyo (JP)

( * ) Notice: Subject to any disclaimer, the term of this patent is extended or adjusted under 35 U.S.C. 154(b) by 475 days.

(21) Appl. No.: 14/230,221

(22) Filed: Mar. 31, 2014

(65) Prior Publication Data

US 2014/0209482 A1     Jul. 31, 2014

Related U.S. Application Data

(63) Continuation of application No. 13/127,585, filed as application No. PCT/JP2009/006435 on Nov. 27, 2009.

(30) Foreign Application Priority Data

Nov. 28, 2008   (JP) ................................. 2008-305694

(51) Int. Cl.
*G01N 27/327*   (2006.01)
*G01N 33/49*    (2006.01)

(52) U.S. Cl.
CPC ......... *G01N 27/3274* (2013.01); *G01N 33/49* (2013.01)

(58) Field of Classification Search
CPC ........... G01N 27/3274; G01N 27/3271; G01N 25/18; G01N 25/20; G01N 25/4806;
(Continued)

(56) References Cited

U.S. PATENT DOCUMENTS

| 5,264,103 A | 11/1993 | Yoshioka et al. |
| 6,780,296 B1 | 8/2004 | Bhullar et al. |

(Continued)

FOREIGN PATENT DOCUMENTS

| CA | 2 328 750 A1 | 6/2001 |
| CA | 2 696 661    | 6/2001 |

(Continued)

OTHER PUBLICATIONS

Chinese Office Action issued Dec. 19, 2012 in corresponding Chinese Application No. 200980144510.3.

(Continued)

*Primary Examiner* — J. Christopher Ball
(74) *Attorney, Agent, or Firm* — Wenderoth, Lind & Ponack, L.L.P.

(57) ABSTRACT

The method includes: acquiring data a related to a temperature of a blood sample on a sensor chip, based on a dimension of a current flowing in the blood sample by applying a first voltage to the pair of electrodes in contact with the blood sample, the first voltage being set so as to reduce an effect of hematocrit on a temperature measurement result; acquiring data b related to the concentration of an analyte in the blood sample, based on a dimension of a current flowing in the blood sample by applying a second voltage that is equal to or less than the first voltage, utilizing a reaction mediated by an oxidoreductase that uses the analyte in the blood sample as a substrate; and measuring a concentration that determines the analyte concentration in the blood sample based on the data a and the data b.

13 Claims, 53 Drawing Sheets

(58) Field of Classification Search
CPC .... G01N 25/4813; G01N 33/49; G01N 33/72; G01N 33/721
See application file for complete search history.

(56) References Cited

U.S. PATENT DOCUMENTS

| | | | |
|---|---|---|---|
| 7,510,643 B2 | 3/2009 | Bhullar et al. | |
| 7,638,033 B2 | 12/2009 | Kasielke et al. | |
| 7,655,456 B2 | 2/2010 | Oshiman et al. | |
| 8,721,851 B2* | 5/2014 | Uchiyama | G01N 27/3274 204/403.01 |
| 2003/0159945 A1 | 8/2003 | Miyazaki et al. | |
| 2004/0238357 A1 | 12/2004 | Bhullar et al. | |
| 2005/0019219 A1 | 1/2005 | Oshiman et al. | |
| 2005/0023137 A1 | 2/2005 | Bhullar et al. | |
| 2005/0023152 A1 | 2/2005 | Surridge et al. | |
| 2006/0108236 A1 | 5/2006 | Kasielke et al. | |
| 2007/0131565 A1 | 6/2007 | Fujiwara et al. | |
| 2009/0000947 A1 | 1/2009 | Akahori et al. | |
| 2009/0184004 A1* | 7/2009 | Chatelier | G01N 27/3274 205/777.5 |
| 2010/0270177 A1 | 10/2010 | Fujiwara et al. | |

FOREIGN PATENT DOCUMENTS

| | | |
|---|---|---|
| CA | 2 521 370 A1 | 10/2004 |
| CA | 2 529 668 | 12/2004 |
| CA | 2 328 750 C | 7/2010 |
| CA | 2 521 370 C | 7/2010 |
| CN | 1886651 | 12/2006 |
| CN | 101059503 | 10/2007 |
| EP | 0 537 761 | 4/1993 |
| EP | 1 114 994 | 7/2001 |
| EP | 1 467 201 | 10/2004 |
| EP | 1 467 206 | 10/2004 |
| EP | 1 613 955 | 4/2008 |
| EP | 1 909 097 | 4/2008 |
| GB | 2 126 350 | 3/1984 |
| JP | 59-65246 | 4/1984 |
| JP | 9-250996 | 9/1997 |
| JP | 2001-235444 | 8/2001 |
| JP | 2003-42995 | 2/2003 |
| JP | 2003-156469 | 5/2003 |
| JP | 2005-265629 | 9/2005 |
| JP | 2006-522923 | 10/2006 |
| JP | 2007-33458 | 2/2007 |
| JP | 2007-524818 | 8/2007 |
| JP | 2007-524825 | 8/2007 |
| WO | 03/062812 | 7/2003 |
| WO | 2004/090533 | 10/2004 |
| WO | 2004/113896 | 12/2004 |
| WO | 2004/113910 | 12/2004 |
| WO | 2005/012900 | 2/2005 |
| WO | 2006/132250 | 12/2006 |

OTHER PUBLICATIONS

Extended European Search Report issued May 3, 2013 in corresponding European Application No. EP 09 82 8879.8.

* cited by examiner (a)

(b)

(a)

(b)

(a)

(b)

(a)

(b)

(a)

(b)

(a)

LEAD WIDTH OF
COUNTER ELECTRODE (b)

(a)

(b)

(a)

(b)

(a)

(b)

(a)

(b)

(a)

(b)

(a)

(b)

(a)

(b)

METHOD FOR MEASURING CONCENTRATION OF ANALYTE IN BLOOD SAMPLE, AND BIOSENSOR SYSTEM

The present invention relates to a sensor chip, a biosensor system, a method for measuring temperature for a biological sample, a method for measuring temperature for a blood sample, and a method for measuring a concentration of an analyte in a blood sample.

BACKGROUND

A portable biosensor system provided with a measuring device having a calculating unit and a sensor chip detachable from the measuring device is used for measuring an analyte concentration, for example a blood glucose concentration (blood glucose value) in a blood sample. The analyte concentration is calculated by an optical method or an electrochemical method based on an amount of a reductant or an oxidant produced by an oxygen cycling reaction mediated by an oxidoreductase that uses the analyte as a substrate. The speed of the oxygen cycling reaction depends on the temperature that promotes the reaction (reaction temperature). As a result, the concentration of the analyte is preferably corrected with reference to the reaction temperature.

The reaction temperature for example is measured by a temperature sensor disposed in the measuring device (Patent Literature 1). However, in the biosensor system according to Patent Literature 1, the inner portion temperature of the measuring device is measured, and therefore the measured reaction temperature does not accurately reflect the temperature of the blood sample. As a result, an error may result in the measurement of the analyte concentration.

Patent Literature 2-4 disclose a biosensor system for improving the measurement accuracy of the reaction temperature. The biosensor system in Patent Literature 2 and 3 includes a heat conduction member in proximity to the blood sample retention unit of the sensor chip, and detects the temperature of the blood sample transmitted through the heat conduction member with a temperature sensor disposed in the measuring device. Since the biosensor system in Patent Literature 2 and 3 includes a resin plate disposed between the heat conduction member and the blood sample retention unit, the heat conduction member does not come into contact with the blood sample. The biosensor system in Patent Literature 4 includes a temperature sensor and a heat conduction member disposed in a mounting unit of the measuring device for mounting of the sensor chip, and therefore transmits the temperature of the blood sample to the temperature sensor through the heat conduction member.

CITATION LIST

Patent Literature

Patent Literature 1: Japanese Patent Application Laid-Open No. 2003-156469
Patent Literature 2: Japanese Patent Application Laid-Open No. 2001-235444
Patent Literature 3: Japanese Patent Application Laid-Open No. 2003-42995
Patent Literature 4: Pamphlet of PCT International Application No. 2003/062812

SUMMARY

When a user with a biosensor system moves into a location that has a large temperature difference (for example, moves from an external location in summer or winter into a building), the measuring device will be incapable of tracking the sharp variation in the environmental temperature, and for a certain period of time, will maintain a higher temperature or lower temperature than the environment of the current location. For example, when moving the measuring device from a 40° C. or a 10° C. environment to a 25° C. environment, a period of approximately 30 minutes may be required until the temperature of the measuring device reaches 25° C. (Patent Literature 1).

It is difficult to completely eliminate the effect of the temperature of the measuring device when measuring the reaction temperature by a temperature sensor in a measuring device. Thus when there is a sharp change in the temperature of the environment in which the sensor is used, an error will tend to be produced in the measurement of an analyte concentration when using the biosensor system disclosed in Patent Literature 2-4.

Since the temperature of the blood sample in the biosensor system disclosed in Patent Literature 2-4 is communicated by heat transfer through the resin plate and the heat conduction member to the temperature sensor, the measured reaction temperature does not accurately reflect the temperature of the blood sample.

The present invention has the object of providing a biosensor system and a sensor chip for application to the biosensor system that measures a temperature of a blood sample and suppresses the production of a measurement error resulting from the temperature of a use environment. Furthermore the present invention has the object of providing a measurement method that improves the measurement accuracy of an analyte concentration in a blood sample.

A sensor chip according to a first aspect of the present invention is a sensor chip for measuring the temperature of a biological sample and includes temperature electrodes having at least a working electrode and an counter electrode for measuring the temperature of the biological sample, and having a direct current voltage applied thereto, and a capillary configured to introduce the biological sample to the temperature electrodes. The working electrode and/or the counter electrode in the temperature electrodes are disposed to make contact with the biological sample introduced into the capillary. The direct current voltage is set to reduce an effect of hematocrit on a temperature measurement result of hematocrit during application of the direct current voltage.

In this sensor chip, a predetermined direct current voltage is applied to the temperature electrodes so that the effect of hematocrit is low during measurement of the biological sample temperature by the temperature electrodes.

In this manner, temperature measurement of a biological sample is enabled without reference to a hematocrit value in the biological sample. As a result, the temperature measurement accuracy for a biological sample can be improved, and the accuracy in relation to various types of corrections using the temperature of the biological sample can also be improved.

A sensor chip according to a second aspect of the present invention includes the sensor chip according to the first aspect, and the uptake amount of the biological sample into the capillary is 5 µL or less, and the application time of the direct current voltage to the temperature electrodes is 15 seconds or less.

A sensor chip according to a third aspect of the present invention includes the sensor chip according to the first or the second aspect, and the predetermined direct current voltage is within a range in which the solvent of the biological sample is subjected to electrolysis.

A sensor chip according to a fourth aspect of the present invention includes the sensor chip according to any one of the first to the third aspect, and is disposable.

A sensor chip according to a fifth aspect of the present invention is a sensor chip for measuring the concentration of an analyte in a blood sample, and includes temperature electrodes disposed to make contact with the blood sample, and having at least a working electrode and an counter electrode for measuring the temperature of the blood sample, and a concentration measuring unit configured to measure a feature related to a concentration of the analyte in the blood sample.

In this manner, direct measurement of the temperature of a blood sample is enabled in contrast to a conventional sensor chip provided with temperature electrodes that measure the heat transmitted through a resin plate, heat conduction member, or the like. As a result, the production of a measurement error caused by the temperature of the use environment can be suppressed, and an improvement in the measurement accuracy of the analyte concentration in a blood sample is enabled.

A sensor chip according to a sixth aspect of the present invention includes the sensor chip according to the fifth aspect, and the concentration measuring unit is formed from analysis electrodes including at least a working electrode and an counter electrode.

A sensor chip according to a seventh aspect of the present invention includes the sensor chip according to the sixth aspect, and the temperature electrodes and the analysis electrodes are provided separately.

In this manner, accurate measurement of a concentration of an analyte in a blood sample is enabled.

A sensor chip according to an eighth aspect of the present invention includes the sensor chip according to the sixth or the seventh aspect, and further includes a sample introduction port and a capillary configured to introduce a blood sample from the sample introduction port to the temperature electrodes and the analysis electrodes. The temperature electrodes are disposed at a position closer to the sample introduction port than the analysis electrodes.

A sensor chip according to a ninth aspect of the present invention includes the sensor chip according to any one of the fifth to the eighth aspect, and the temperature electrodes are disposed to not make contact with at least one of the oxidoreductase or the electron mediator.

In this manner, the temperature of the blood sample can be accurately measured.

A sensor chip according to a tenth aspect of the present invention includes the sensor chip according to any one of the fifth to the ninth aspect, and the concentration measuring unit further includes a reaction reagent that induces an oxidation-reduction reaction, and the temperature electrodes are disposed to not make contact with the reaction reagent that induces the oxidation-reduction reaction.

In this manner, contact of the reaction reagent with the temperature electrodes can be avoided, and accurate measurement of the blood sample temperature is enabled.

A sensor chip according to an eleventh aspect of the present invention includes the sensor chip according to any one of the fifth to the ninth aspect, and is disposed to not make contact with any reagent.

In this manner, contact of any reagent with the temperature electrodes can be avoided, and accurate measurement of the blood sample temperature is enabled.

A sensor chip according to a twelfth aspect of the present invention includes the sensor chip according to the sixth aspect, and the working electrode of the temperature electrodes is common to at least either the working electrode or the counter electrode of the analysis electrodes.

A sensor chip according to a thirteenth aspect of the present invention includes the sensor chip according to the sixth aspect, and the counter electrode of the temperature electrodes is common to at least either the working electrode or the counter electrode of the analysis electrodes.

A sensor chip according to a fourteenth aspect of the present invention includes the sensor chip according to any one of the sixth to the eighth aspect, and the concentration measuring unit includes at least one electrode in addition to the working electrode and the counter electrode, and at least one of the electrodes of the concentration measuring unit other than the working electrode and the counter electrode is common to at least one of the working electrode and the counter electrode of the temperature electrodes.

The electrodes included in the concentration measuring unit according to the twelfth to the fourteenth aspects may be combined with at least one of the working electrode and the counter electrode of the temperature electrodes.

The sensor chip according to the twelfth and the thirteenth aspects may include a plurality of working electrodes and/or a plurality of counter electrodes as analysis electrodes. At least one of the plurality of working electrodes and/or counter electrodes may be combined with the working electrode and/or counter electrode of the temperature electrodes.

An example of an electrode other than a working electrode and counter electrode according to the fourteenth aspect includes
- a hematocrit measuring electrode;
- a measuring electrode for an amount or concentration of a reducing substance;
- a detection electrode for detecting the introduction of blood; and
- a measuring electrode other than a electrode for measuring an amount or concentration of a reducing substance, hematocrit, or glucose concentration.

A sensor chip according to a fifteenth aspect of the present invention includes the sensor chip according to the sixth aspect, and the surface area of the working electrode in the temperature electrodes is either the same or smaller than the surface area of the counter electrode in the temperature electrodes.

A sensor chip according to a sixteenth aspect of the present invention includes the sensor chip according to any one of the fifth to the fifteenth aspect, and at least hematocrit is included as a feature in relation to the concentration of the analyte.

A sensor chip according to a seventeenth aspect of the present invention includes the sensor chip according to any one of the fifth to the sixteenth aspect, and at least a concentration or an amount of a reducing substance is included as a feature in relation to the concentration of the analyte.

A method for measuring a temperature of a biological sample according to an eighteenth aspect of the present invention measures a temperature of a biological sample by a sensor chip including temperature electrodes formed from a working electrode and an counter electrode, and a capillary. The method includes an introduction step of introducing a biological sample by the capillary to the temperature electrodes, an application step of applying a direct current voltage to the temperature electrodes, and an adjustment step of adjusting the direct current voltage applied in the application step to a first voltage. The first voltage is set so that the effect of hematocrit on the temperature measurement result during application of the first voltage to the temperature electrodes is reduced.

This method enables temperature measurement of a biological sample without reference to a hematocrit value in the biological sample. As a result, the accuracy of the temperature measurement of the biological sample can be increased, and the accuracy in relation to various corrections using the temperature of the biological sample can also be increased.

A method for measuring a temperature according to a nineteenth aspect of the present invention includes the method for measuring a temperature according to the eighteenth aspect, and a direct current voltage that enables a reduction of the effect of hematocrit on the temperature measurement result is measured and stored in advance, and the adjustment step adjusts to the first voltage based on the stored direct current voltage.

A method for measuring a temperature of a biological sample according to a twentieth aspect of the present invention includes the method for temperature measurement of a biological sample according to the eighteenth or the nineteenth aspect, and the uptake amount of the biological sample in the introduction step is 5 µL or less, and the application time of the direct current voltage in the application step is 15 seconds or less.

A method for measuring a temperature of a blood sample according to a twenty first aspect of the present invention measures a temperature of a blood sample using a sensor chip including temperature electrodes formed from a working electrode and an counter electrode. The method includes a step of applying a voltage to the temperature electrodes in contact with the blood sample, a step of acquiring data a related to the temperature of the blood sample based on a dimension of a current flowing in the blood sample by application of the voltage, and a step of calculating a temperature t of the blood sample based on the data a.

A temperature t of the blood sample is calculated based on data a related to the temperature of the blood sample that can be acquired by application of a voltage to the temperature electrodes in contact with the blood sample.

In this manner, since the temperature t of the blood sample can be calculated based on data a related to the temperature of the blood sample that can be accurately acquired, the production of a measurement error caused by the temperature of the use environment can be suppressed.

A method for measuring a concentration of an analyte in a blood sample according to a twenty second aspect of the present invention includes a step of acquiring data a related to the temperature of the blood sample based on the dimension of a current flowing in the blood sample by application of a voltage to the pair of electrodes in contact with the blood sample, a step of acquiring data b related to a concentration of the analyte based on the dimension of a current flowing in the blood sample by a reaction mediated by an oxidoreductase that uses the analyte in the blood sample as a substrate, and a step of measuring a concentration that determines the analyte concentration in the blood sample based on the data a and the data b.

Herein, the data a is acquired by directly measurement of the temperature of the blood sample without interposing a resin plate or a heat conduction member, and the analyte concentration in the blood sample is determined based on the data a related to the temperature of the blood sample and the data b related to the concentration of the analyte.

In this manner, the measurement accuracy of the analyte concentration in the blood sample can be improved.

A method for measuring a concentration of an analyte in a blood sample according to a twenty third aspect of the present invention includes the method for measuring a concentration of an analyte in a blood sample according to the twenty second aspect, and the concentration measurement step includes a step of correcting the data b based on the data a.

In this manner, the measurement accuracy of the concentration of the analyte in the blood sample can be improved.

A method for measuring a concentration of an analyte in a blood sample according to a twenty fourth aspect of the present invention includes the method for measuring a concentration of an analyte in a blood sample according to the twenty second aspect, and the concentration measurement step includes a step of calculating a concentration x of an analyte in a blood sample based on the data b, and a step of correcting the concentration x based on the data a.

In this manner, the measurement accuracy of the concentration of the analyte in the blood sample can be improved.

A method for measuring a concentration of an analyte in a blood sample according to a twenty fifth aspect of the present invention includes the method for measuring a concentration of an analyte in a blood sample according to the twenty second aspect, and the concentration measurement step includes a step of calculating a temperature t of the analyte in the blood sample based on the data a, and a step of correcting the data b based on the temperature t.

In this manner, the measurement accuracy of the concentration of the analyte in the blood sample can be improved.

A method for measuring a concentration of an analyte in a blood sample according to a twenty sixth aspect of the present invention includes the method for measuring a concentration of an analyte in a blood sample according to the twenty second aspect, and the concentration measurement step includes a step of calculating a temperature t of an analyte in a blood sample based on the data a, a step of calculating a concentration x of the analyte in a blood sample based on the data b, and a step of correcting the concentration x based on the temperature t.

In this manner, the measurement accuracy of the concentration of the analyte in the blood sample can be improved.

A method for measuring a concentration of an analyte in a blood sample according to a twenty seventh aspect of the present invention includes the method for measuring a concentration of an analyte in a blood sample according to any one of the twenty second to the twenty sixth aspect, and the step of acquiring the data a is performed in advance of the step of acquiring the data b.

In this manner, the temperature at the time of acquiring the data b can be more accurately reflected.

A method for measuring a concentration of an analyte in a blood sample according to a twenty eighth aspect of the present invention includes the method for measuring a concentration of an analyte in a blood sample according to the twenty second aspect, and the concentration measurement step includes a step of acquiring data c related to the temperature of the blood sample based on the dimension of a current flowing in the blood sample by application of a predetermined voltage to the pair of electrodes in contact with the blood sample after acquisition of the data b, and a step of calculating data d related to the temperature of the blood sample based on the data a and the data c, and a step of correcting the data b based on the data d.

In this manner, the temperature at the time of acquiring the data b can be more accurately reflected, and the analyte concentration measurement accuracy for the blood sample can be improved.

A method for measuring a concentration of an analyte in a blood sample according to a twenty ninth aspect of the present invention includes the method for measuring a concentration of an analyte in a blood sample according to the twenty second aspect, and the concentration measurement step includes a step of calculating the temperature t of the blood sample based on the data a, a step of calculating the concentration x of the analyte in the blood sample based on the data b, the step of measuring an environmental temperature t1 on a periphery of the blood sample, a step of comparing the difference between the temperature t and the environmental temperature t1 with a temperature threshold Z, and a step of correcting the concentration x based on the temperature t when the relation |t−t1|≥Z is satisfied, and correcting the concentration x based on the temperature t1 when the relation |t−t1|<Z is satisfied.

Herein, the concentration x of the analyte in the blood sample is calculated based on the data b, and the temperature t of the blood sample is calculated based on the data a. The environmental temperature t1 in the periphery of the blood sample is measured. Then the difference between the temperature t and the environmental temperature t1 is compared with a temperature threshold Z, and correction is performed as described below.

When |t−t1|≥Z is satisfied, the concentration x is corrected based on the temperature t When |t−t1|<Z is satisfied, the concentration x is corrected based on the temperature t1

In this manner, since the concentration x can be corrected using an appropriate temperature in response to an external temperature environment, a measurement accuracy for the analyte concentration in the blood sample can be improved.

A method for measuring a concentration of an analyte in a blood sample according to a thirtieth aspect of the present invention includes the method for measuring a concentration of an analyte in a blood sample according to any one of the twenty second aspect to the twenty ninth aspect, and a temperature is contained in the data a related to the temperature of the blood sample, and a glucose concentration is contained in the data b related to the concentration of the analyte.

Herein, the temperature is included as a feature of the data acquired as data a, and the glucose concentration is included as a feature of the data acquired as the data b.

A method for measuring a concentration of an analyte in a blood sample according to a thirty first aspect of the present invention includes the method for measuring a concentration of an analyte in a blood sample according to the thirtieth aspect, and hematocrit is included in the data b related to the concentration of the analyte.

Herein, hematocrit is included as a feature of the data acquired as the data b.

A method for measuring a concentration of an analyte in a blood sample according to a thirty second aspect of the present invention includes the method for measuring a concentration of an analyte in a blood sample according to the thirtieth or thirty first aspect, and the concentration or amount of the reducing substance is contained in the data b related to the concentration of the analyte.

Herein, the amount or concentration of the reducing substance is included as a feature of the data acquired as the data b.

A method for measuring a concentration of an analyte in a blood sample according to a thirty third aspect of the present invention includes the method for measuring a concentration of an analyte in a blood sample according to any one of the thirtieth to the thirty second aspect, and at least two features of the data included in the data a and the data b are measured at the same time.

Herein, when the data a and the data b are measured, at least two features of the data are measured at the same time. For example, the concentration or the amount of the reducing substance and the glucose concentration are measured at the same time.

A method for measuring a concentration of an analyte in a blood sample according to a thirty fourth aspect of the present invention includes the method for measuring a concentration of an analyte in a blood sample according to any one of the thirtieth to the thirty second aspect, and independent measurement of the respective data included in the data a and the data b is executed.

Herein, when the data a and the data b are measured, two or more features are not measured at the same time, but are measured separately. The order of measuring the features may be arbitrary.

A method for measuring a concentration of an analyte in a blood sample according to a thirty fifth aspect of the present invention includes the method for measuring a concentration of an analyte in a blood sample according to any one of the thirtieth to the thirty second aspect, and the measurement of the data contained in the data a and the data b is performed in order of temperature, glucose concentration, concentration or amount of the reducing substance, and hematocrit.

Herein, the order of measuring the data is specified. In this manner, effective results can be obtained with respect to speed, accuracy, and burden on the electrodes.

A method for measuring a concentration of an analyte in a blood sample according to a thirty sixth aspect of the present invention includes the method for measuring a concentration of an analyte in a blood sample according to any one of the thirtieth to the thirty fifth aspect, and the measurement of the data contained in the data a and the data b is performed through independent electrodes.

Herein, when measuring the data contained in the data a and the data b, such measurement is performed by respectively independent electrodes.

A biosensor system according to a thirty seventh aspect of the present invention has the sensor chip according to any one of the first to the seventeenth aspects, and a measuring device including a control circuit applying a voltage to the temperature electrodes of the sensor chip. The biosensor system measures a concentration of an analyte in a blood sample. The biosensor system includes a voltage application unit configured to apply a voltage to the temperature electrodes in accordance with the control circuit, a temperature measuring unit configured to acquire the data a related to the temperature of the blood sample based on the dimension of a current flowing in the temperature electrodes in contact with the blood sample, an analyte measuring unit acquiring data b related to the concentration of the analyte based on the dimension of a current flowing in the blood sample depending on a reaction mediated by an oxidoreductase that uses the analyte in the blood sample as a substrate, and a concentration determination unit configured to determine an analyte concentration in the blood sample based on the data a and the data b.

Herein, data a is acquired by direct measurement of the temperature of the blood sample and not through a resin plate or a heat conduction member. The concentration determination unit determines the analyte concentration in the blood sample based on the data a related to the temperature of the blood sample and the data b related to the analyte concentration.

In this manner, the production of a measurement error resulting from the temperature of the use environment can be suppressed, and thereby the measurement accuracy of the analyte concentration in the blood sample can be improved.

A biosensor system according to the thirty eighth aspect of the present invention includes the biosensor system according to the thirty seventh aspect, and the concentration determination unit includes a first analyte correction unit configured to correct the data b based on the data a.

Herein, the first analyte correction unit corrects the data b related to the concentration of the analyte in the blood sample based on the data a acquired by direct measurement of the temperature of the blood sample and not through a resin plate or a heat conduction member.

In this manner, the production of a measurement error resulting from the temperature of the use environment can be suppressed, and thereby the measurement accuracy of the analyte concentration in the blood sample can be improved.

A biosensor system according to the thirty ninth aspect of the present invention includes the biosensor system according to the thirty seventh aspect, and the concentration determination unit includes a calculating unit configured to calculate the concentration x of the analyte of the blood sample based on the data b, and a second analyte correction unit configured to correct the concentration x based on the data a.

Herein, the analyte correction unit calculates the concentration x of the analyte in the blood sample based on the data b, and then the second analyte correction unit corrects the concentration x based on the data a acquired by direct measurement of the temperature of the blood sample.

In this manner, the production of a measurement error resulting from the temperature of the use environment can be suppressed, and thereby the measurement accuracy of the analyte concentration in the blood sample can be improved.

A biosensor system according to the fortieth aspect of the present invention includes the biosensor system according to the thirty seventh aspect, and the concentration determination unit includes a calculating unit configured to calculate the temperature t of the blood sample based on the data a, and a third analyte correction unit configured to correct the data b based on the temperature t.

Herein, the calculating unit calculates the temperature t of the blood sample based on the data a acquired by direct measurement of the temperature of the blood sample, and then the third analyte correction unit corrects the data b based on the temperature t.

In this manner, the production of a measurement error resulting from the temperature of the use environment can be suppressed, and thereby the measurement accuracy of the analyte concentration in the blood sample can be improved.

A biosensor system according to the forty first aspect of the present invention includes the biosensor system according to the thirty seventh aspect, and the concentration determination unit includes a calculating unit configured to calculate the temperature t of the blood sample based on the data a, a calculating unit configured to calculate the concentration x of the blood sample based on the data b, and a fourth analyte correction unit configured to correct the concentration x based on the temperature t.

Herein, the calculating unit calculates the temperature t of the blood sample based on the data a acquired by direct measurement of the temperature of the blood sample, and calculates the concentration x of the analyte in the blood sample based on the data b, and then the fourth analyte correction unit corrects the concentration x based on the temperature t.

In this manner, the production of a measurement error resulting from the temperature of the use environment can be suppressed, and thereby the measurement accuracy of the analyte concentration in the blood sample can be improved.

A biosensor system according to the forty second aspect of the present invention includes the biosensor system according to any one of the thirty seventh aspect to the forty first aspect, and after acquisition of the data a related to the temperature of the sample by the temperature measuring unit, the data b related to the concentration of the analyte is acquired by the analyte measuring unit.

In this manner, the temperature when acquiring the data b can be more accurately reflected.

A biosensor system according to a forty third aspect of the present invention includes the biosensor system according to the thirty seventh aspect, and the concentration determination unit includes a temperature measuring unit configured to acquire data c related to the temperature of the blood sample based on the dimension of a current flowing in the blood sample by application of a predetermined voltage to the pair of electrodes in contact with the blood sample after acquisition of the data b, a computing unit configured to calculate data d related to the temperature of the blood sample based on data a and the data c, and a calculating unit configured to calculate the concentration x of the analyte corrected in response to the temperature of the blood sample based on the data d.

In this manner, after acquiring the data b, data c related to the temperature of the blood sample is acquired by the same acquisition method as the data a, and the computing unit calculates the data d related to the temperature of the blood sample based on the data a and the data c. Then the calculating unit corrects the concentration x based on the data d.

In this manner, the temperature at the time of acquisition of the data b can be more accurately reflected, and the measurement accuracy of the analyte concentration in the blood sample can be improved.

A biosensor system according to a forty fourth aspect of the present invention includes the biosensor system according to the thirty seventh aspect, and the concentration determination unit includes a temperature calculating unit configured to calculate the temperature t of the blood sample based on the data a, a concentration calculating unit configured to calculate the concentration x of the analyte in the blood sample based on the data b, an environmental temperature measuring unit configured to measure an environmental temperature t1 in a periphery of the blood sample, a comparison unit configured to compare the difference between the temperature t and the environmental temperature t1 with a temperature threshold Z, and a correction unit configured to correct the concentration x based on the temperature t when the relation $|t-t1| \geq Z$ is satisfied, and correcting the concentration x based on the temperature t1 when the relation $|t-t1| < Z$ is satisfied.

Herein, the concentration x of the analyte in the blood sample is calculated based on the data b, and the temperature of the blood sample is calculated based on the data a. The environmental temperature t1 in the periphery of the blood sample is measured. Then the difference between the temperature t and the environmental temperature t1 is compared with a temperature threshold Z, and correction is performed as described below.

When $|t-t1| \geq Z$ is satisfied, the concentration x is corrected based on the temperature t When $|t-t1| < Z$ is satisfied, the concentration x is corrected based on the temperature t1

In this manner, since the concentration x can be corrected using an appropriate temperature in response to an external temperature environment, a measurement accuracy for the analyte concentration in the blood sample can be improved.

A biosensor system according to a forty fifth aspect of the present invention includes the biosensor system according to the any one of the thirty seventh aspect to the forty fourth aspect, and a temperature is contained in the data a related to the temperature of the blood sample, and a glucose concentration is contained in the data b related to the concentration of the analyte.

Herein, the temperature is included as a feature of the data acquired as data a, and the glucose concentration is included as a feature of the data acquired as the data b.

A biosensor system according to a forty sixth aspect of the present invention includes the biosensor system according to the forty fifth aspect, and hematocrit is included in the data b related to the analyte concentration.

Herein, hematocrit is included as a feature of the data acquired as the data b.

A biosensor system according to a forty seventh aspect of the present invention includes the biosensor system according to the forty fifth aspect or forty sixth aspect, and the concentration or amount of the reducing substance is contained in the data b related to the concentration of the analyte.

Herein, the amount or concentration of the reducing substance is included as a feature of the data acquired as the data b.

A biosensor system according to a forty eighth aspect of the present invention includes the biosensor system according to the any one of the forty fifth to the forty seventh aspect, and further includes a sequence control unit configured to control the control circuit so that at least two features of the data included in the data a and the data b are measured at the same time.

Herein, when the data a and the data b are measured, the sequence control unit controls the control circuit so that at least two features of the data are measured at the same time. For example, the sequence control unit controls the control circuit so that the concentration or the amount of the reducing substance and the glucose concentration are measured at the same time.

A biosensor system according to a forty ninth aspect of the present invention includes the biosensor system according to the any one of the forty fifth to the forty seventh aspect, and further includes a sequence control unit configured to control the control circuit so that independent measurement of the respective data included in the data a and the data b is executed.

Herein, when the data a and the data b are measured, the sequence control unit controls the control circuit so that two or more features of the data are not measured at the same time, but are measured separately. The order of measuring the features may be arbitrary.

A biosensor system according to a fiftieth aspect of the present invention includes the biosensor system according to the any one of the forty fifth to the forty seventh aspect, and further includes a sequence control unit configured to control the control circuit so that the measurement of the data contained in the data a and the data b is performed in order of temperature, glucose concentration, concentration or amount of the reducing substance, or hematocrit.

Herein, the order of measuring the data is specified. In this manner, effective results can be obtained with respect to speed, accuracy, and burden on the electrodes.

A biosensor system according to a fifty first aspect of the present invention includes the biosensor system according to the any one of the forty fifth to the fiftieth aspect, and further includes an electrode selection unit configured to control the control circuit so that the measurement of the data contained in the data a and the data b is performed through independent electrodes.

Herein, when measuring the data contained in the data a and the data b, the electrode selection unit controls the control circuit so that such measurement is performed by respectively independent electrodes.

According to the sensor chip, the biosensor system, the method for measuring a temperature of a blood sample, and a method for measuring a concentration of an analyte in a blood sample according to the present invention, the production of a measurement error resulting from the temperature of a use environment is suppressed, and improvement of the measurement accuracy of an analyte concentration in a blood sample is enabled.

BRIEF DESCRIPTION OF DRAWINGS

FIG. 45(b) is a graph illustrating a response current value by temperature when temperature is measured in Working Example 21.

DETAILED DESCRIPTION

The biosensor system according to the present invention acquires the temperature of the analyte from the blood sample by a measuring unit disposed in the sensor chip.

Figure 1:
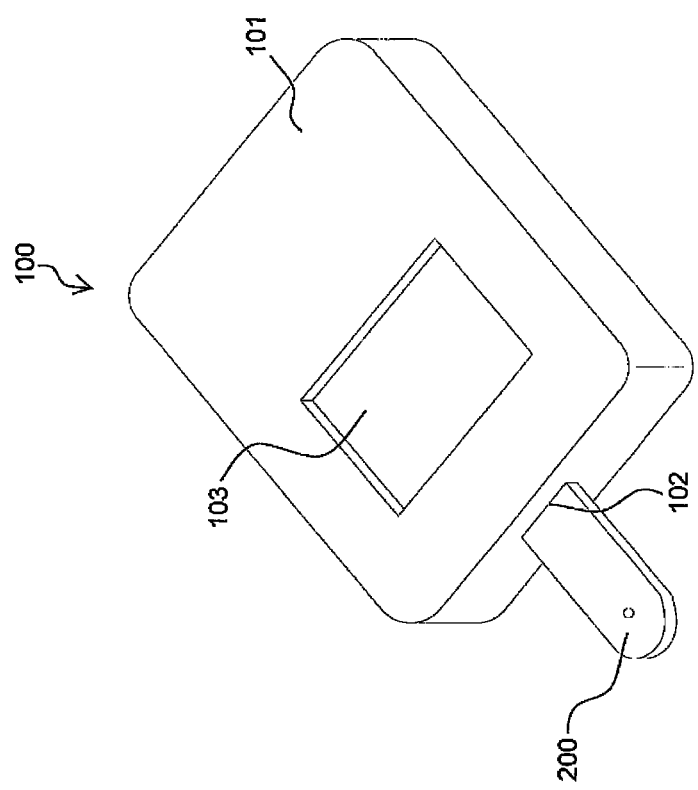
FIG. 1 is a perspective view of a biosensor system according to a first embodiment of the present invention.

FIG. 1 illustrates an example of a biosensor system according to the present invention. The biosensor system 100 includes a rectangular parallelepiped measuring device 101 and a sensor chip 200. A mounting port 102 configured as a rectangular hole is formed in a side wall surface of the measuring device 101. The sensor chip 200 is connected to the measuring device 101 that is detachably attached to the mounting port 102. The display unit 103 that displays the measurement results is disposed in a substantially central portion of one major surface of the measuring device 101.

Figure 2:
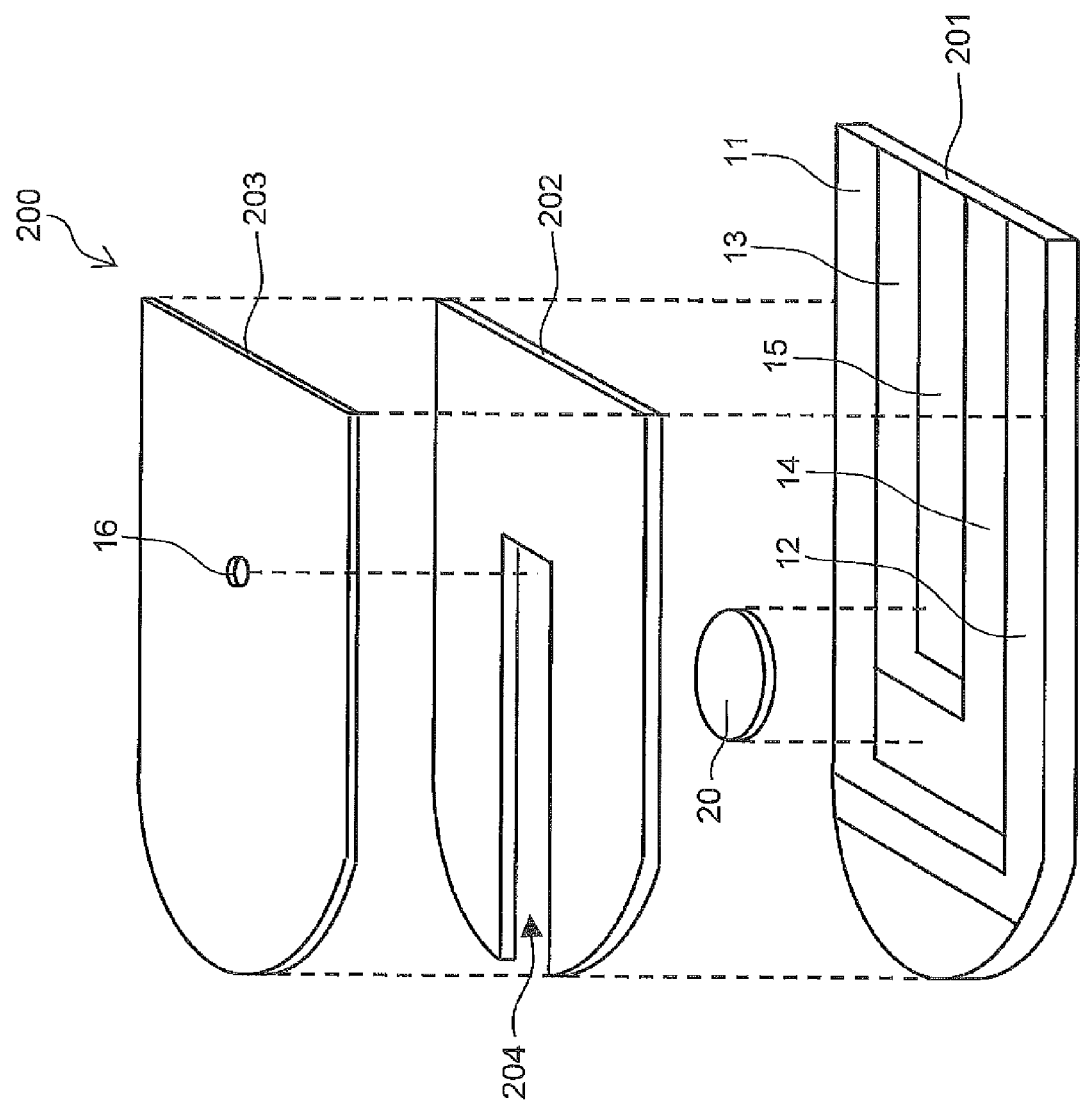
FIG. 2 is a partial perspective view of a biosensor chip according to the first embodiment of the present invention.
Figure 3:
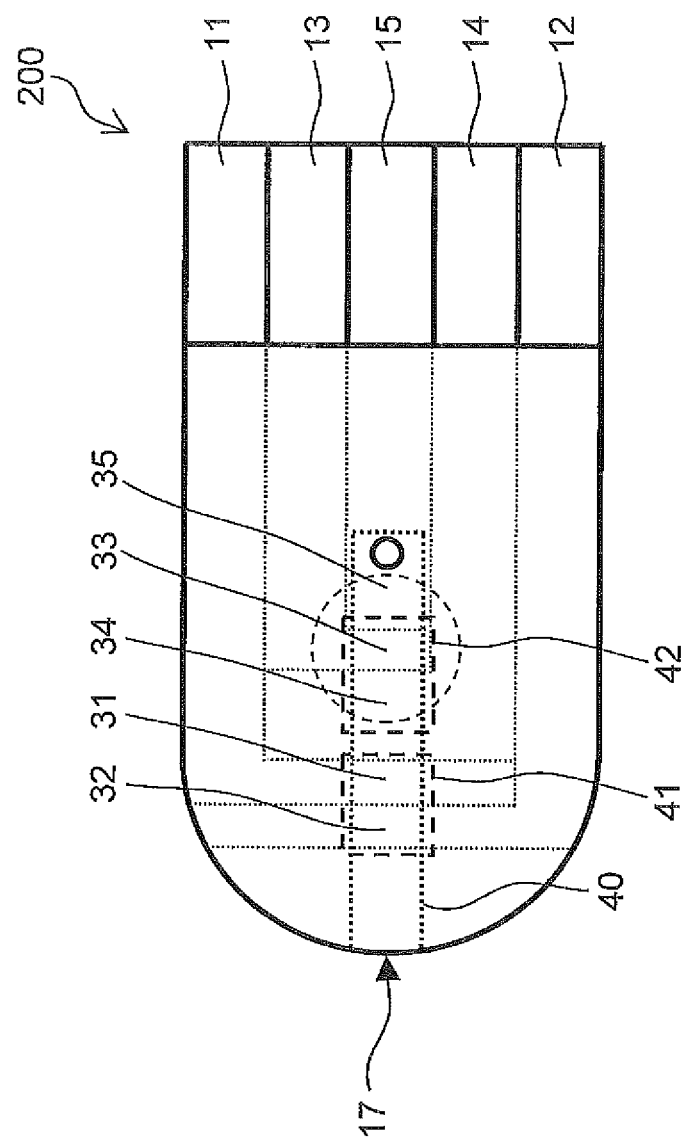
FIG. 3 is a through-view plan view of a biosensor chip according to the first embodiment of the present invention.

FIG. 2 is a partial perspective view of the sensor chip 200. FIG. 3 is a plan view thereof. In the sensor chip 200, a cover 203 is disposed on an insulating plate 201 through a spacer 202 that forms a rectangular notch 204, and leaves one end portion of the insulating plate 201 (the right end in FIG. 2).

Each member 201, 202, 203 is integrated for example by adhesion or thermal welding. After integration of each of the members, the notch 204 of the spacer 202 functions as a capillary 40 that retains the blood sample. The capillary 40 has an elongated shape along the long side of the sensor chip 200, and communicates with an outer portion on one end portion of the spacer 202 (the left end portion in FIG. 2 and FIG. 3). In other words, the capillary 40 communicates with the blood sample introduction port 17 that opens onto an outer portion of the sensor chip 200. The cover 203 includes a discharge port 16 in proximity to the opposite end to the side near the blood sample introduction port 17 in the capillary 40. In this manner, the blood sample is easily aspirated by capillary action from the blood sample introduction port 17 into an inner portion of the capillary 40.

Respective portions (portions 31, 32, 33, 34, 35) of the electrodes (voltage application portion) 11, 12, 13, 14, 15 are disposed on an insulating plate 201 to face the capillary 40. The portion 31 of the electrode 11 and the portion 32 of the electrode 12 are disposed at a position in closer proximity to the blood sample introduction port 17 than the portion 33 of the electrode 13 and the portion 34 of the electrode 14.

A reaction reagent layer 20 is formed on the insulating plate 201 to cover the whole of the portion 33 of the electrode 13 and to partially cover the portion 34 of the electrode 14 and the portion 35 of the electrode 15. The reaction reagent layer 20 includes an oxidoreductase that uses the analyte in the blood sample as a substrate, and an electron mediator.

The reaction reagent layer 20 is formed at a position separated from the portion 31 of the electrode 11 and the portion 32 of the electrode 12. It is preferred that a reagent including an oxidoreductase or an electron mediator is not disposed on the portion 31 of the electrode 11 and the portion 32 of the electrode 12, and more preferably no reagent is disposed.

In an opposite configuration to the above, when the portion 33 of the electrode 13 and the portion 34 of the electrode 14 are disposed at a position in closer proximity to the blood sample introduction port 17 than the portion 31 of the electrode 11 and the portion 32 of the electrode 12, if the blood sample is introduced from the blood sample introduction port 17, the sample may reach the portion 33 of the electrode 13 and the portion 34 of the electrode 14 due to flow in the reaction reagent layer 20 on the portion 33 of the electrode 13 and the portion 34 of the electrode 14. Therefore, this configuration should be avoided.

The sensor chip 200 includes a measuring unit 41 (measuring unit A). The measuring unit A is configured from an electrode system (temperature electrodes) formed by the portion 31 of the electrode 11 and the portion 32 of the electrode 12, and a space in a portion of the capillary 40 that contains the portion 31 and the portion 32.

The sensor chip 200 includes a measuring unit 42 (measuring unit B). The measuring unit B is configured from an electrode system (analysis electrodes) formed by the portion 33 of the electrode 13 and the portion 34 of the electrode 14, and a space in a portion of the capillary 40 that contains the reaction reagent layer 20 in addition to the portion 33 and the portion 34.

In the temperature electrodes of the measuring unit A, the electrode 11 functions as a working electrode and the electrode 12 functions as an counter electrode. In the analysis electrodes of the measuring unit B, the electrode 13 functions as a working electrode and the electrode 14 functions as an counter electrode.

The measuring unit A (temperature measuring unit) acquires the data a related to the temperature of the blood sample based on the amount of current flowing in the temperature electrodes. The substance that exhibits an electrochemical reaction on the temperature electrodes is mainly a component of the blood sample, or may be water, or may be a blood-cell component such as red blood cells or white blood cells.

The measuring unit B (analyte measuring unit) acquires the data b related to the concentration of the analyte in the blood sample based on the amount of current flowing in the analysis electrodes. The substance that exhibits an electrochemical reaction on the analysis electrodes is mainly an electron mediator that exchanges electrons with the oxidoreductase. The data b acquired in the measuring unit B is corrected based on the temperature using the data a. The concentration of the analyte is calculated using the data b after correction.

One or both of the portion 33 of the electrode 13 and the portion 34 of the electrode 14 may function as one or both of the portion 31 of the electrode 11 and a portion 32 of the electrode 12. However it is preferred that these electrodes are provided separately.

The portion 35 of the electrode 15 is disposed in proximity to the inner end portion of the capillary 40, that is to say, in proximity to the opposite end to the end that communicates with the outer portion. Application of voltage between the electrode 15 and the electrode 13 facilitates detection when the blood sample is introduced to an inner portion of the capillary 40. The voltage may be applied between the electrode 14 and the electrode 15 in substitution for the electrode 13.

The electrodes 11, 12, 13, 14, 15 are connected with respective leads (not illustrated). One end of the lead is exposed to an outer portion of the sensor chip 200 on the end portion of the insulating plate 201 that is not covered by the spacer 202 and the cover 203 to thereby enable application of a voltage between each electrode.

The analyte in the blood sample may be a substance other than a blood cell, and for example includes glucose, albumin, lactic acid, bilirubin, and cholesterol. The oxidoreductase may be a substance that uses the target analyte as a substrate. The oxidoreductase may be exemplified by glucose oxidase, glucose dehydrogenase, lactate oxidase, lactate dehydrogenase, bilirubin oxidase, and cholesterol oxidase. The amount of the oxidoreductase in the reaction reagent layer is 0.01-100 units (U), preferably 0.05-10 U, and more preferably 0.1-5 U.

The reaction reagent layer 20 preferably contains an electron mediator that has a function of exchanging electrons produced by an oxidation reaction with an electrode, such as potassium ferricyanide, p-benzoquinone, p-benzoquinone derivatives, oxidized phenazine methosulfate, methylene blue, ferricinium and ferricinium derivatives. The reaction reagent layer 20 may include a water soluble polymer compound to increase molding characteristics of the reaction reagent layer. The water soluble polymer compound may be exemplified from at least one selected from the group consisting of carboxymethyl cellulose and salts thereof, hydroxyethyl cellulose, hydroxypropylcellulose, methylcellulose, ethylcellulose, ethylhydroxyethyl cellulose, carboxymethyl cellulose and salts thereof, polyvinylalcohol, polyvinylpyrrolidone, polyamino acids such as polylysine, polystyrenesulfonic acid and salts thereof, gelatin and derivatives thereof, polyacrylic acid and salts thereof, polymethacrylate and salts thereof, starch and derivatives thereof, maleic anhydride polymers and salts thereof, and agarose gel and derivatives thereof.

The material of the insulating plate 201, the spacer 202 and the cover 203 is exemplified by polyethylene terephthalate, polycarbonate, polyimide, polyethylene, polypropylene, polystyrene, polyvinyl chloride, polyoxymethylene, monomer-cast nylon, polybutylene terephthalate, resins such as methacrylate resin and ABS resin, and glass.

The electrodes 11, 12, 13, 14, and 15 for example are configured from a known conductive material such as palladium, platinum, gold, silver, titanium, copper, nickel, and carbon.

Figure 4:
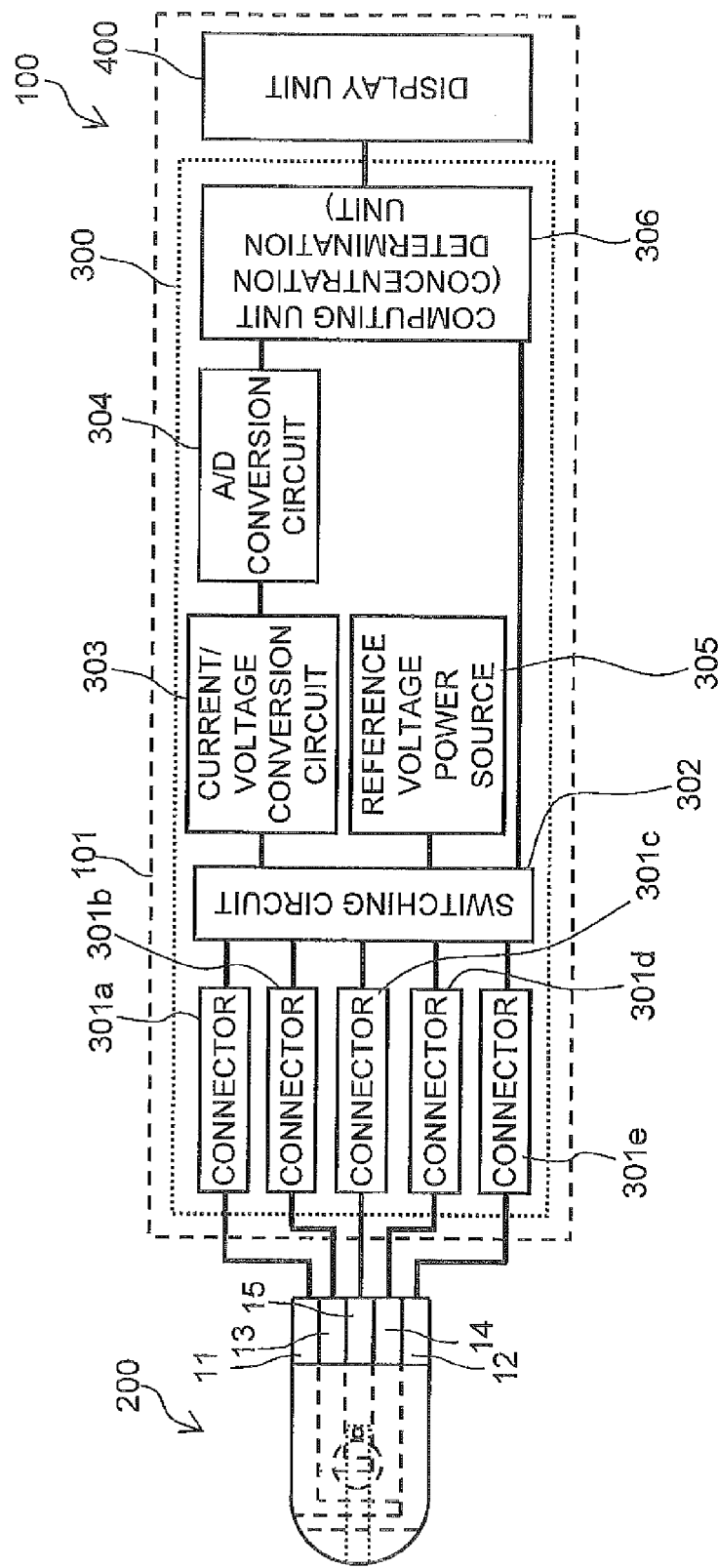
FIG. 4 is a circuit diagram in a biosensor system according to the first embodiment of the present invention.

FIG. 4 illustrates an example of a circuit configuration for measuring an analyte concentration in a blood sample in the biosensor system 100. The measuring device 101 includes a control circuit 300 that applies a voltage between at least two electrodes of the electrodes 11, 12, 13, 14 and 15 in the sensor chip 200, and a display unit 400 that displays the measurement result.

The control circuit 300 includes five connectors 301*a*, 301*b*, 301*c*, 301*d*, 301*e*, a switching circuit 302, a current/voltage conversion circuit 303, an analog/digital (A/D) conversion circuit 304, a reference voltage power source 305, and a computing unit 306. The control circuit 300 enables switching of the potential applied to the electrodes to enable use of one electrode as a cathode or as an anode through the switching circuit 302.

The computing unit (concentration determination unit) 306 includes a known central processing unit (CPU) and a conversion table for determining an analyte concentration in a blood sample based on the data a and the data b. The computing unit 306 uses a correction coefficient based on the environmental temperature to correct the analyte concentration by reference to the conversion table above. More specifically, after referring to the conversion table for preliminary measurement and provisionally calculating the analyte concentration, the computing unit 306 corrects the analyte concentration by reference to a conversion table for temperature correction.

Figure 5:
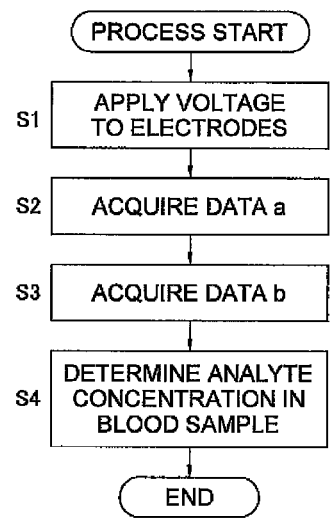
FIG. 5 is a flowchart illustrating a method for measuring an analyte concentration in a blood sample in the biosensor system according to the first embodiment of the present invention.

As illustrated in FIG. 5, the measurement of the analyte concentration in the blood sample using the biosensor system 100 for example is executed as described below.

Firstly, the CPU in the computing unit 306 commands the electrode 13 to connect with the current/voltage conversion circuit 303 through the connector 301*b* and the electrode 15 to connect with the reference voltage power source 305 through the connector 301*c*.

Thereafter, the CPU commands the application of a predetermined voltage to both electrodes (step S1). For example, when the voltage is denoted by the electrode 15 as the positive electrode and the electrode 13 as the negative electrode, the voltage is 0.01-2.0V, preferably 0.1-1.0V, and more preferably 0.2-0.5V. The voltage is applied from insertion of the sensor chip into the measuring device 101 until the introduction of the blood sample into an inner portion of the capillary 40. When the blood sample is introduced into the capillary 40 from the blood sample introduction port of the sensor chip 200, a current flows between the electrode 15 and the electrode 13. The CPU detects that the capillary 40 is filled with the blood sample by discrimination of an increase amount in the current per unit time during this period. The current value is converted to a voltage value by the current/voltage conversion circuit 303 and then is converted to a digital value by the A/D conversion circuit 304 and input to the CPU. The CPU detects that the blood sample is introduced into the inner portion of the capillary based on the digital value.

After introduction of the blood sample, for example, the analyte in the blood sample and oxygen, and oxygen and the electron mediator are reacted within a range of 0-60 seconds, preferably 0-15 seconds, and more preferably 0-5 seconds.

Then, the data a is acquired in the following manner (step S2).

Firstly, the voltage switching circuit 302 is operated by command of the CPU, the electrode 11 is connected with the current/voltage conversion circuit 303 through the connector 301*a*, and the electrode 12 is connected with the reference voltage power source 305 through the connector 301*e*. Then the CPU commands application of a predetermined voltage between the electrodes in the measuring unit A. As described below, when the voltage is denoted using the electrode 11 as the positive electrode and the electrode 12 as the negative electrode, the voltage is in the range of 0.1-5.0V, preferably 1.0-3.0V, and more preferably 1.5-2.5V. The voltage application time is in the range of 0.1-30 seconds, preferably from 0.5-10 seconds, and more preferably 1-5 seconds. A signal commanding acquisition of the data a is output from the control circuit to the measuring unit A, to thereby cause the current/voltage conversion circuit 303 to convert the current amount between both electrodes resulting from application of the voltage to a voltage amount. Thereafter, the voltage amount is converted to a digital value by the A/D conversion circuit 304, inputted to the CPU, and stored in the memory of the computing unit 306 as the data a.

Thereafter, the data b is acquired as described below (step S3).

Firstly, the voltage switching circuit 302 is operated by command of the CPU, the electrode 13 is connected with the current/voltage conversion circuit 303 through the connector 301*b*, and the electrode 14 is connected with the reference voltage power source 305 through the connector 301*d*. Then, the CPU commands commencement of the measurement sequence in the measuring unit B. The voltage applied at this time is denoted using the electrode 13 as the positive electrode and the electrode 14 as the negative electrode, and is in the range of 0.05-1.0V, preferably 0.1-0.8V, and more preferably 0.2-0.6V. The voltage application time is from 0.1-30 seconds, preferably from 0.1-15 seconds, and more preferably 0.1-5 seconds. A signal commanding acquisition of the data b is output from the control circuit to the measuring unit B, and thereby cause the current/voltage conversion circuit 303 to convert the current amount flowing between both electrodes as a result of the voltage application to a voltage amount. Thereafter the voltage is converted to a digital value by the A/D conversion circuit 304, inputted to the CPU, and stored in the memory of the computing unit 306 as data b. From the point of view of enhancing the measurement speed of the analyte concentration, the control circuit preferably applies the signal commanding acquisition of the data b to the measuring unit B within a range of at least 0.5 seconds and less than 5 seconds from the time that the blood sample is introduced into the capillary 40 of the sensor chip.

The data b may be acquired prior to acquisition of the data a. However, prior to acquisition of the data b, since a sufficient period is required for dissolution of the sample, oxygen reaction of the electron mediator with oxygen, and the like, the data b is preferably acquired after acquisition of the data a. Furthermore, the data b and the data a may be acquired simultaneously. However, since a voltage is applied simultaneously to two groups of electrode systems in one solution system, there may be interference between the respective currents. Consequently, separate acquisition of the data a and acquisition of the data b is preferred.

Figure 6:
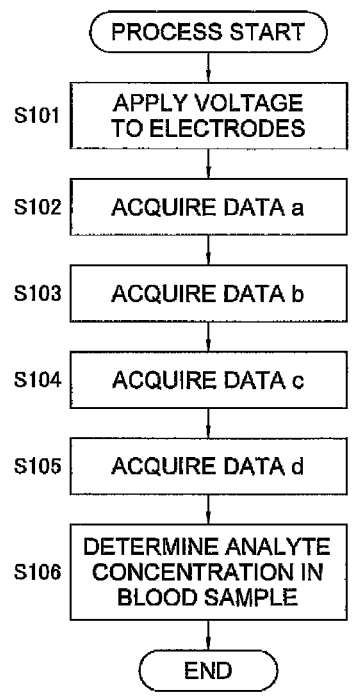
FIGS. 6(a) and 6(b) is a flowchart illustrating a method for measuring an analyte concentration in a blood sample in the biosensor system and a circuit diagram in a biosensor system according to another embodiment of the present invention.
Figure 6:
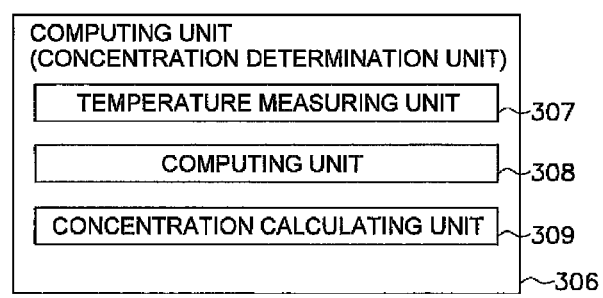

As illustrated in FIG. 6(a), the temperature when acquiring the data b is more accurately reflected in the temperature measurement results by respectively acquiring data related to temperature of the blood sample before and after the acquisition of the data b. In other words, the biosensor system 100 applies a predetermined voltage to both electrodes (step S101), acquires the data a related to the temperature of the blood sample (step S102), and then acquires the data b related to the concentration of the analyte in the blood sample (step S103). Thereafter, the data c related to the temperature of the blood sample is re-acquired (step S104). Then, the computing unit 306 calculates the data d by calculation of the average of the data a and the data c (step S105), and calculates the analyte concentration by correcting the temperature in the data b using the data d (step S106). As illustrated in FIG. 6(b), the computing unit (concentration determination unit) 306 (refer to FIG. 4) in the biosensor system 100 includes a temperature measuring unit 307 that acquires the data c related to the temperature of the blood sample based on the dimension of the current flowing through the temperature electrodes that is in contact with the blood sample after acquisition of the data b, a computing unit 308 that calculate the data d related to the temperature of the blood sample based on the data a and the data c, and a concentration calculating unit 309 that uses the data d to calculate the concentration x of the analyte that is corrected in response to the temperature of the blood sample.

Then the computing unit 306 refers to the conversion table and determines the analyte concentration in the blood sample based on the data a the data b (step S4). The determined analyte concentration is displayed on the display unit 400. If a temperature conversion table is prepared in relation to the data a, the computing unit 306 can calculate the temperature of the blood sample, and can display the temperature on the display unit 400. A computing program used in this determination may be suitably designed in response to the data structure of the conversion table. When numerical data displaying a complete correspondence with the data a and the data b is not stated in the conversion table, the computing unit 306 may determine the analyte concentration using data stated in the conversion table and a known interpolation method using data that approximates the data a and the data b.

If required, use of the electrode 11 and the electrode 12 may be used as an electrode for temperature measurement applications and an electrode for other analyte applications. The other analyte application for example includes measurement of a hematocrit value in the blood sample, and measurement of a reducing substance such as ascorbic acid, uric acid, bilirubin, acetaminophen, and the like. A method of using the electrode 11 or the electrode 12 as the working electrode (positive electrode), the electrode 13 or the electrode 14 as the counter electrode (negative electrode) is known.

In the present invention, the voltage between the temperature electrodes in the measuring unit A is affected by the configuration of the sensor chip such as the electrode material or the electrode surface area, and therefore it is necessary to determine an optimal applied voltage in advance. The current amount acquired when applying a voltage that diverges from an optimal value is affected by the hematocrit value (Hct value) in the blood sample. An Hct value means a numerical value expressing the ratio of the content of blood cells in blood.

Figure 8:
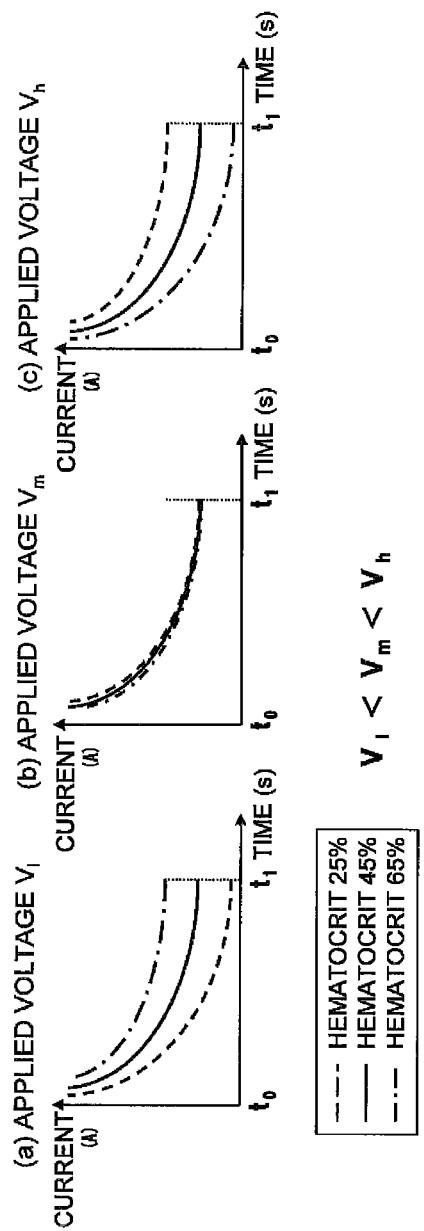
FIGS. 8(a), 8(b) and 8(c) are graphs illustrating the variation characteristics of a current obtained by use of the biosensor chip according to the first embodiment of the present invention.

When the optimal voltage value is denoted as Vm, a voltage value higher than the optimal voltage value is denoted as Vh, and a voltage value lower than the optimal voltage value is denoted as Vl, the change in the current amount expressed by (Vl<Vm<Vh) is illustrated in FIG. 8. When a voltage value Vl that is lower than the optimal voltage value is applied, as illustrated in FIG. 8(a), the current amount increases as the value Hct increases. Conversely, when the voltage value Vh is higher than the optimal voltage value is applied, as illustrated in FIG. 8(c), the current amount increases as the Hct value decreases. When the optimal voltage value Vm is used, as illustrated in FIG. 8(b), a fixed current amount is exhibited irrespective of the Hct value. A conspicuous estrangement of the current amount resulting from the Hct value is exhibited under high temperature conditions and a high current amount. Therefore the upper limiting temperature in the temperature measurement region is preferably determined in advance. The Vm range is 0.1-5.0 V, preferably 1.0-3.0 V, and more preferably 1.5-2.5 V.

In the present invention, the current amount flowing between the temperature electrodes in the measuring unit A is affected by the electrode surface area. A higher current amount is obtained when either of the surface area of a portion 31 of the electrode 11 (working electrode) and the surface area of a portion 32 of the electrode 12 (counter electrode) is increased. However it is preferred to increase the surface area of the portion 32 that is on the counter electrode side. More specifically, the range of the proportion of the surface area of the working area/the surface area of the counter electrode is preferably 1-0.25.

Even when there is a rapid change in the environmental temperature of the sensor, the biosensor system according to the embodiment enables highly accurate measurement of the analyte concentration. As a result, there is no necessity to provide an environmental temperature measuring unit such as a thermistor in the measuring device.

However, the state or configuration of the sensor may result in a low accuracy in relation to the current amount obtained by the measuring unit A. For example, in a sensor that has a small surface-area capillary 40, although the capacity of the blood sample required for measurement may be reduced, the surface area of the temperature electrodes in the measuring unit A must be reduced. Therefore, the current amount obtained in the measurement A is decreased, and as a result, it is predicted that the accuracy of the current amount obtained in the measuring unit A will be reduced. In this case, as illustrated in the circuit configuration diagram in FIG. 53, the environmental temperature measuring unit 315 may be provided in the measuring device. The number of environmental temperature measuring units 315 may be only one, or may be two or more. When two or more environmental temperature measuring units 315 are provided, respective environmental temperature measuring units 315 guarantee a more accurate measurement result for the environmental temperature by mutually monitoring of accuracy.

Furthermore, when temperature data obtained by the measuring unit A in the sensor is compared with the temperature data obtained from a thermistor provided in the measuring device, temperature correction may be executed and the respective temperature change can be monitored, an optimal temperature can be selected, and used for temperature correct. Furthermore, a method may be used in which the temperature is corrected by reference to the difference between the temperature of the measuring unit A and the temperature of the thermistor, or a method in which a plurality of temperature differences is acquired, and an optimal temperature correction value is selected. Of course, a method of utilizing data for average values and not temperature differences may be executed.

Figure 7:
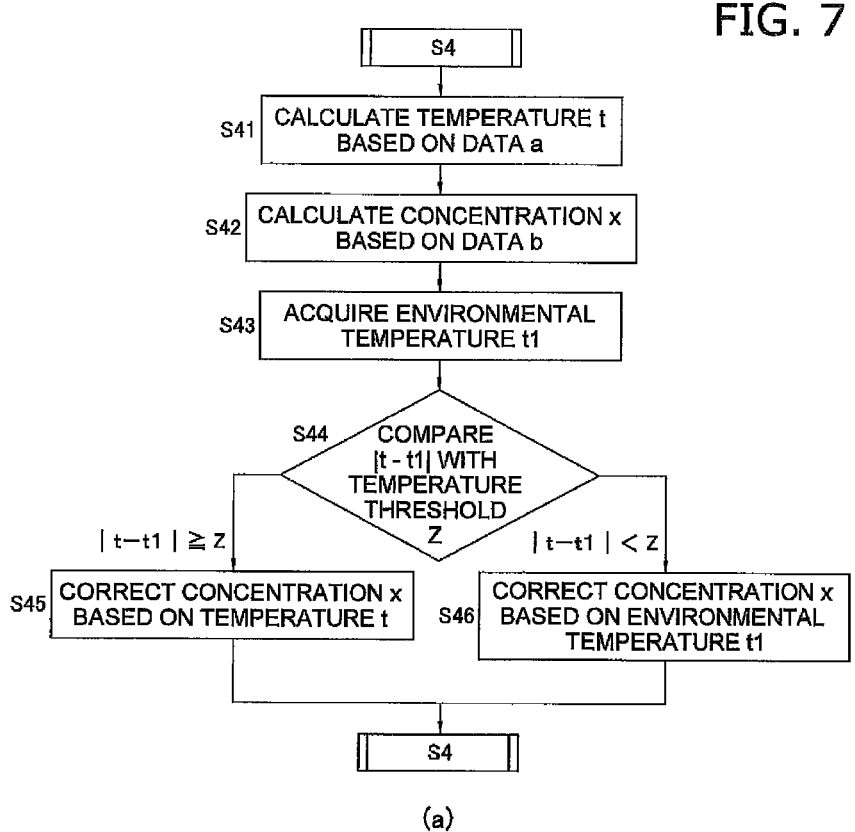
FIGS. 7(a) and 7(b) is a flowchart illustrating a method for measuring an analyte concentration in a blood sample in the biosensor system, and a circuit diagram in a biosensor system according to another embodiment of the present invention.
Figure 7:
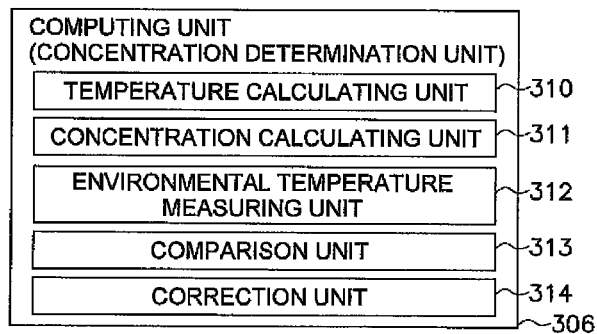
Figure 53:
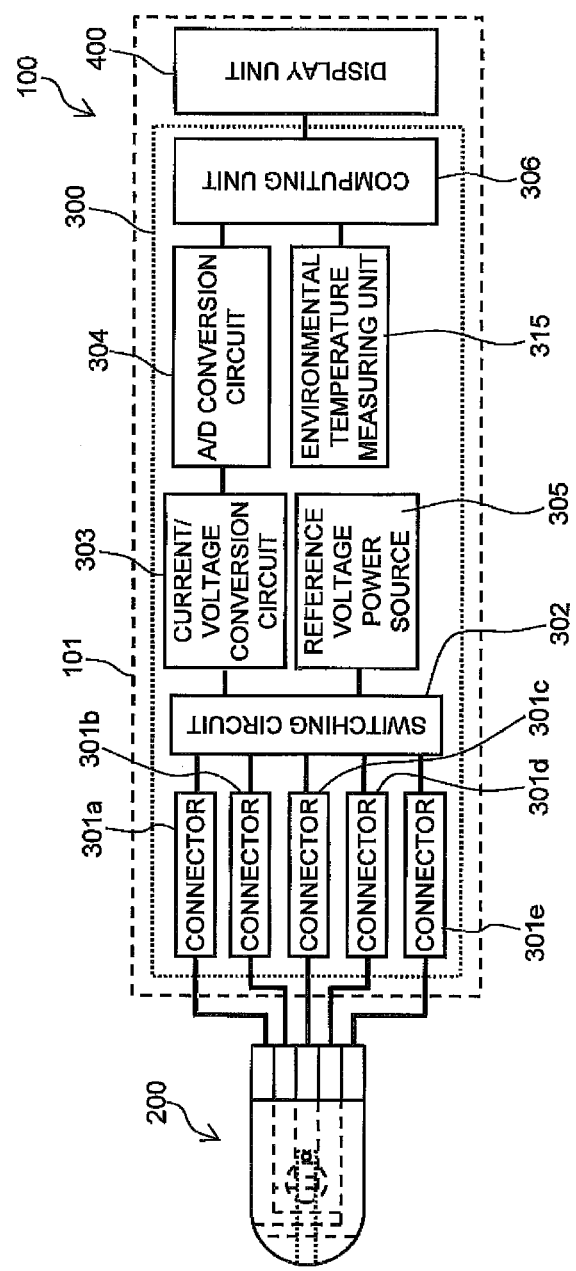
FIG. 53 is a circuit diagram for a biosensor system according to an embodiment of the present invention.

In the biosensor system 100 illustrated in FIG. 53, the computing unit 306 compares the temperature t acquired by the measuring unit A and the temperature t1 acquired by the environmental temperature measuring unit 315 in the measuring device (step S43), and uses the temperature t acquired by the measuring unit A only when there is an error between the two. That is to say, as illustrated in FIG. 7(a), the computing unit 306 calculates the temperature t based on the data a (step S41). The computing unit 306 calculates the concentration x based on the data b (step S42). The environmental temperature measuring unit 315 measures the environmental temperature t1 (step S43).

When there is no difference between the outer environmental temperature and the blood sample temperature, the computing unit 306 uses the temperature t1 (step S45) since the environmental temperature measuring unit 315 has a high measurement accuracy.

When there is a difference between the outer environmental temperature and the blood sample temperature as a result of a sharp variation in the temperature, the environmental temperature measuring unit 315 cannot adapt to the difference. Therefore, the temperature t acquired by the measuring unit A is adopted (step S46). More specifically, the temperature threshold Z is preset. The computing unit 306 is compares the value for |t−t1| with the temperature threshold Z (step S44). When the value for |t−t1| is higher than or equal to the temperature threshold Z, the computing unit 306 corrects the concentration x based on the temperature t (step S45). When smaller than the temperature threshold Z, the concentration x is corrected based on the environmental temperature t1 (step S46).

The range of the temperature threshold Z is determined in consideration of the accuracy of the environmental temperature measuring unit of the measuring device and the accuracy of the measuring unit A in the sensor chip, and is in the range of 0.01-5.0° C., preferably 0.1-2.0° C., and more preferably 0.2-1.0° C.

As illustrated in FIG. 7(b), the computing unit (concentration determination unit) 306 in the biosensor system 100 (refer to FIG. 4 and FIG. 52) includes a temperature calculating unit 310 and a concentration calculating unit 311. The temperature calculating unit 310 calculates the temperature t of the blood sample based on the data a. The concentration calculating unit 311 calculates the concentration x of the analyte of the blood sample based on the data b.

The measuring device includes an environmental temperature measuring unit 312, a comparison unit 313, and a correction unit 314. The environmental temperature measuring unit 312 measures the peripheral environmental temperature t1 of the blood sample. The comparison unit 313 compares the difference between the temperature t and the environmental temperature t1 with the temperature threshold value Z. The correction unit 314 corrects the concentration x based on the temperature t when the expression |t−t1|≥Z is satisfied, and corrects the concentration x based on the environmental temperature t1 when the expression |t−t1|<Z is satisfied.

WORKING EXAMPLES

The invention will be described in further detail below with reference to the embodiments.

Working Example 1

Figure 9:
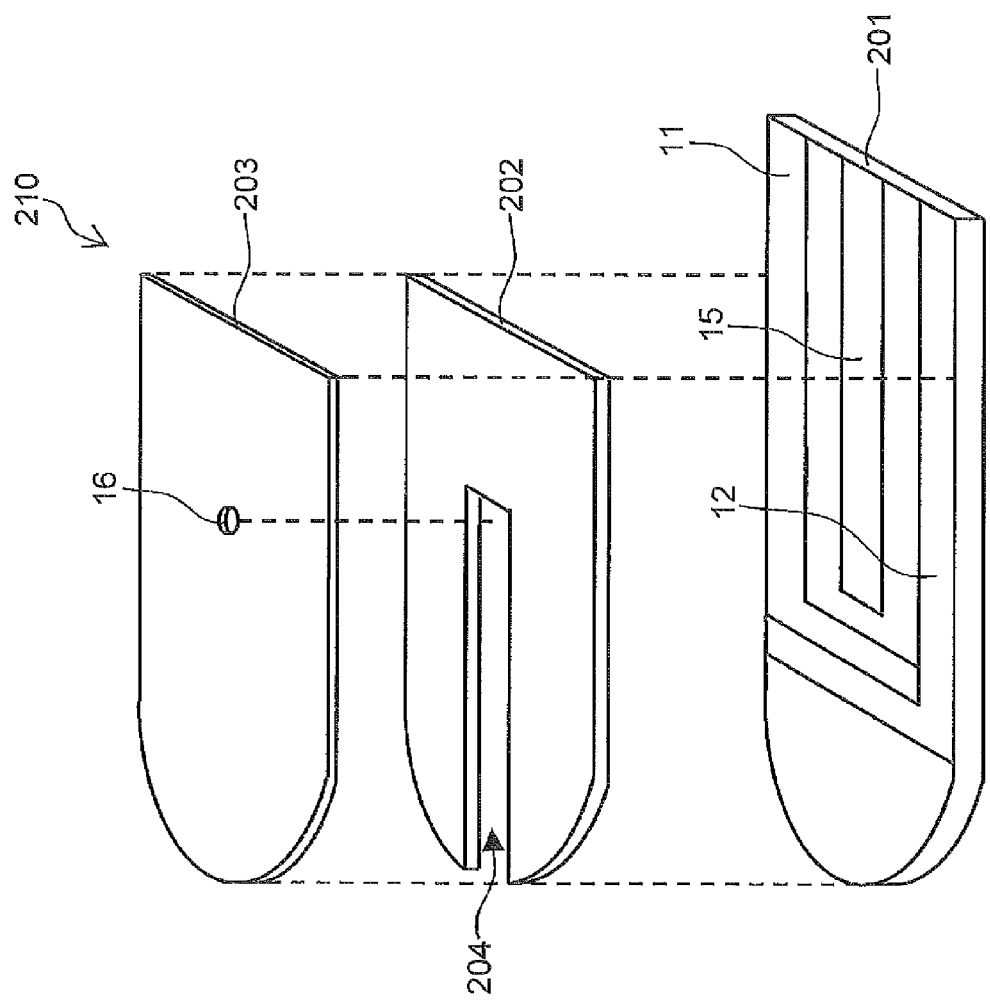
FIG. 9 is a partial perspective view of a sensor chip according to the first embodiment of the present invention.
Figure 10:
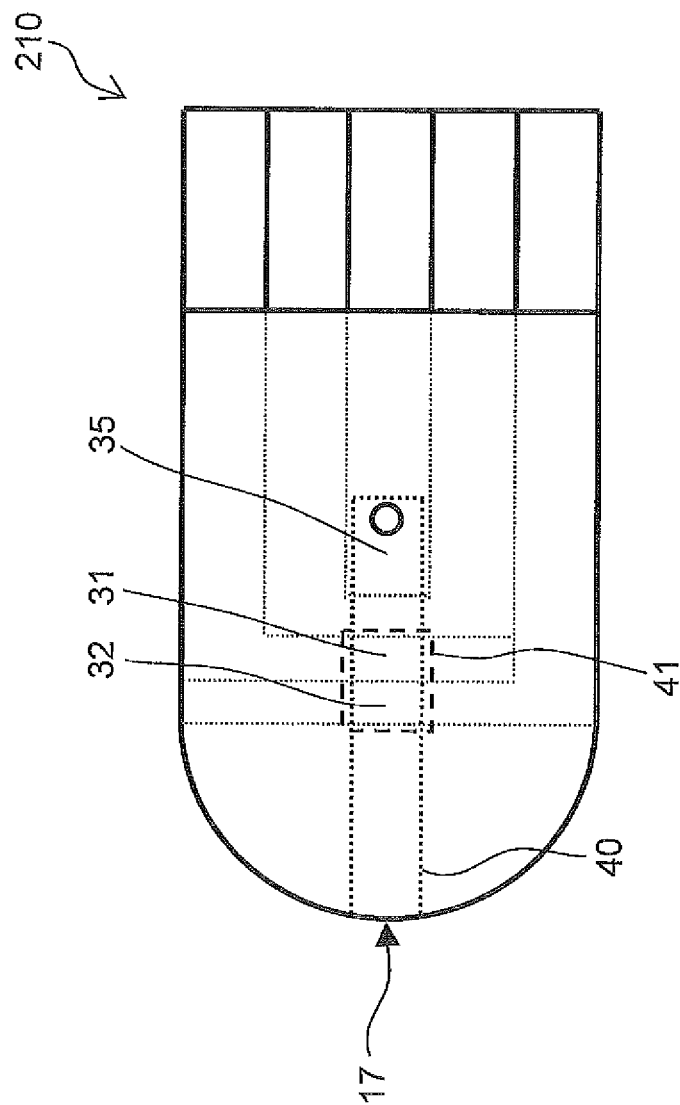
FIG. 10 is a through-view plan view of a sensor chip according to the first embodiment of the present invention.

A sensor chip 210 is prepared as illustrated in FIG. 9 and FIG. 10. The capillary is designed with a width of 1.2 mm, a length (depth) of 4.0 mm, and a height of 0.15 mm. The insulating plate is formed from polyethylene terephthalate. After palladium is deposited by vapor deposition onto the insulating plate, the respective electrodes were formed by formation of a slit in the palladium layer with a laser so that the surface area of the portion 31 of the electrode 11 is 0.12 mm$^2$, and the portion 32 of the electrode 12 is 0.48 mm$^2$.

Three types of blood samples having Hct values respectively of 25%, 45% and 65% were prepared. The temperature of the blood sample was taken to be 23° C. These blood samples were introduced into the capillary of separate sensor chips. Thereafter, the electrode 11 was used as the working electrode (positive electrode) and the electrode 12 was used as the counter electrode (negative electrode), and a voltage of 2.0V, 2.2V, or 2.4V was applied between the electrodes (temperature electrodes). The current flowing between the working electrode and the counter electrode (response current) due to application of the voltage is measured.

The measurement results are illustrated in the graphs in FIG. 11(a), FIG. 11(b), and FIG. 11(c).

When the applied voltage is 2.0V, as illustrated in FIG. 11(a), the response current increases as the Hct value increases. These results correspond to FIG. 8(a).

As illustrated in FIG. 11(b), when the applied voltage is 2.2V, the response current is fixed irrespective of the Hct value. These results correspond to FIG. 8(b).

As illustrated in FIG. 11(c), when the applied voltage is 2.4V, the response current increases as the Hct value decreases. These results correspond to FIG. 8(c).

Figure 12:
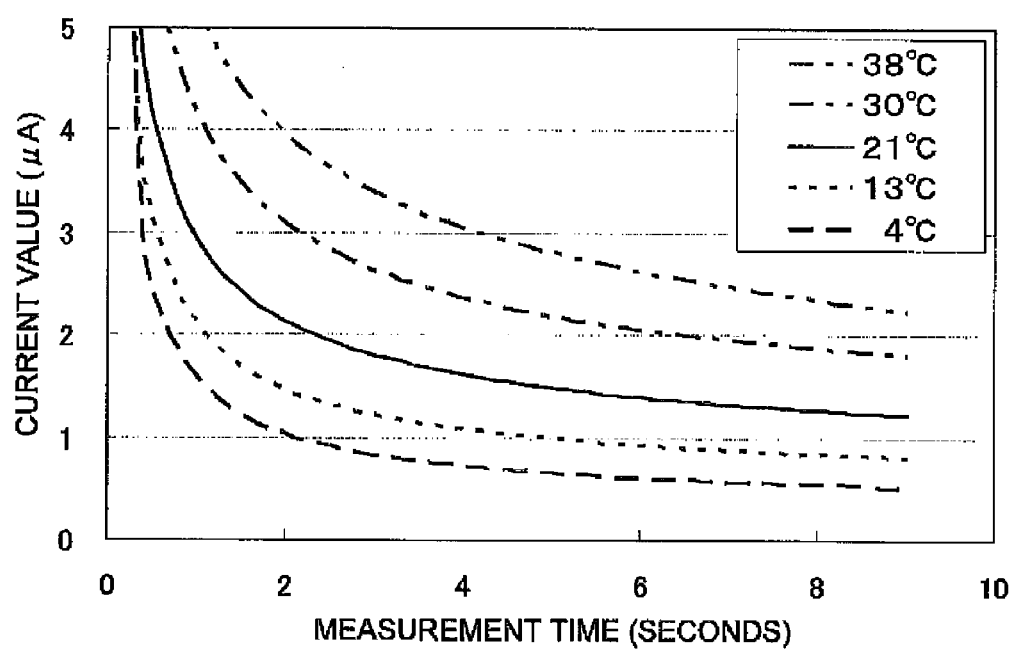
FIG. 12 is a graph illustrating the current characteristics obtained in relation to a predetermined temperature according to Working Example 1.
Figure 13:
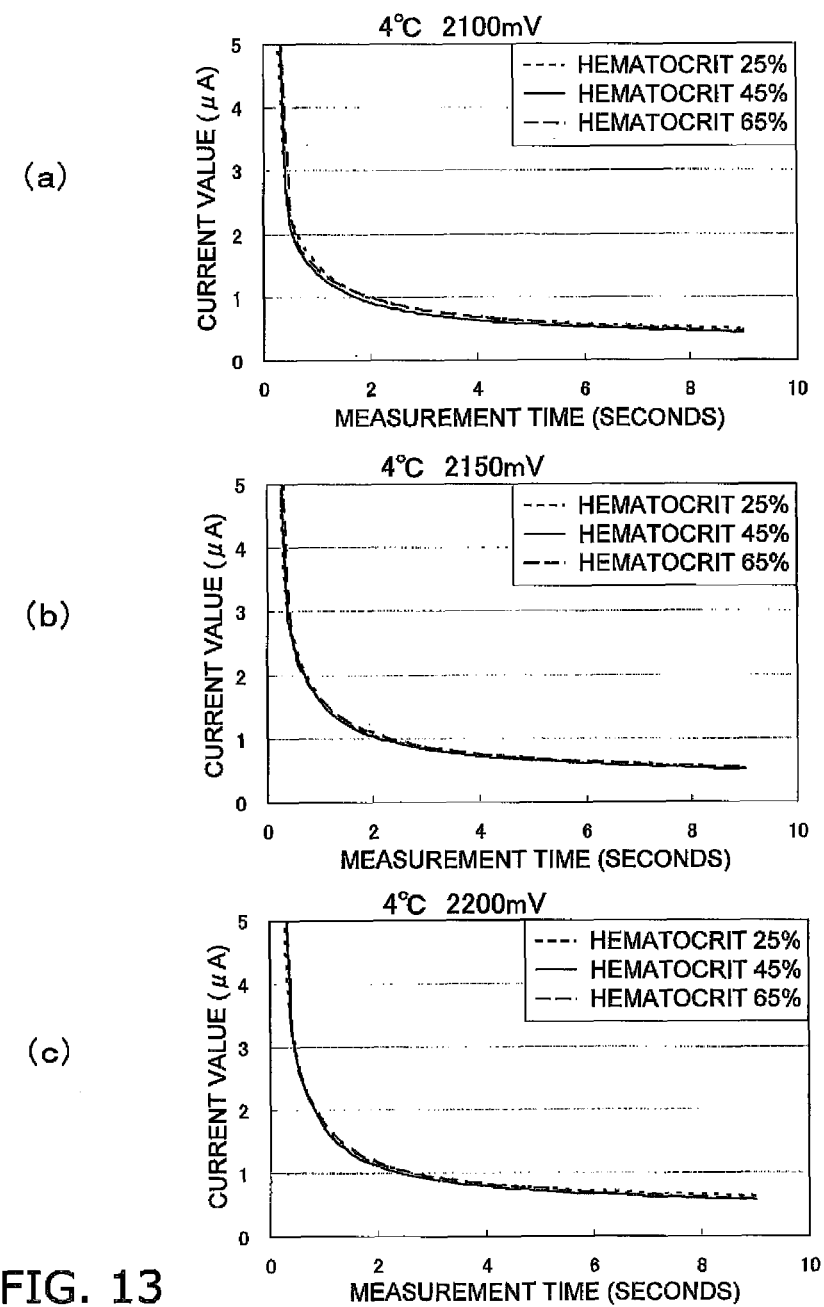
FIGS. 13(a), 13(b), and 13(c) are graphs illustrating the current characteristics obtained in relation to a predetermined applied voltage and a predetermined hematocrit value when the temperature in Working Example 7 is 4 degrees.
Figure 14:
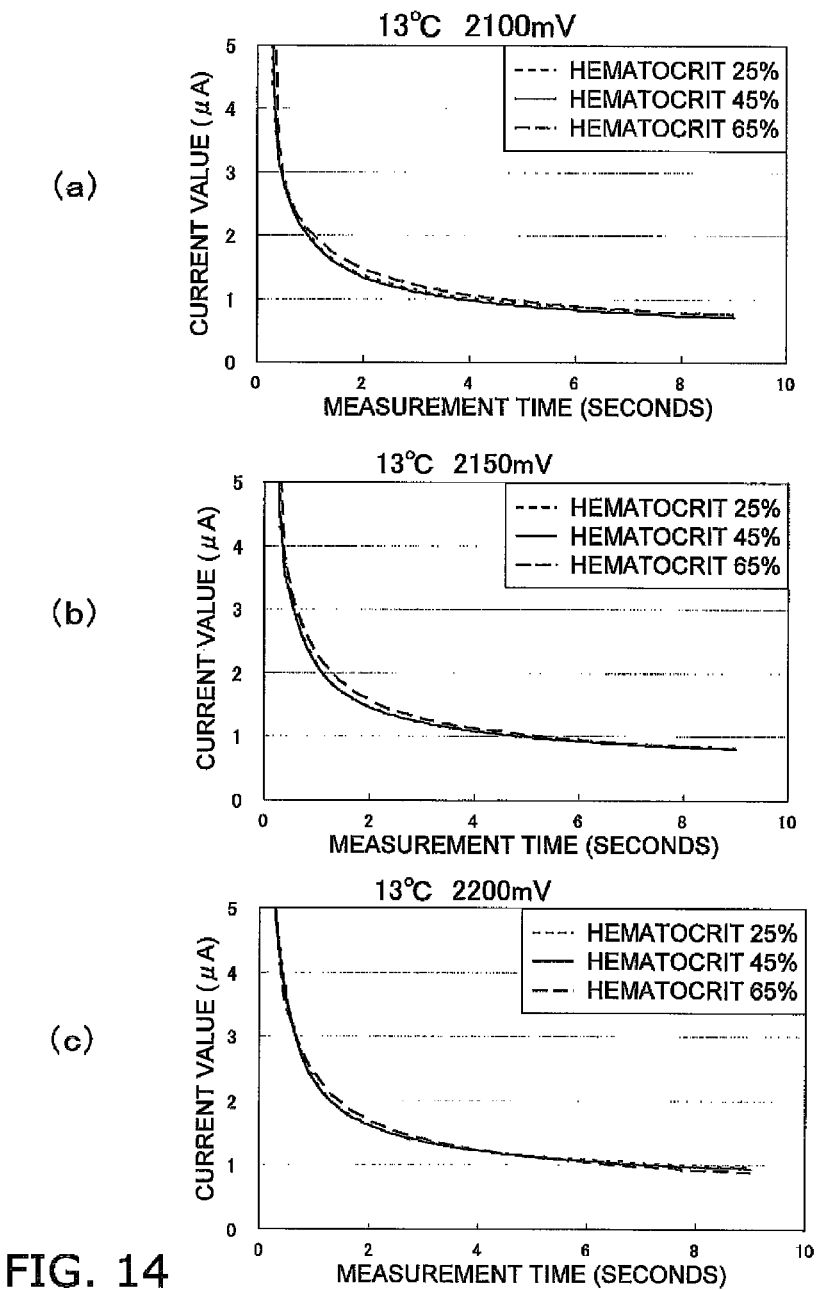
FIGS. 14(a), 14(b), and 14(c) are graphs illustrating the current characteristics obtained in relation to a predetermined applied voltage and a predetermined hematocrit value when the temperature in Working Example 7 is 13 degrees.
Figure 15:
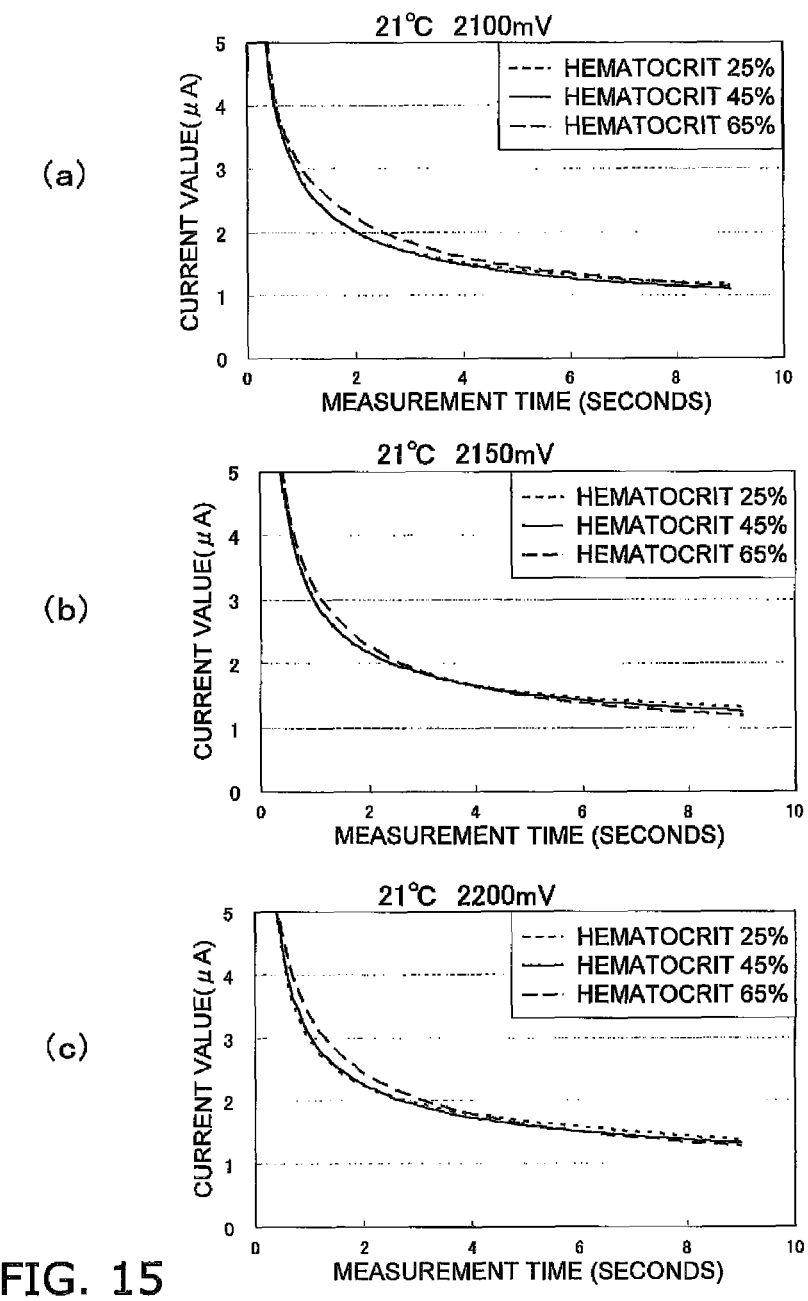
FIGS. 15(a), 15(b), and 15(c) are graphs illustrating the current characteristics obtained in relation to a predetermined applied voltage and a predetermined hematocrit value when the temperature in Working Example 7 is 21 degrees.
Figure 16:
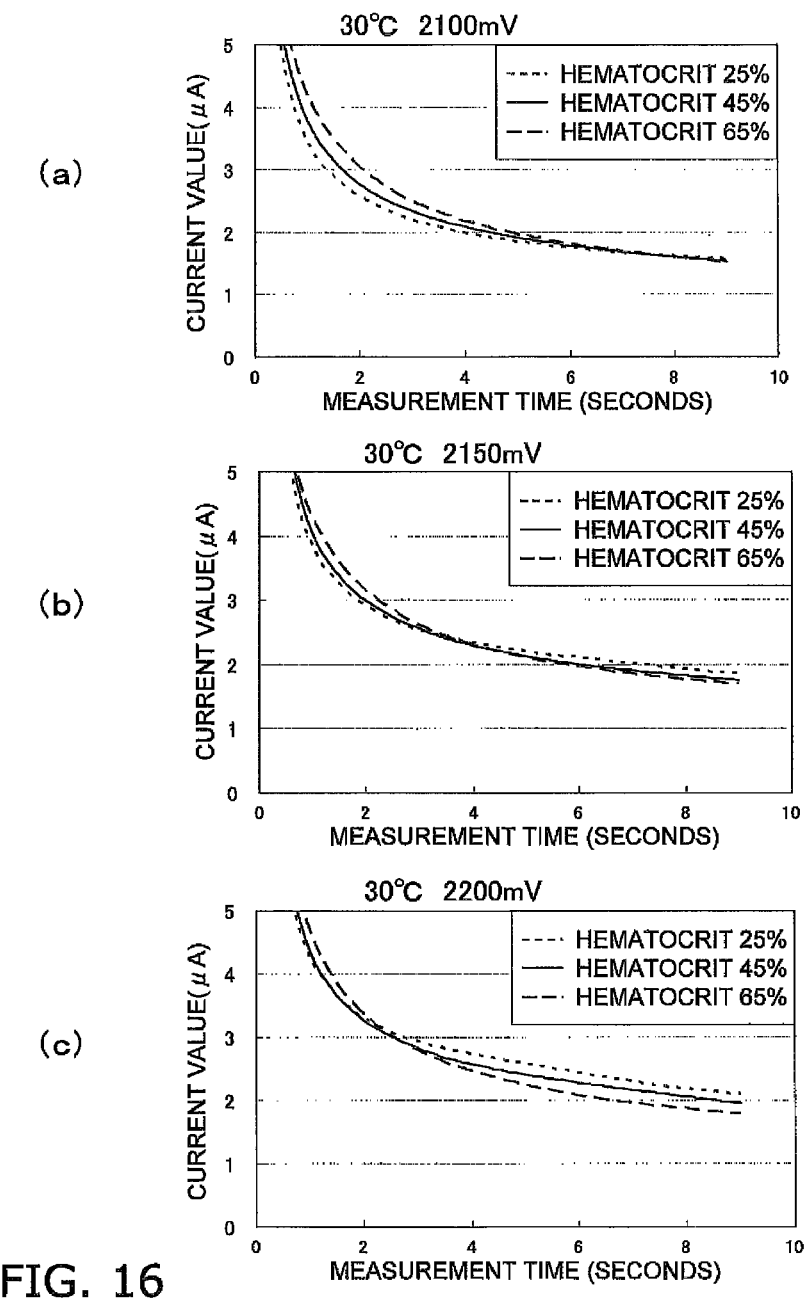
FIGS. 16(a), 16(b), and 16(c) are graphs illustrating the current characteristics obtained in relation to a predetermined applied voltage and a predetermined hematocrit value when the temperature in Working Example 7 is 30 degrees.
Figure 17:
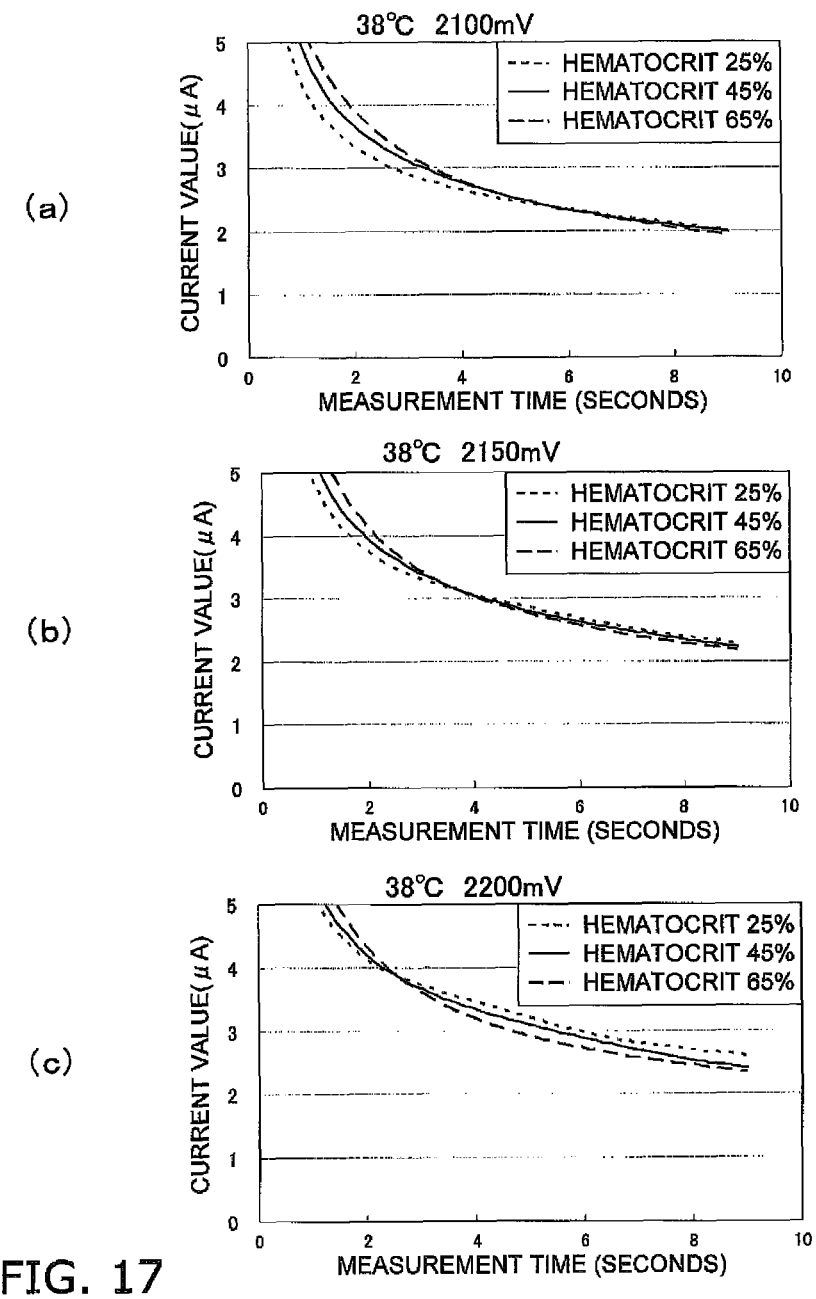
FIGS. 17(a), 17(b), and 17(c) are graphs illustrating the current characteristics obtained in relation to a predetermined applied voltage and a predetermined hematocrit value when the temperature in Working Example 7 is 38 degrees.

Next, an experiment using a blood sample with an Hct 45% at 4° C.-38° C. was performed. At each temperature, the blood sample was introduced into the capillary of separate sensor chips. Thereafter, the electrode 11 was used as the working electrode (positive electrode) and the electrode 12 was used as the counter electrode (negative electrode), and the response current was measured when a voltage of 2.2V was applied between the electrodes (temperature electrodes). The measurement results are illustrated in the graph in FIG. 12. As illustrated in FIG. 12, the response current increases as the temperature increases.

Figure 11:
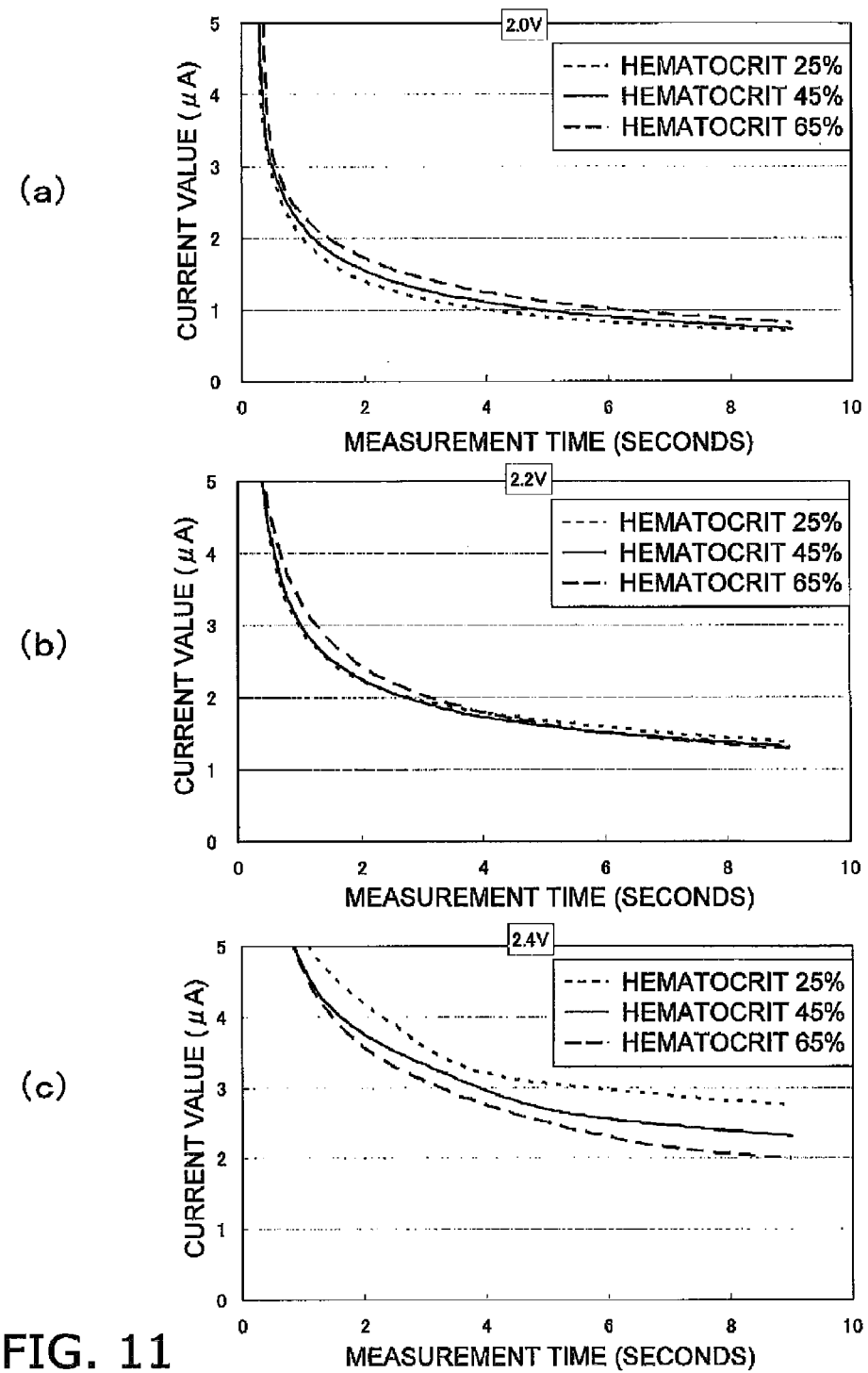
FIGS. 11(a), 11(b) and 11(c) are graphs illustrating the current characteristics of a current corresponding to FIG. 8 according to Working Example 1.

The results in FIG. 11 and FIG. 12 demonstrate that a blood sample temperature can be detected by applying a large voltage of 2.2V between the electrode 11 and the electrode 12 and thereby measuring the response current.

Working Example 2

The sensor chip having the configuration described in Working Example 1 was used, and a blood sample at a temperature of 23° C. and an Hct value of 45% was introduced into the capillary of the sensor chip. Thereafter, the electrode 11 was used as the working electrode (positive electrode) and the electrode 12 was used as the counter electrode (negative electrode), and the response current was measured when a voltage of 2.2V was applied between the electrodes (temperature electrodes). Table 1 below illustrates the current value after three seconds from initiation of voltage application. The current value in Working Example 2 was 1.88 µA.

TABLE 1

| | Electrode Surface Area (mm$^2$) | | Current Value (µA) | Current Increase Rate (%) |
|---|---|---|---|---|
| | Working Electrode | Counter electrode | | |
| Working Example 2 | 0.12 | 0.48 | 1.88 | — |
| Working Example 3 | 0.24 | 0.48 | 2.47 | 32 |
| Working Example 4 | 0.48 | 0.48 | 3.13 | 67 |
| Working Example 5 | 0.12 | 0.96 | 3.08 | 65 |
| Working Example 6 | 0.24 | 0.96 | 3.65 | 94 |

Working Example 3

An electrode was formed so that the surface area of the portion 31 of the electrode 11 of the sensor chip is 0.24 mm$^2$, and the surface area of the portion 32 of the electrode 12 of the sensor chip is 0.48 mm$^2$. Other conditions are the same as the sensor chip described in Working Example 2. Table 1 below illustrates the current value after three seconds from initiation of voltage application. The current value in Working Example 3 was 2.47 µA. When compared with Working Example 2, the current value exhibits a 32% increase. The surface area of the working electrode in the sensor chip in Working Example 3 is twice as large when compared with Working Example 2.

Working Example 4

An electrode was formed so that the surface area of the portion 31 of the electrode 11 of the sensor chip is 0.48 mm$^2$, and the surface area of the portion 32 of the electrode 12 of the sensor chip is 0.48 mm$^2$. Other conditions are the same as the sensor chip described in Working Example 2. Table 1 below illustrates the current value after three seconds from initiation of voltage application. The current value in Working Example 4 was 3.13 µA. When compared with Working Example 2, the current value exhibits a 67% increase. The surface area of the working electrode in the sensor chip in Working Example 4 is four times as large when compared with Working Example 2 and twice as large when compared with Working Example 3. In other words, it is shown that the current value increases as the surface area of the working electrode increases.

Working Example 5

An electrode is formed so that the surface area of the portion 31 of the electrode 11 of the sensor chip is 0.12 mm$^2$, and the surface area of the portion 32 of the electrode 12 of the sensor chip is 0.96 mm$^2$. Other conditions are the same as the sensor chip described in Working Example 2. Table 1 below illustrates the current value after three seconds from initiation of voltage application. The current value in Working Example 5 was 3.08 µA. When compared with Working Example 2, the current value exhibits a 65% increase. The surface area of the working electrode in the sensor chip in Working Example 5 is twice as large when compared with Working Example 2. In other words, it is shown that the current value increases as the surface area of the counter electrode increases. When compared with Working Example 3, the increase rate in the current value only reaches 32% under the condition that the surface area of the working electrode is two times. Therefore a higher response value is obtained by increasing the surface of the counter electrode more than the working electrode.

Working Example 6

An electrode is formed so that the surface area of the portion 31 of the electrode 11 of the sensor chip is 0.24 mm$^2$, and the surface area of the portion 32 of the electrode 12 of the sensor chip is 0.96 mm$^2$. Other conditions are the same as the sensor chip described in Working Example 2. Table 1 below illustrates the current value after three seconds from initiation of voltage application. The current value in Working Example 6 was 3.65 µA. When compared with Working Example 2, the current value exhibits a 94% increase. The surface area of the working electrode and the counter electrode in the sensor chip in Working Example 6 is twice as large when compared with Working Example 2. In other words, the current value is also increased in proportion to an increase in the electrode surface area when the ratio of the electrode surface areas is the same.

Working Example 7

A sensor chip as described in Working Example 1 is prepared. Fifteenth types of blood samples being combinations of three Hct values respectively of 25%, 45% and 65% and five temperatures of 4° C., 13° C., 21° C., 30° C., and 38° C. were prepared.

These blood samples were introduced into the capillary of separate sensor chips. Next, the electrode 11 was used as the working electrode (positive electrode) and the electrode 12 was used as the counter electrode (negative electrode), and a voltage of 2.1V, 2.15V, or 2.2V was applied between the electrodes (temperature electrodes) to thereby measure the response current at that time.

FIG. 13 to FIG. 17 are graphs illustrating the response current at respective temperature conditions and applied voltages. The temperature conditions and the applied voltage conditions in each graph are as illustrated below.

(Temperature Condition)
FIG. 13(a), 13(b), 13(c): 4° C.
FIG. 14(a), 14(b), 14(c): 13° C.
FIG. 15(a), 15(b), 15(c): 21° C.
FIG. 16(a), 16(b), 16(c): 30° C.
FIG. 17(a), 17(b), 17(c): 38° C.
(Applied Voltage Condition)
FIG. 13(a), FIG. 14(a), FIG. 15(a), FIG. 16(a), FIG. 17(a): 2100 mV
FIG. 13(b), FIG. 14(b), FIG. 15(b), FIG. 16(b), FIG. 17(b): 2150 mV
FIG. 13(c), FIG. 14(c), FIG. 15(c), FIG. 16(c), FIG. 17(c): 2200 mV Under the low temperature conditions of 4° C. and 13° C. in which the response current is small, a response current that is not dependent in the Hct value is exhibited in the same manner under any of the applied voltage conditions.

Under the high temperature conditions of 30° C. and 38° C. that have a large response current, a trend is observed for the response current to vary in response to the Hct value. In particular, a conspicuous difference is observed in the region of 4 seconds or less under an applied voltage condition of 2.1V and the region of 3 seconds or more under an applied voltage condition of 2.2V when compared with an applied voltage of 2.15V.

Consequently, it is important to determine an optimal application voltage conditions with reference to the response current in the high-temperature region so that the response current is not dependent upon the Hct value under different temperature conditions. The optimal application voltage determined in the above manner in Working Example 7 is 2.15V. The current value after three seconds is 1.93 μA when the blood sample is introduced at a Hct value of 45% and a temperature of 21° C. as shown in Table 2.

TABLE 2

| | Electrode Surface Area (mm$^2$) | | | |
|---|---|---|---|---|
| | Working Electrode | Counter electrode | Optimal Applied Voltage (V) | Current Value (μA) |
| Working Example 7 | 0.12 | 0.48 | 2.15 | 1.93 |
| Working Example 8 | 0.20 | 0.40 | 2.1 | 1.69 |
| Working Example 9 | 0.30 | 0.30 | 2.05 | 1.48 |

Working Example 8

An electrode was formed so that the surface area of the portion 31 of the electrode 11 of the sensor chip is 0.20 mm$^2$, and the surface area of the portion 32 of the electrode 12 of the sensor chip is 0.40 mm$^2$. Other conditions are the same as the sensor chip described in Working Example 1. As described in Working Example 7, the optimal applied voltage in Working Example 8 determined with reference to the response current in the high-temperature region is 2.1V. At this time, as illustrated in Table 2, the current value after three seconds is 1.69 μA when a blood sample with a Hct value of 45% and a temperature of 21° C. is introduced.

Working Example 9

An electrode was formed so that the surface area of the portion 31 of the electrode 11 of the sensor chip is 0.30 mm$^2$, and the surface area of the portion 32 of the electrode 12 of the sensor chip is 0.30 mm$^2$. Other conditions are the same as the sensor chip described in Working Example 1.

As described in Working Example 7, the optimal applied voltage is determined with reference to the response current in the high-temperature region. The optimal applied voltage in Working Example 9 is 2.05V. At this time, as illustrated in Table 2, the current value after three seconds is 1.48 μA when a blood sample with a Hct value of 45% and a temperature of 21° C. is introduced. The results of Working Examples 7, 8 and 9 demonstrate that the dimension of the response current varied and the optimal applied current is different when the electrode surface area is different. Furthermore, under a condition in which the sum of the surface area of the working electrode is the same as that of the surface area of the counter electrode, a larger response current is obtained when the surface area of the counter electrode is large.

Working Example 10

A sensor chip is prepared as illustrated in FIG. 2 and FIG. 3. The capillary is designed with a width of 1.2 mm, a length (depth) of 4.0 mm, and a height of 0.15 mm. The insulating plate is formed from polyethylene terephthalate, and palladium is deposited by vapor deposition onto the insulating plate. Thereafter, the respective electrodes are formed by formation of a slit in the palladium layer with a laser so that the surface area of the portion 31 of the electrode 11 is 0.30 mm$^2$, and the portion 32 of the electrode 12 is 0.48 mm$^2$.

The reaction reagent layer is formed as follows. An aqueous solution including glucose dehydrogenase, potassium ferricyanide (Kanto Kagaku Co., Ltd.), taurine (Nakalai Tesque), glucose dehydrogenase was prepared. The concentration of glucose dehydrogenase is adjusted to a concentration of 2.0 U/sensor. A concentration of 1.7 mass % of potassium ferricyanide, and 1.0 mass % of taurine was dissolved in the aqueous solution to thereby obtain a reagent liquid. After coating of the reagent liquid onto the polyethylene terephthalate plate, drying is performed at a humidity of 45% and a temperature of 21° C.

The Hct value of the blood sample is 25%, 45% and 65%, and the glucose concentration is 40 mg/dl, 80 mg/dl, 200 mg/dl, 400 mg/dl, and 1,600 mg/dl. The temperature of the blood sample was 4° C., 13° C., 22° C., 30° C., and 39° C.

The application voltage between the electrodes and the application time is set as follows. 2.075V was applied to both electrodes (temperature electrodes) being the electrode 11 (positive electrode) and electrode 12 (negative electrode) for 3 seconds from immediately after introduction of the blood sample. From 3 seconds to five seconds, 0.25V was applied to both electrodes (analysis electrode) being the electrode 13 (positive electrode) and electrode 14 (negative electrode), and at five seconds from introduction of the blood sample, the measurement is completed.

Figure 18:
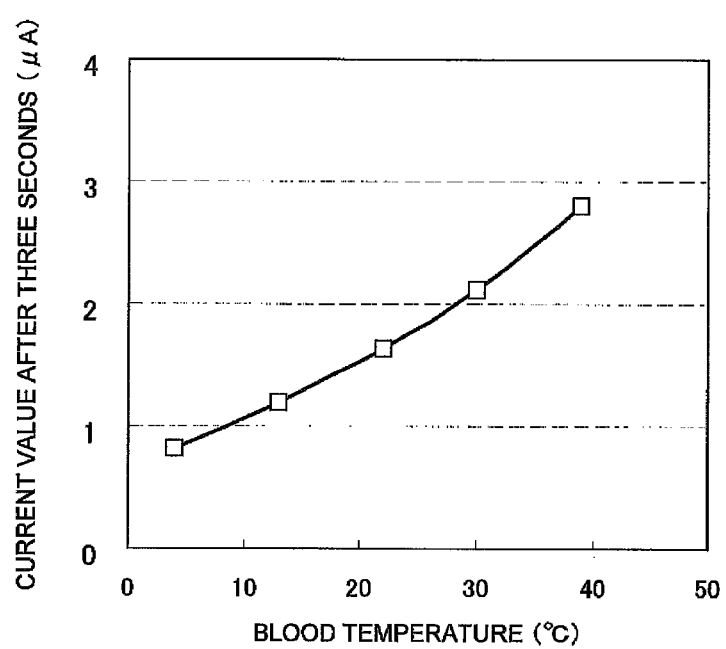
FIG. 18 is a graph illustrating the relationship with a current value obtained in relation to a predetermined temperature in Working Example 10.

Table 3 and the graph illustrated in FIG. 18 illustrate the response current value after three seconds between the temperature electrodes. The response current value after 3 seconds does not depend on the Hct value but rather depends on the temperature. The response current value after three seconds is converted to the temperature of the blood sample using the table illustrated in FIG. 18. A difference is not observed in the response current value after three seconds at different glucose concentrations. Table 4 below illustrates the response current value after 5 seconds between the analysis electrodes. The response current value after 5 seconds increases together with increases in the glucose concentration at each temperature, or increases together with increases in the temperature at each glucose concentration. When the temperature is known, the table illustrated in Table 4 below may be used as a conversion table for glucose concentration to thereby enable conversion of the response current value after 5 seconds to a glucose concentration for the blood sample.

TABLE 3

| Current value after 3 seconds (μA) | | Hematocrit | | |
|---|---|---|---|---|
| | | 25% | 45% | 65% |
| Blood Temperature | 4° C. | 0.83 | 0.82 | 0.83 |
| | 13° C. | 1.16 | 1.19 | 1.22 |
| | 22° C. | 1.66 | 1.63 | 1.64 |
| | 30° C. | 2.13 | 2.12 | 2.16 |
| | 39° C. | 2.76 | 2.81 | 2.80 |

TABLE 4

| Current value after 5 seconds (μA) | | Glucose Concentration (mg/dl) | | | | |
|---|---|---|---|---|---|---|
| | | 40 | 80 | 200 | 400 | 600 |
| Blood Temperature | 4° C. | 1.46 | 2.35 | 4.52 | 6.85 | 8.31 |
| | 13° C. | 1.75 | 2.85 | 5.60 | 9.22 | 11.89 |
| | 22° C. | 2.15 | 3.56 | 6.89 | 12.03 | 15.81 |
| | 30° C. | 2.48 | 4.35 | 8.44 | 14.82 | 20.20 |
| | 39° C. | 2.93 | 4.96 | 10.50 | 17.81 | 23.85 |

Working Example 11

Figure 19:
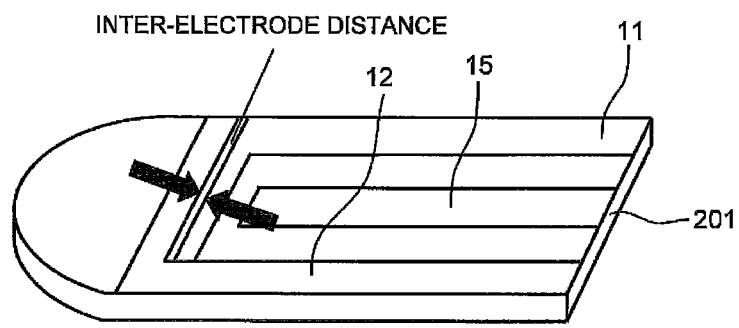
FIG. 19 is a perspective view illustrating the inter-electrode distance in the sensor chip according to Working Example 11.
Figure 20:
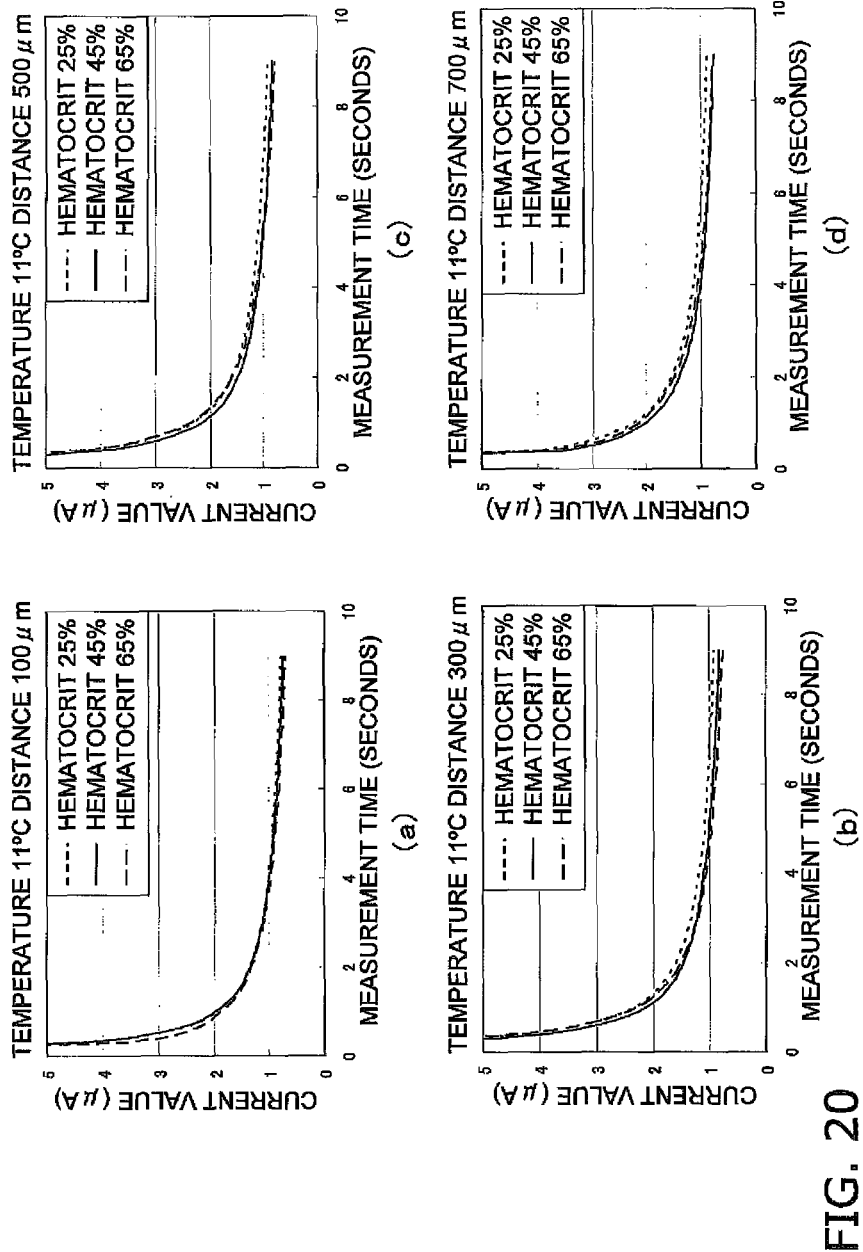
FIG. 20(a)-20D are graphs illustrating a response current value by hematocrit, and by inter-electrode distance when the blood sample is 11° C. in Working Example 11.
Figure 21:
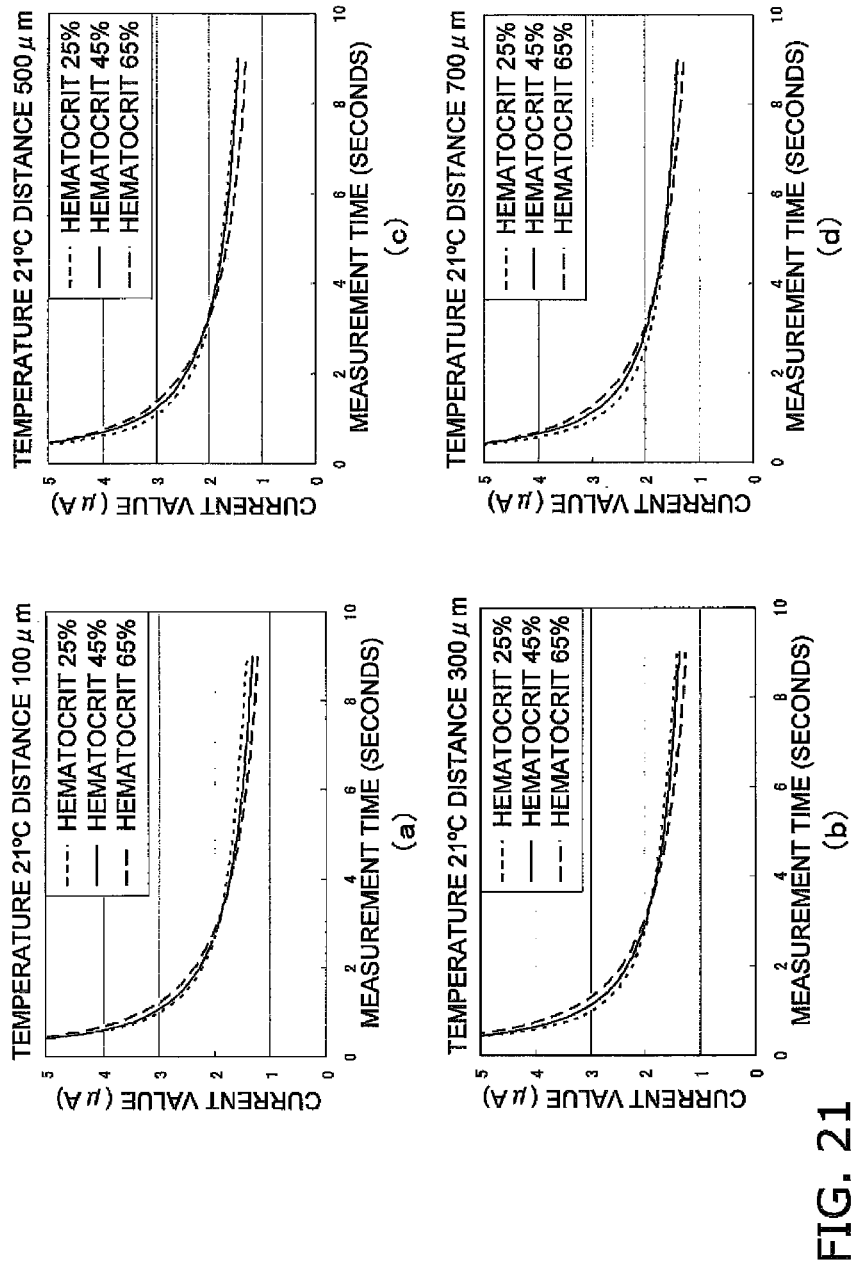
FIG. 21(a)-21(d) are graphs illustrating a response current value by hematocrit, and by inter-electrode distance when the blood sample is 21° C. in Working Example 11.
Figure 22:
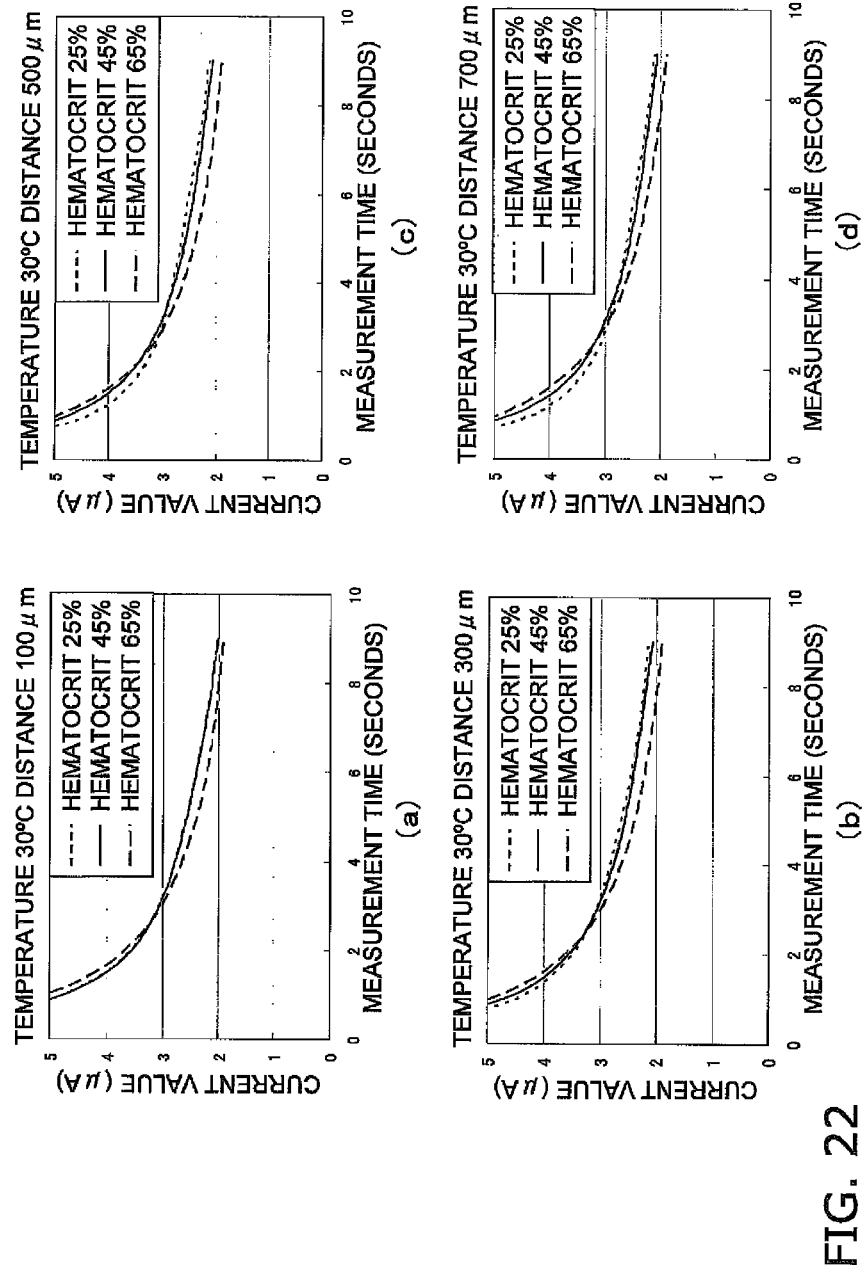
FIG. 22(a)-22(d) are graphs illustrating a response current value by hematocrit, and by inter-electrode distance when the blood sample is 30° C. in Working Example 11.

Four types of sensor chips having the configuration illustrated in FIG. 9 and FIG. 10 were prepared. In the first to the four types of sensor chips, the inter-electrode distance illustrated in FIG. 19 is respectively 100 μm, 300 μm, 500 μm, and 700 μm.

Nine types of blood samples being combinations of three Hct values respectively of 25%, 45% and 65% and three temperatures of 11° C., 21° C., and 30° C. were prepared.

Next, after introduction of the blood samples above into the capillary in the sensor chips above, a 2.2V voltage was applied between the electrodes (temperature electrodes), and the respective response currents were measured.

The measurement results are illustrated in the graphs in FIGS. 20(a)-20(d), FIGS. 21(a)-21(d), and FIGS. 22(a)-22(d). FIGS. 20(a)-20(d) illustrate the response current value in an 11° C. blood sample by inter-electrode distance and by hematocrit. FIGS. 21(a)-21(d) illustrate the response current value in a 21° C. blood sample by inter-electrode distance and by hematocrit. FIGS. 22(a)-22(d) illustrate the response current value in a 30° C. blood sample by inter-electrode distance and by hematocrit.

The graphs above do not exhibit a significant difference in the response current value when the inter-electrode distance is varied. The results of Working Example 11 demonstrate that the response current exhibits almost no effect due to the inter-electrode distance.

Working Example 12

Two types of sensor chips having different electrode shapes were prepared.

Figure 23:
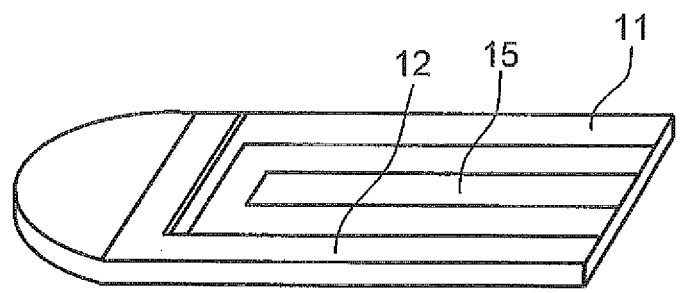
FIGS. 23(a) and 23(b) is a perspective view illustrating a sensor chip according to Working Example 12.
Figure 23:
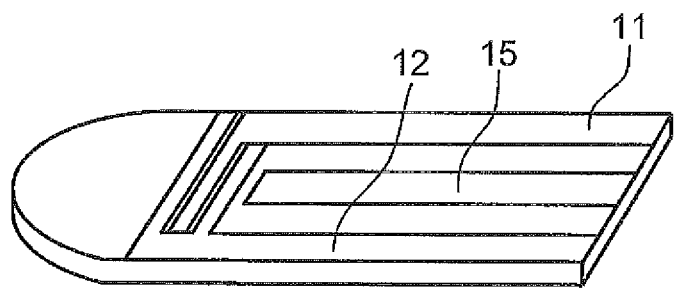

A first type of sensor chip has the configuration illustrated in FIG. 9, FIG. 10 and FIG. 23(a). In the first type of sensor chip, the surface area of the portion 31 (working electrode) of the electrode 11 is 0.24 mm², and the surface area of the portion 32 (counter electrode) of the electrode 12 of the sensor chip is 0.96 mm², and the inter-electrode distance is 300 μm.

A second type of sensor chip has the configuration illustrated in FIG. 23(b). In the second type of sensor chip, the surface area of the portion 31 (working electrode) of the electrode 11 is 0.24 mm², and the portion 32 (counter electrode) of the electrode 12 has a shape that is formed separately at two positions in FIG. 23(b). The surface area of the two portions of the portion 32 are respectively 0.48 mm². The total value for the portion 32 of the electrode 12 is 0.96 mm². In the second type of sensor chip, the inter-electrode distance is 300 μm.

Nine types of blood samples being combinations of three Hct values respectively of 25%, 45% and 65% and three temperatures of 11° C., 21° C., and 30° C. were prepared.

Next, after introduction of the blood samples above into the capillary in the sensor chips above, a 2.2V voltage was applied between the electrodes (temperature electrodes), and the respective response currents were measured.

Figure 24:
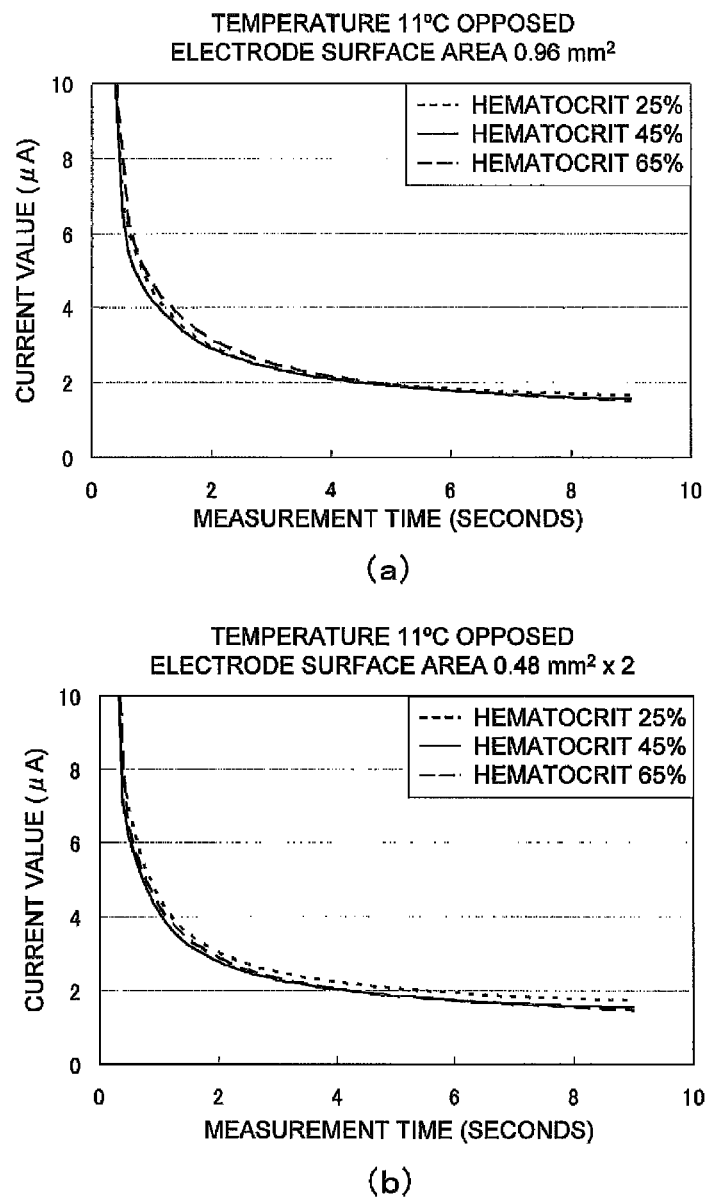
FIGS. 24(a) and 24(b) are graphs illustrating a response current value by hematocrit, and by electrode shape when the blood sample is 11° C. in Working Example 12.
Figure 25:
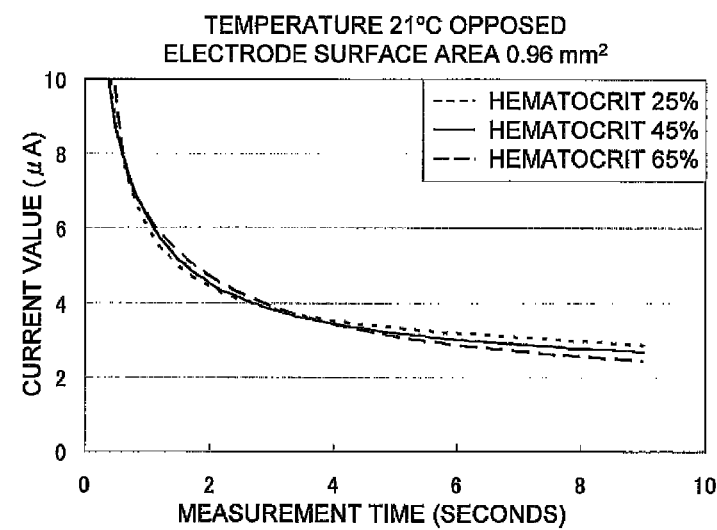
FIGS. 25(a) and 25(b) are graphs illustrating a response current value by hematocrit, and by electrode shape when the blood sample is 21° C. in Working Example 12.
Figure 25:
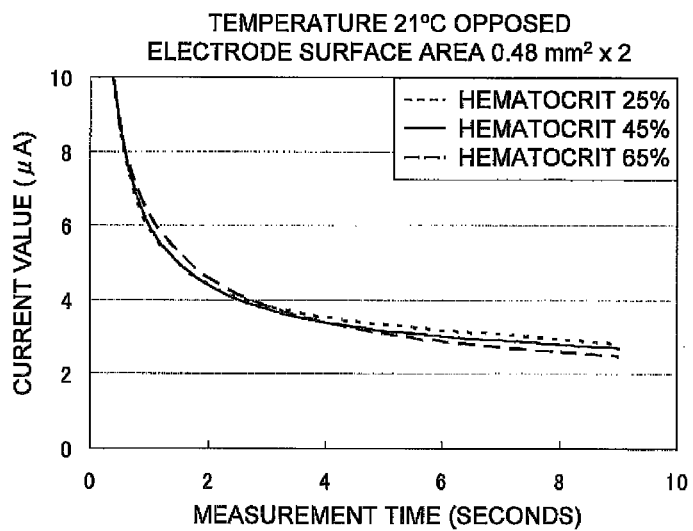
Figure 26:
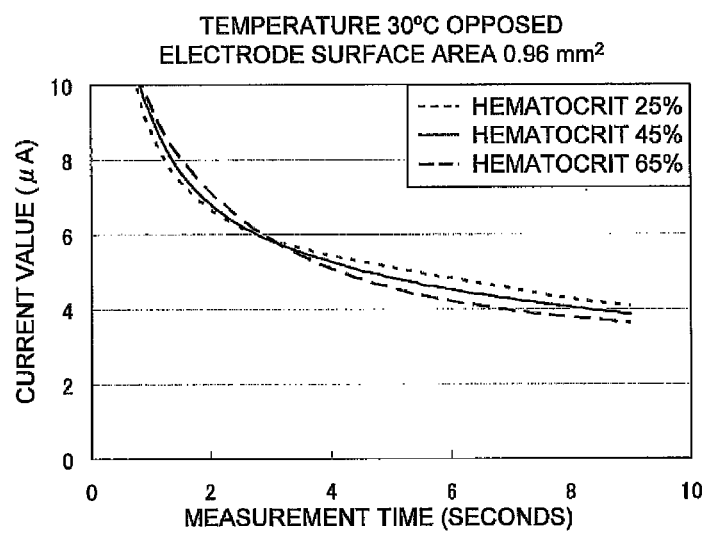
FIGS. 26(a) and 26(b) are graphs illustrating a response current value by hematocrit, and by electrode shape when the blood sample is 30° C. in Working Example 12.
Figure 26:
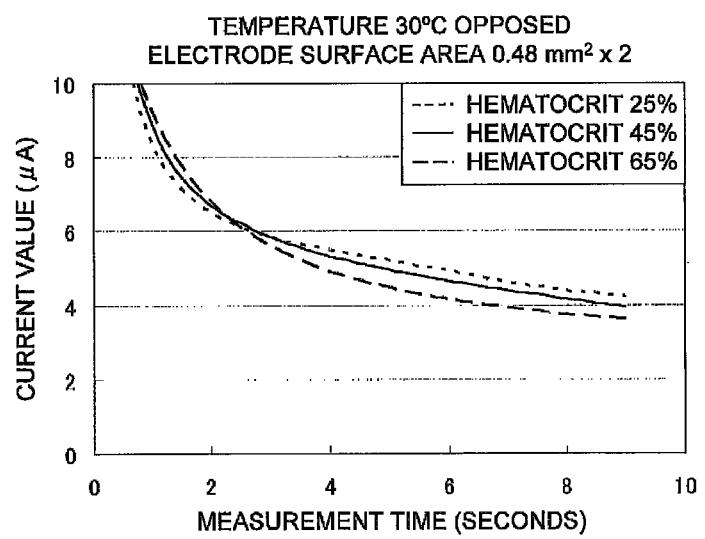

The measurement results are illustrated in the graphs in FIGS. 24(a)-24(b), FIGS. 25(a)-25(b), and FIGS. 26(a)-26(b). FIGS. 24(a)-24(b) illustrate the response current value in an 11° C. blood sample by electrode shape and by hematocrit. FIGS. 25(a)-25(b) illustrate the response current value in a 21° C. blood sample by electrode shape and by hematocrit. FIGS. 26(a)-26(b) illustrate the response current value in a 30° C. blood sample by electrode shape and by hematocrit.

The graphs above do not exhibit a significant difference in the response current value when the electrode shape distance is varied. The results of Working Example 12 demonstrate that the response current exhibits almost no effect due to the electrode shape.

Working Example 13

Figure 27:
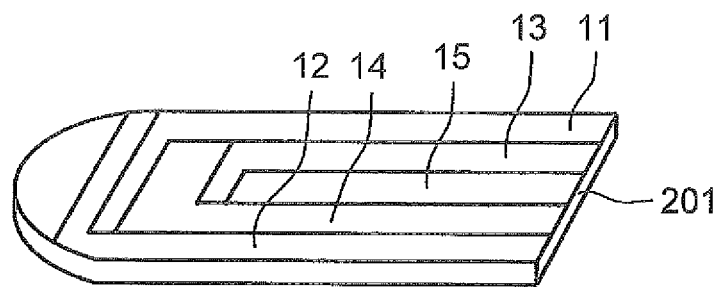
FIGS. 27(a) and 27(b) is a perspective view illustrating a sensor chip according to Working Example 13.
Figure 27:
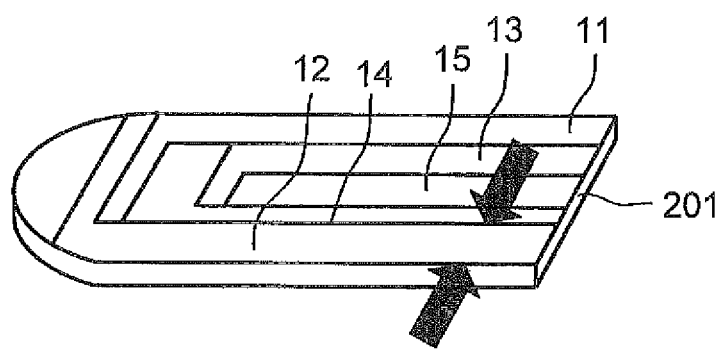
Figure 28:
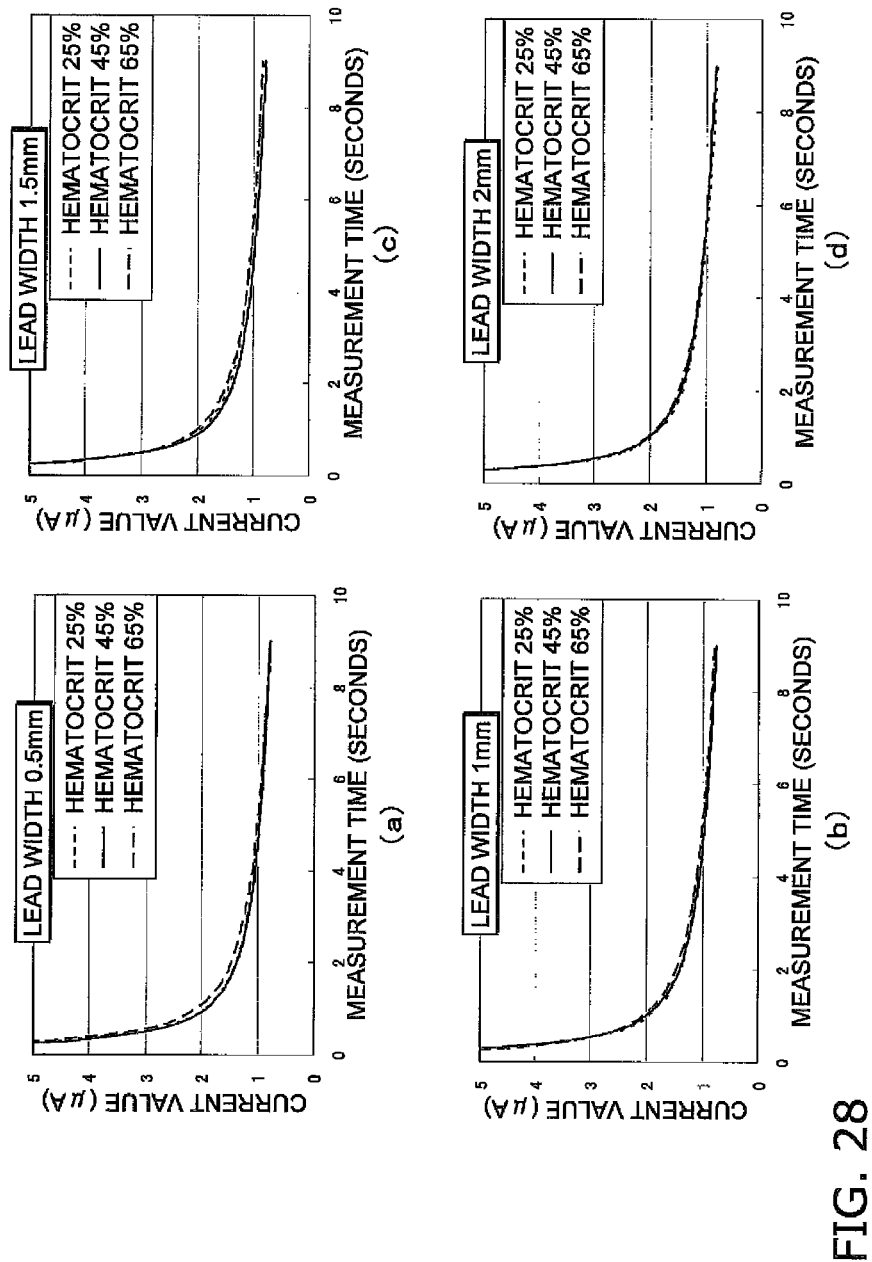
FIG. 28(a)-28(d) are graphs illustrating a response current value by hematocrit, and by lead width when the blood sample is 30° C. in Working Example 13.

Four types of sensor chips having different lead widths in the counter electrode 12 were prepared. The respective types of sensor chip have the configuration illustrated in FIG. 2, FIG. 3 and FIG. 27(a). In each type of sensor chip, the surface area of the portion 31 (working electrode) of the electrode 11 is 0.30 mm², and the portion 32 (counter electrode) of the electrode 12 is 0.30 mm², and the inter-electrode distance is 100 μm. In the first to the fourth types of sensor chip, the lead width in the counter electrode 12 illustrated in FIG. 27(b) is respectively 0.5 mm, 1.0 mm, 1.5 mm, 2.0 mm.

Three types of blood samples were prepared. The Hct values for a first to a third type of blood sample are respectively 25%, 45% and 65% and a temperature for each type of blood sample is 23° C. (room temperature).

Next, after introduction of the blood samples above into the capillary in the sensor chips above, a 2.05V voltage was applied between the electrodes (temperature electrodes), and the respective response currents were measured.

The measurement results are illustrated in the graphs in FIGS. 28(a)-28(d). These graphs demonstrate that the response current exhibits almost no change even at different hematocrit values. Furthermore, a significant difference is not observed in the response current value when the lead width is varied. The results of Working Example 13 demonstrate that the response current exhibits almost no effect due to the lead width (resistance).

Working Example 14

Figure 29:
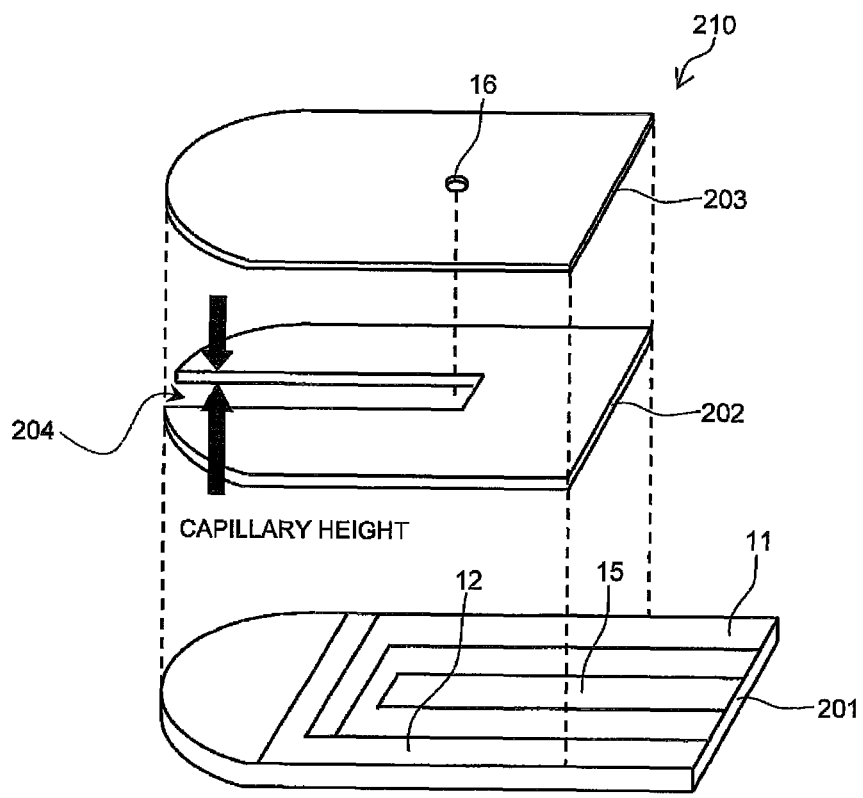
FIG. 29 is a perspective view illustrating the capillary height in the sensor chip in Working Example 14.

Two types of sensor chips were prepared. A first and a second type of sensor chip have the configuration illustrated in FIG. 9 and FIG. 10. In the first and the second type of sensor chip, the surface area of the portion 31 (working electrode) of the electrode 11 is 0.12 mm², and the surface area of the portion 32 (counter electrode) of the electrode 12 of the sensor chip is 0.48 mm², and the inter-electrode distance is 300 μm. In the first type and the second type of sensor chip, the thickness of the spacer 202 illustrated in FIG. 29 (capillary height) is respectively 0.15 mm and 0.09 mm.

Nine types of blood samples being combinations of three Hct values respectively of 25%, 45% and 65% and three temperatures of 11° C., 21° C., and 30° C. were prepared.

Next, after introduction of the blood samples above into the capillary in the sensor chips above, a 2.2V voltage was applied between the electrodes (temperature electrodes), and the respective response currents were measured.

Figure 30:
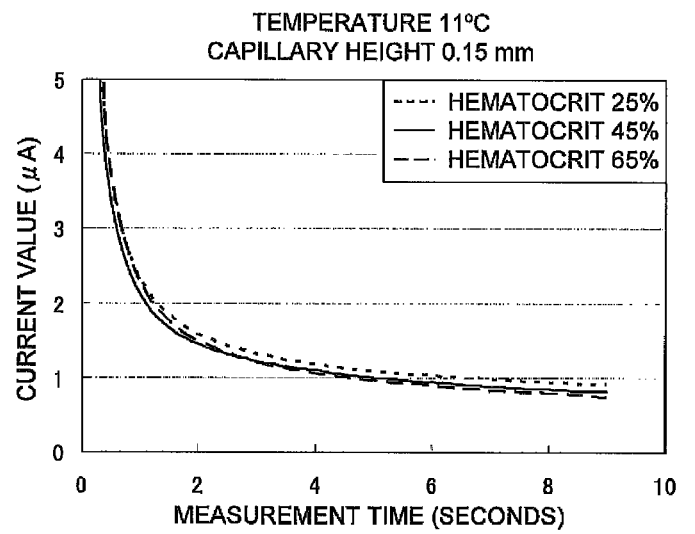
FIGS. 30(a) and 30(b) are graphs illustrating a response current value by hematocrit, and by capillary height when the blood sample is 11° C. in Working Example 14.
Figure 30:
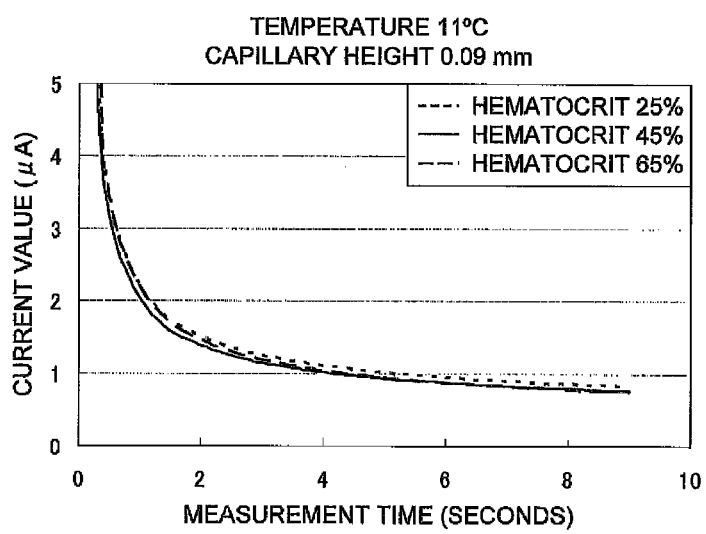
Figure 31:
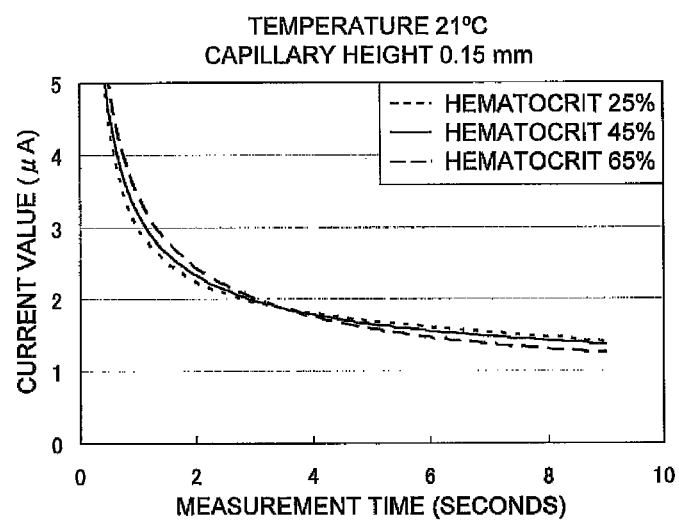
FIGS. 31(a) and 31(b) are graphs illustrating a response current value by hematocrit, and by capillary height when the blood sample is 21° C. in Working Example 14.
Figure 31:
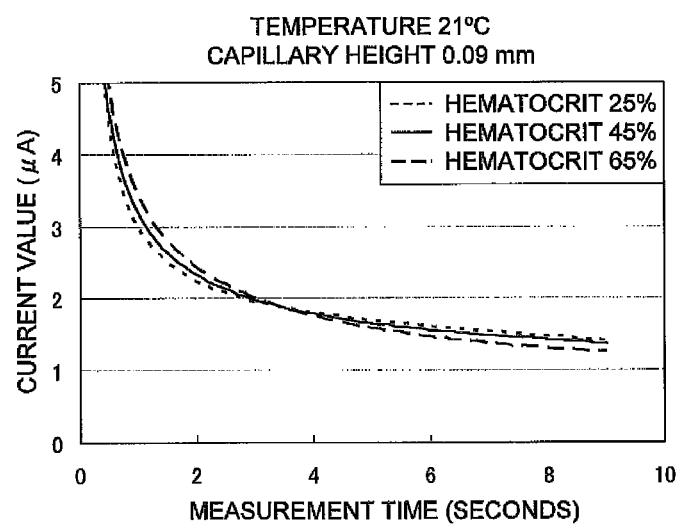
Figure 32:
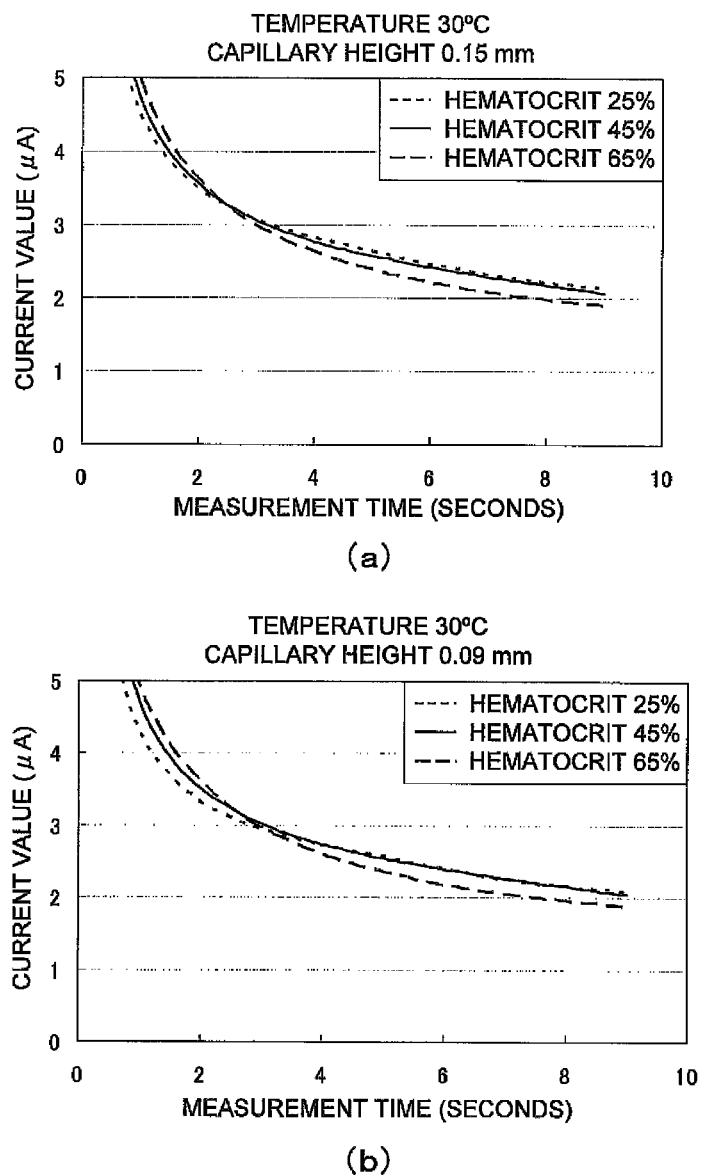
FIGS. 32(a) and 32(b) are graphs illustrating a response current value by hematocrit, and by capillary height when the blood sample is 30° C. in Working Example 14.
Figure 33:
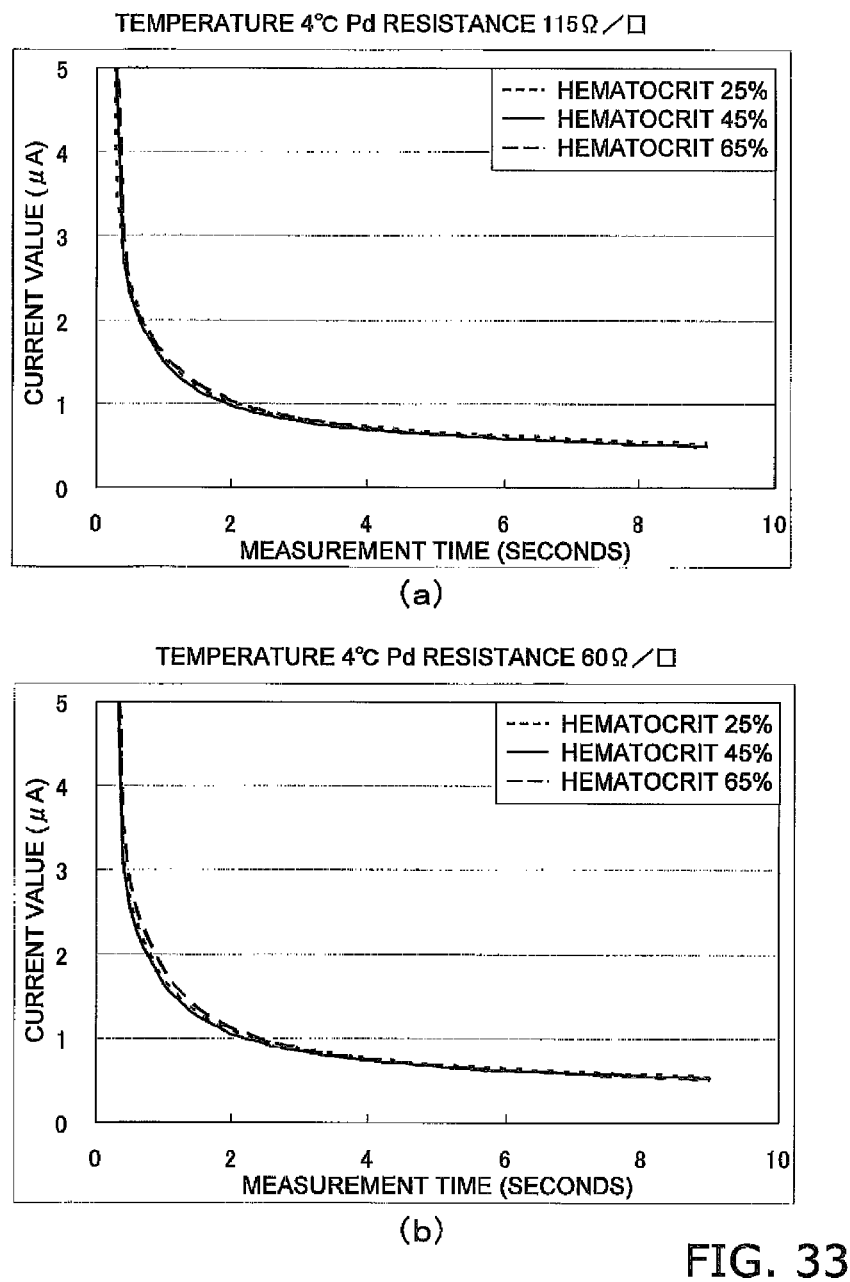
FIGS. 33(a) and 33(b) are graphs illustrating a response current value by palladium resistance when the blood sample is 4° C. in Working Example 15.
Figure 34:
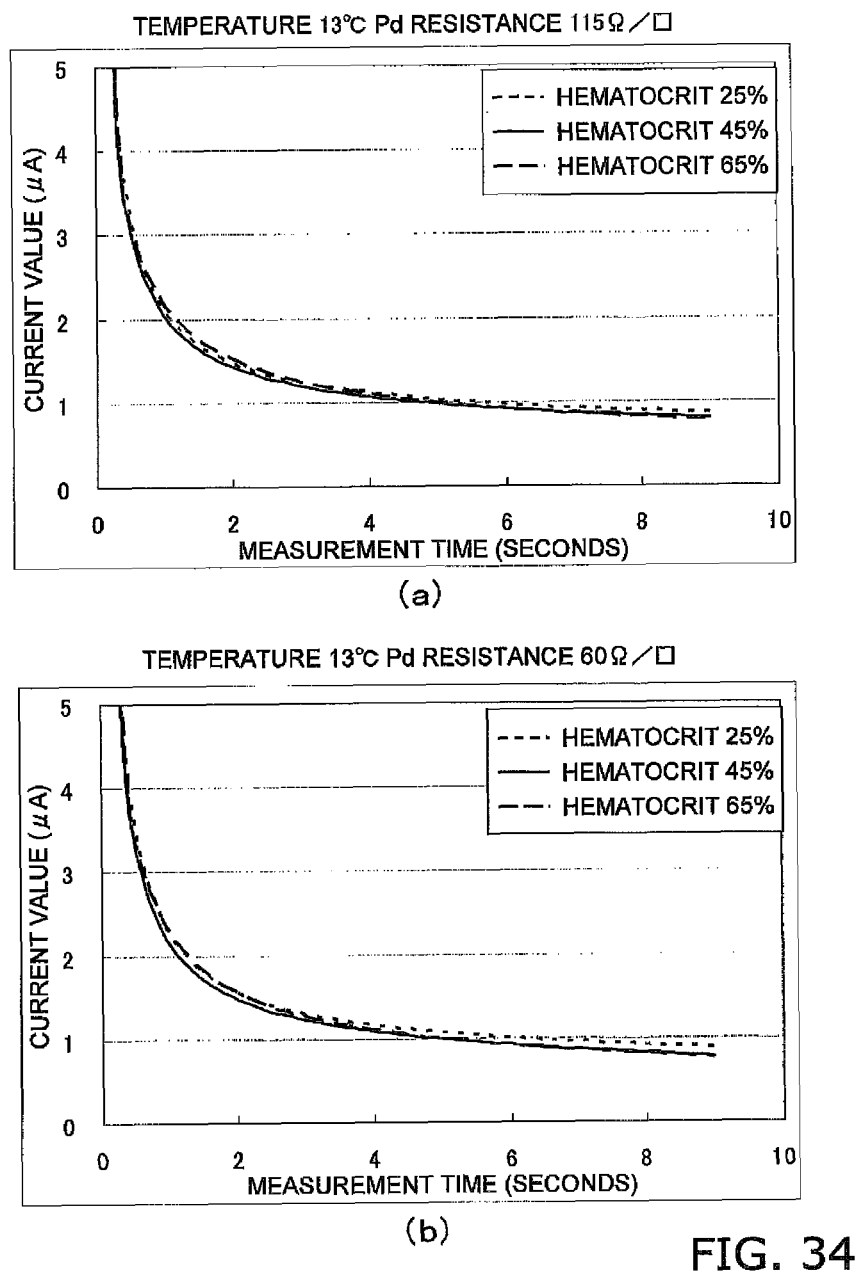
FIGS. 34(a) and 34(b) are graphs illustrating a response current value by palladium resistance when the blood sample is 13° C. in Working Example 15.
Figure 35:
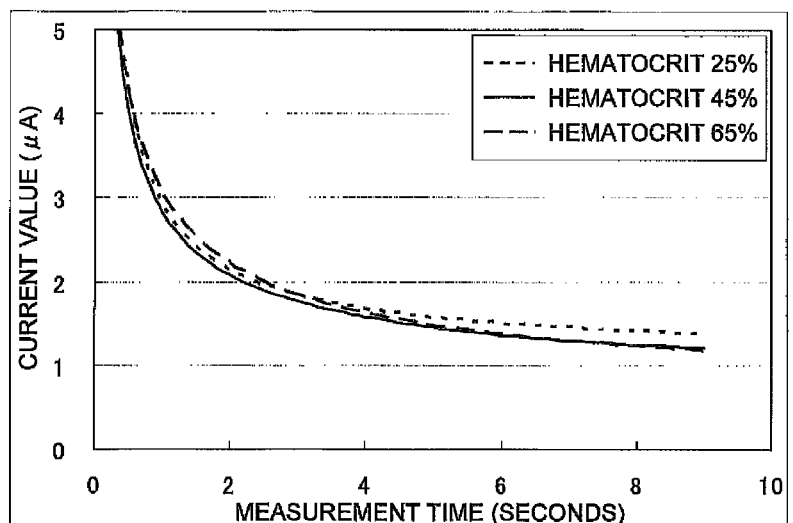
FIGS. 35(a) and 35(b) are graphs illustrating a response current value by palladium resistance when the blood sample is 21° C. in Working Example 15.
Figure 35:
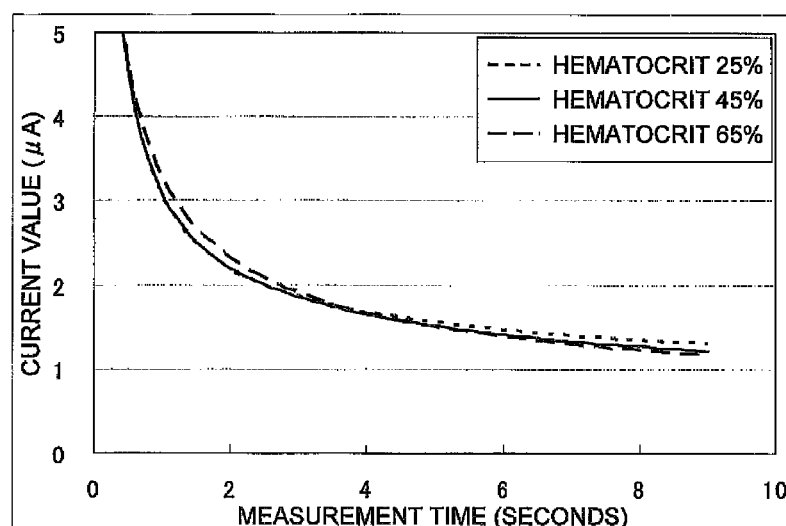
Figure 36:
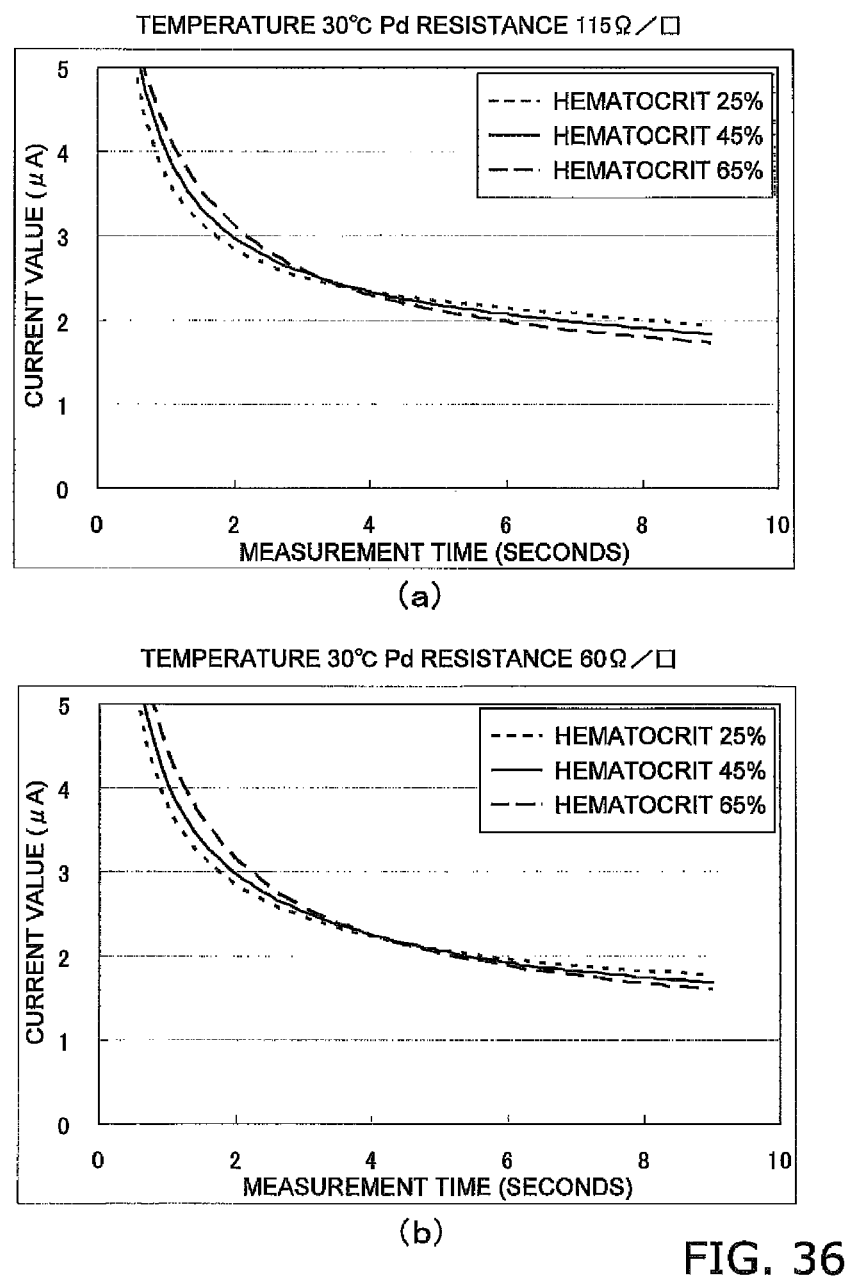
FIGS. 36(a) and 36(b) are graphs illustrating a response current value by palladium resistance when the blood sample is 30° C. in Working Example 15.
Figure 37:
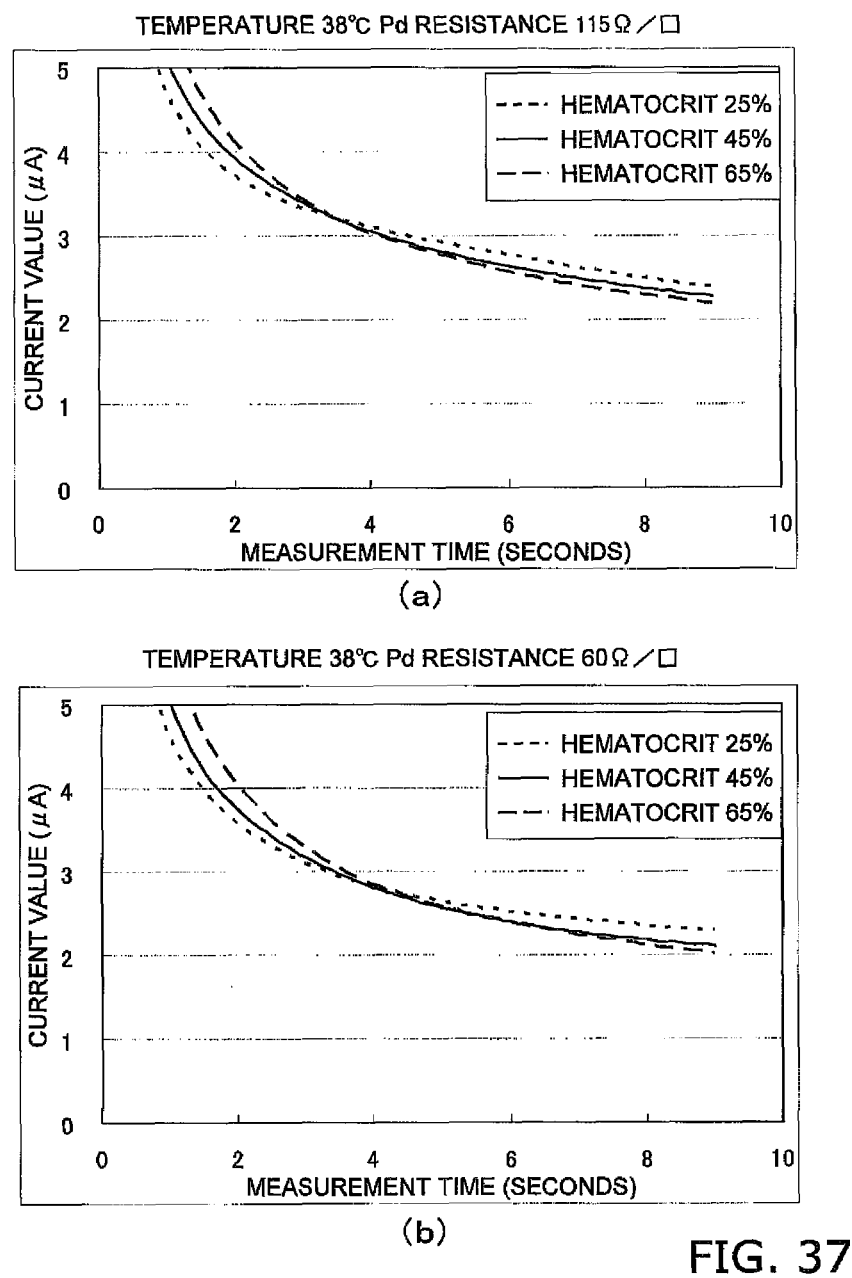
FIGS. 37(a) and 37(b) are graphs illustrating a response current value by palladium resistance when the blood sample is 38° C. in Working Example 15.

The measurement results are illustrated in the graphs in FIGS. 30(a)-30(b), FIGS. 31(a)-31(b), and FIGS. 32(a)-32(b). FIGS. 30(a)-30(b) illustrate the response current value in an 11° C. blood sample by capillary height and by hematocrit. FIGS. 31(a)-31(b) illustrate the response current value in a 21° C. blood sample by capillary height and by hematocrit. FIGS. 32(a)-32(b) illustrate the response current value in a 30° C. blood sample by capillary height and by hematocrit.

The graphs above do not exhibit a significant difference in the response current value even when the capillary height is varied. The results of Working Example 14 demonstrate that the response current exhibits almost no effect due to the capillary height.

Working Example 15

Two types of sensor chips were prepared. The respective types of sensor chip have the configuration illustrated in FIG. 9 and FIG. 10. In each type of sensor chip, the surface area of the portion 31 (working electrode) of the electrode 11 is 0.12 mm$^2$, and the surface area of the portion 32 (counter electrode) of the electrode 12 of the sensor chip is 0.48 mm$^2$, and the inter-electrode distance is 100 μm. The surface resistance of the palladium vapor-deposited plate of the first type and the second type of sensor chip is respectively 115Ω/□ and 60Ω/□.

Fifteen types of blood samples being combinations of three Hct values respectively of 25%, 45% and 65% and the temperatures of 4° C., 13° C., 21° C., 30° C., and 38° C. were prepared.

Next, after introduction of the above blood samples above into the above capillary in the sensor chips, a 2.15V voltage was applied between the electrodes (temperature electrodes), and the respective response currents were measured.

The measurement results are illustrated in the graphs in figures (a) and (b) in FIGS. 33-37. FIGS. 33(a) and 33(b) illustrate the response current value in a 4° C. blood sample by palladium resistance. FIGS. 34(a) and 34(b) illustrate the response current value in a 13° C. blood sample by palladium resistance. FIGS. 35(a) and 35(b) illustrate the response current value in a 21° C. blood sample by palladium resistance. FIGS. 36(a) and 36(b) illustrate the response current value in a 30° C. blood sample by palladium resistance. FIGS. 37(a) and 37(b) illustrate the response current value in a 38° C. blood sample by palladium resistance.

The graphs above do not exhibit a significant difference in the response current value when palladium resistance is varied. The results of Working Example 15 demonstrate that the response current exhibits almost no effect due to the palladium resistance. There is no necessity to explain that when a known conductive material such as platinum, gold, silver, titanium, copper, nickel, and carbon is applied to the plate, the same effect is obtained.

Working Example 16

Sensor chips were prepared to have the configuration illustrated in FIG. 9 and FIG. 10. In the sensor chips, the surface area of the portion 31 (working electrode) of the electrode 11 is 0.12 mm$^2$, the surface area of the portion 32 (counter electrode) of the electrode 12 of the sensor chip is 0.48 mm$^2$, and the inter-electrode distance is 100 μm.

Three types of blood samples were prepared by adding a glucose concentrate to blood having a Hct value of 45% and a temperature of 24° C. The glucose concentrations of the first to the third blood sample are respectively 0 mg/dL, 205 mg/dL, and 640 mg/dL.

Next, the above blood samples were introduced into the capillaries of the respective sensor chips above. Thereafter, a voltage of 2.15V was applied between the electrodes (temperature electrodes), and the respective response currents were measured.

Figure 38:
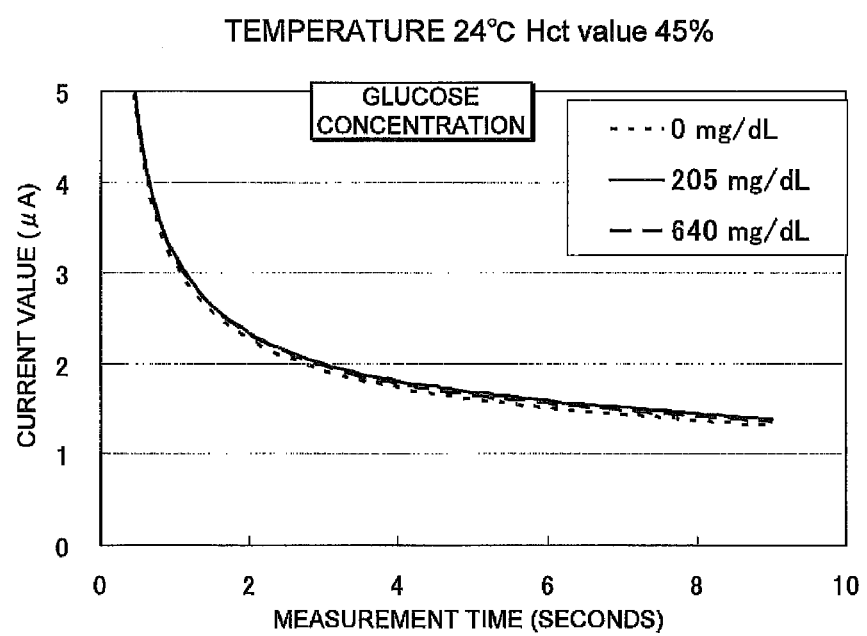
FIG. 38 is a graph illustrating response current value by glucose concentration when the blood sample is 24° C. in Working Example 15.

The measurement results are illustrated in the graph in FIG. 38. FIG. 38 illustrates the response current value in a 24° C. blood sample by glucose concentration. The graphs above do not exhibit a significant difference in the response current value when glucose concentration is varied. The results of Working Example 16 demonstrate that the response current exhibits almost no effect due to glucose concentration. When the present invention is applied to a blood glucose sensor (glucose sensor), since the measurements are not affected by the glucose concentration, it is shown that application is possible without problems.

Working Example 17

Sensor chips were prepared as in FIG. 9 and FIG. 10 so that the surface area of the portion 31 (working electrode) of the electrode 11 is 0.12 mm$^2$, the surface area of the portion 32 (counter electrode) of the electrode 12 of the sensor chip is 0.48 mm$^2$, and the inter-electrode distance is 100 μm.

Three types of blood samples with different ascorbic acid concentrations were prepared by adding an ascorbic acid concentrate to blood having a Hct value of 45% and a temperature of 24° C. The glucose concentrations of the first to the third blood sample are respectively 0 mg/dL, 10 mg/dL, and 20 mg/dL.

Next, the above blood samples were introduced into the capillaries of the respective sensor chips above. Thereafter, a voltage of 2.15V was applied between the electrodes (temperature electrodes), and the respective response currents were measured.

Figure 39:
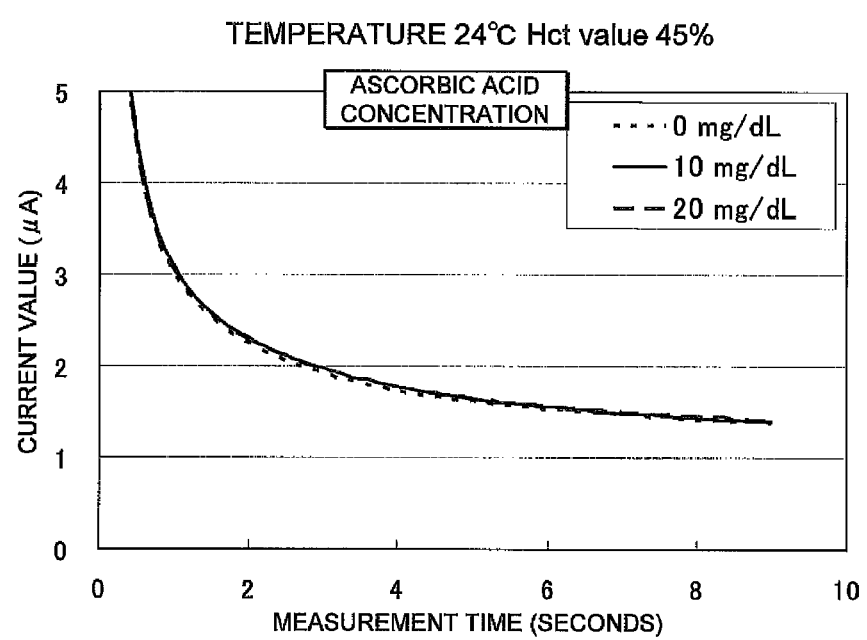
FIG. 39 is a graph illustrating response current value by ascorbic acid concentration when the blood sample is 24° C. in Working Example 17.

The measurement results are illustrated in the graph in FIG. 39. FIG. 39 illustrates the response current value in a 24° C. blood sample by ascorbic acid concentration. The graphs above do not exhibit a significant difference in the response current value when ascorbic acid concentration is varied. That is to say, in the present working example, the measurement accuracy for blood glucose level was not affected by the serum concentration of ascorbic acid, that is a reducing substance. Therefore it is shown that the sensor chip according to the present working example can be used without problems as a blood glucose level sensor.

Working Example 18

Sensor chips were prepared to have the configuration illustrated in FIG. 9 and FIG. 10. In the sensor chips, the surface area of the portion 31 (working electrode) of the electrode 11 is 0.12 mm$^2$, the surface area of the portion 32 (counter electrode) of the electrode 12 of the sensor chip is 0.48 mm$^2$, and the inter-electrode distance is 100 μm.

Two types of blood samples having different temperatures were prepared. A first type of blood sample has a Hct value of 45% and a temperature of 4° C. A second type of blood sample has a Hct value of 45% and a temperature of 42° C.

Next, one minute after moving the above blood samples to a 24° C. environment, the samples were introduced into the capillaries of the respective sensor chips described above. Thereafter, a voltage of 2.15V was applied between the electrodes (temperature electrodes), and the respective response currents were measured.

Figure 40:
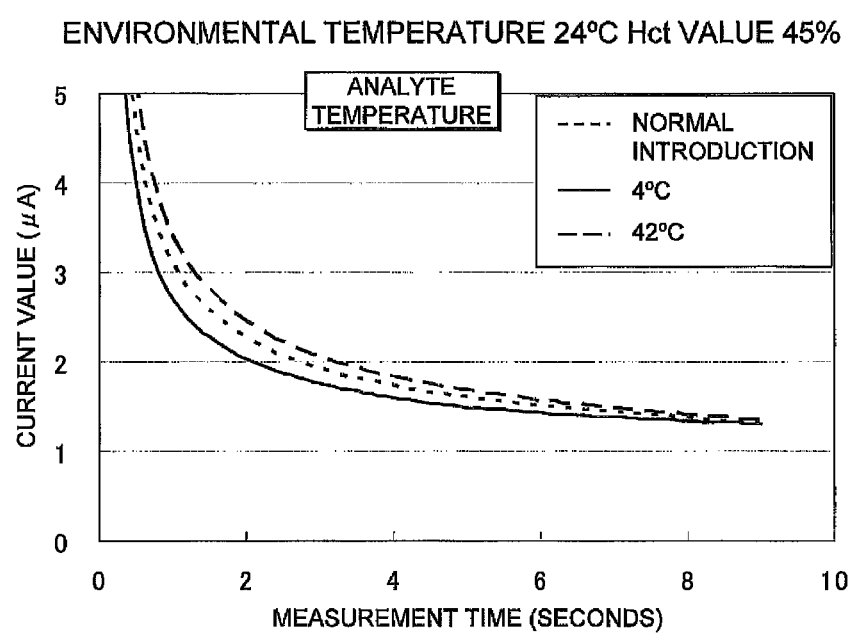
FIG. 40 is a graph illustrating response current value by temperature when the blood sample is introduced in an environment of 24° C. in Working Example 18.

The measurement results are illustrated in the graph in FIG. 40. The dotted line in FIG. 40 illustrates the response current value when introducing blood at 24° C. to a 24° C. environment (hereinafter referred to as "normal introduction"). The solid line in FIG. 40 illustrates the response current value when introducing blood at 4° C. to a 24° C. environment (hereinafter referred to as "4° C. introduction"). The broken line in FIG. 40 illustrates the response current value when introducing blood at 42° C. to a 24° C. environment (hereinafter referred to as "42° C. introduction").

The graphs illustrate that during a time period soon after the measurement period, the temperature exhibited by the 4° C. introduction is low in comparison to the temperature exhibited by the normal introduction, and the temperature exhibited by the 42° C. introduction is high in comparison to the temperature exhibited by the normal introduction. Over the passage of time during the measurement period, the temperature difference between the 42° C. introduction and the 4° C. introduction disappears. The fact that the temperature difference disappears due to the passage of the measurement period is thought in both cases to result from the movement of the blood sample at 4° C. or 42° C. to a 24° C. environment, and therefore over the passage of time, both samples shift to 24° C. that is the temperature of the sensor chip.

According to Working Example 18, it is shown that measurement of temporal variation in relation to the temperature of the blood sample is possible.

Furthermore, the sensor chip is provided with a temperature electrode that is disposed to make contact with the blood sample, and measures the temperature of the blood sample. Therefore, when the sensor chip is used, a temperature for the blood sample that takes into consideration temporal variation can be obtained, and this value can be used to correct the glucose concentration and the like. In other words, the accuracy of various types of corrections can be improved.

Working Example 19

Sensor chips were prepared to have the configuration illustrated in FIG. 9 and FIG. 10. In the sensor chips, the surface area of the portion 31 (working electrode) of the electrode 11 is 0.12 mm$^2$, the surface area of the portion 32 (counter electrode) of the electrode 12 of the sensor chip is 0.48 mm$^2$, and the inter-electrode distance is 100 µm.

A blood sample was prepared. The blood sample has a Hct value of 45%.

Figure 41:
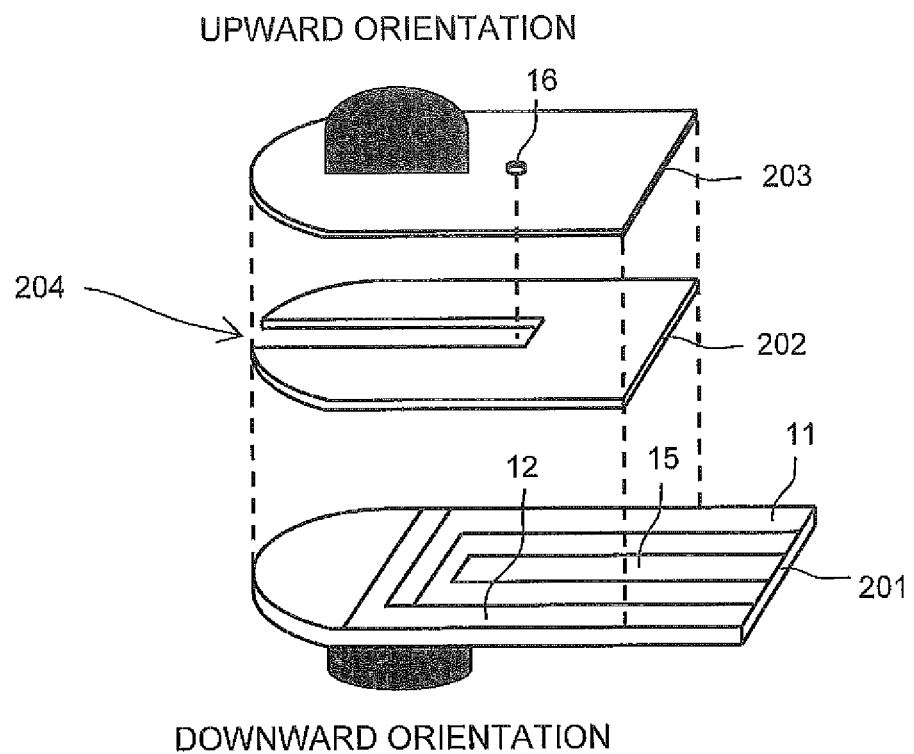
FIG. 41 is a perspective view illustrating the upward orientation and downward orientation of the sensor chip according to Working Example 19.

As illustrated in FIG. 41, approximately 3 µL of blood was dripped in advance into the sensor chip. The blood was dripped onto an upper portion of the cover 203. Dripping blood in this manner is hereinafter referred to as "upward orientation".

Approximately 10 µL of blood was dripped in advance into the other sensor chip. The blood was dripped onto a lower portion of the insulating plate 201. Dripping blood in this manner is hereinafter referred to as "downward orientation".

Next, the above blood samples were introduced in a 24° C. environment into the capillaries 204 of the respective sensor chips. Thereafter, a voltage of 2.15V was applied between the electrodes (temperature electrodes), and the respective response currents were measured.

Figure 42:
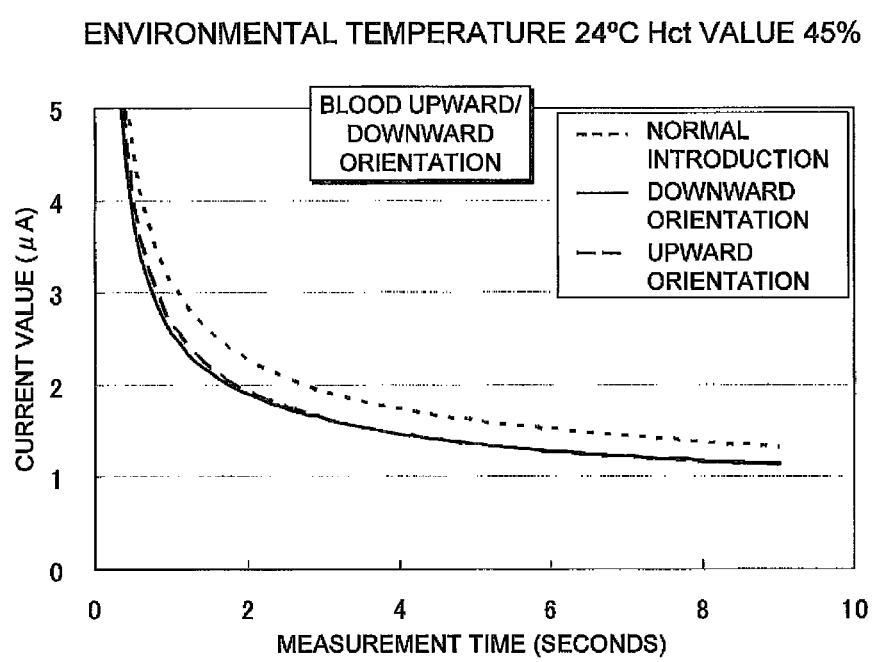
FIG. 42 is a graph illustrating a response current value when blood is attached in an upward orientation and a downward orientation in an environment of 24° C. according to Working Example 19.

The measurement results are illustrated in the graph in FIG. 42. The broken line in FIG. 42 illustrates the response current when dripping blood in advance in an upward orientation in a 24° C. environment. The solid line in FIG. 42 illustrates the response current when dripping blood in advance in a downward orientation in a 24° C. environment. The dotted line in FIG. 42 illustrates the response current when dripping blood in advance in both an upward orientation and a downward orientation in a 24° C. environment (hereinafter referred to as "normal introduction").

The graphs illustrate that in comparison to normal introduction, the response current value is low during an upward orientation and during a downward orientation. This is thought to be due to the fact that the temperature of the blood sample in the capillary 204 is reduced by the heat of evaporation of blood in an upward orientation and during a downward orientation that becomes excessively attached to an outer range of the capillary 204.

Working Example 19 enables comprehension of the effect of heat of evaporation as illustrated in FIG. 42.

The sensor chip is provided with a temperature electrode that is disposed to make contact with the blood sample, and that measures the temperature of the blood sample. Therefore, a temperature for the blood sample that takes into consideration heat of evaporation can be obtained, and this value can be used to correct the glucose concentration and the like. In other words, the accuracy of various types of corrections can be improved.

Working Example 20

Sensor chips were prepared to have the configuration illustrated in FIG. 9 and FIG. 10 in that the surface area of the portion 31 (working electrode) of the electrode 11 is 0.12 mm$^2$, the surface area of the portion 32 (counter electrode) of the electrode 12 of the sensor chip is 0.48 mm$^2$, and the inter-electrode distance is 100 µm. A blood sample with a Hct value of 45% was prepared.

Immediately after the distal end of the sensor chip gripped in the fingers for 5 seconds is mounted onto the measuring device, and immediately after the distal end of the sensor chip not gripped in the fingers is mounted onto the measuring device, the blood sample above is introduced in a 24° C. environment. Thereafter, a voltage of 2.15V was applied between the electrodes (temperature electrodes), and the respective response currents were measured.

Figure 43:
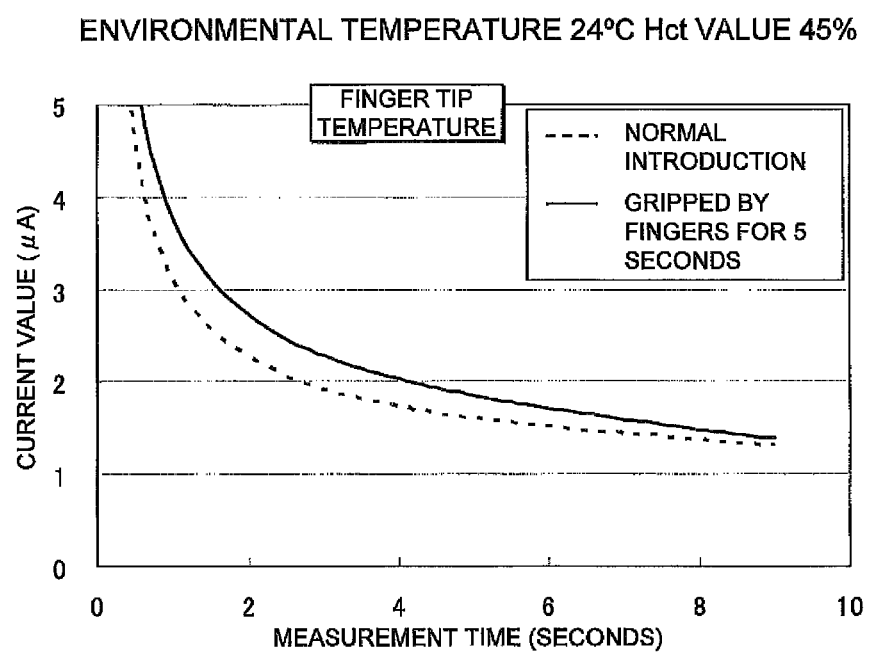
FIG. 43 is a graph illustrating a response current value when a distal end portion of the sensor chip is held between the fingers and not held between the fingers in an environment of 24° C. according to Working Example 20.

The measurement results are illustrated in the graph in FIG. 43. The solid line in FIG. 43 illustrates the response current when the distal end of the sensor chip is gripped in the fingers for 5 seconds in a 24° C. environment. The solid line in FIG. 43 illustrates the response current when the distal end of the sensor chip is not gripped in the fingers for 5 seconds in a 24° C. environment (hereinafter referred to as "normal introduction").

According to Working Example 20, an error in the finger tip temperature as illustrated in FIG. 43 can be comprehended.

The sensor chip according to the present invention is provided with a temperature electrode that is disposed to make contact with the blood sample, and that measures the temperature of the blood sample. Therefore, a temperature for the blood sample that takes into consideration finger-tip temperature can be obtained, and this value can be used to correct the glucose concentration and the like. In other words, the accuracy of various types of corrections can be improved.

Working Example 21

Sensor chips as described in Working Example 10 were prepared as illustrated in FIG. 2 and FIG. 3 in that the surface area of the portion 31 (working electrode) of the electrode 11 is 0.30 mm$^2$, the surface area of the portion 32 (counter electrode) of the electrode 12 of the sensor chip is 0.48 mm$^2$, and the inter-electrode distance is 100 µm. Blood samples with a glucose concentration of 209 mg/dL, Hct values of 25%, 45%, and 65% were prepared at a temperature of 22° C.

Figure 44:
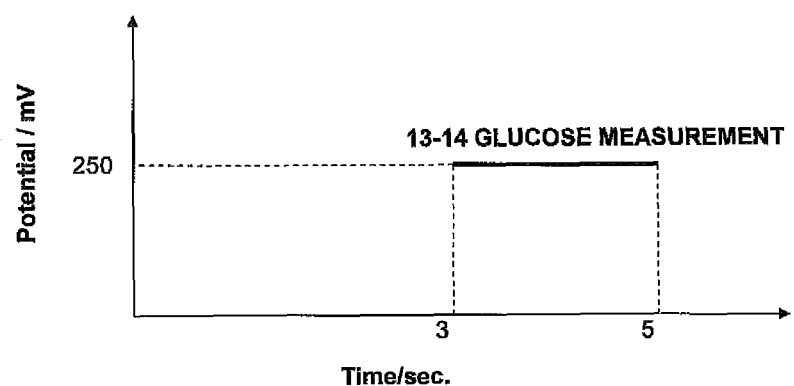
FIG. 44 illustrates a measurement sequence in Working Example 21.
Figure 44:
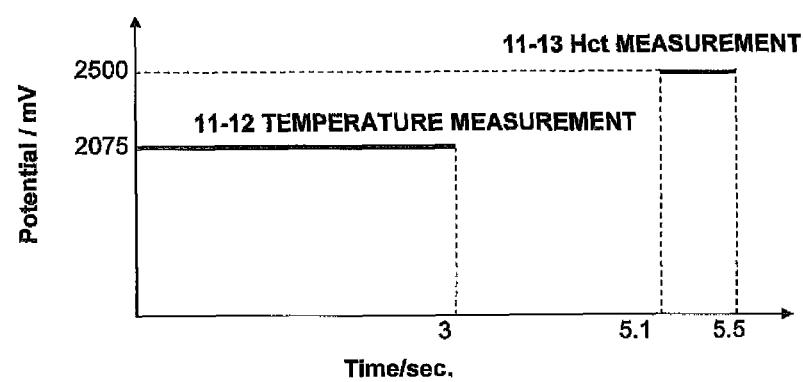

Next, after introduction of the blood samples into the capillary of the sensor chips as described above, a predetermined voltage was applied between predetermined electrodes in the order illustrated in FIG. 44. In other words, from 0 seconds to 3.0 seconds, a voltage of 2075 mV is applied to electrode 11 and electrode 12 (electrodes 11-12 in FIG. 44). Then from 3.0 seconds to 5.0 seconds, a voltage of 250 mV is applied to electrode 13 and electrode 14 (electrodes 13-14 in FIG. 44). Then from 5.1 seconds to 5.5 seconds, a voltage of 2500 mV is applied to electrode 11 and electrode 13 (electrodes 11-13 in FIG. 44). The respective response currents were measured.

Figure 45:
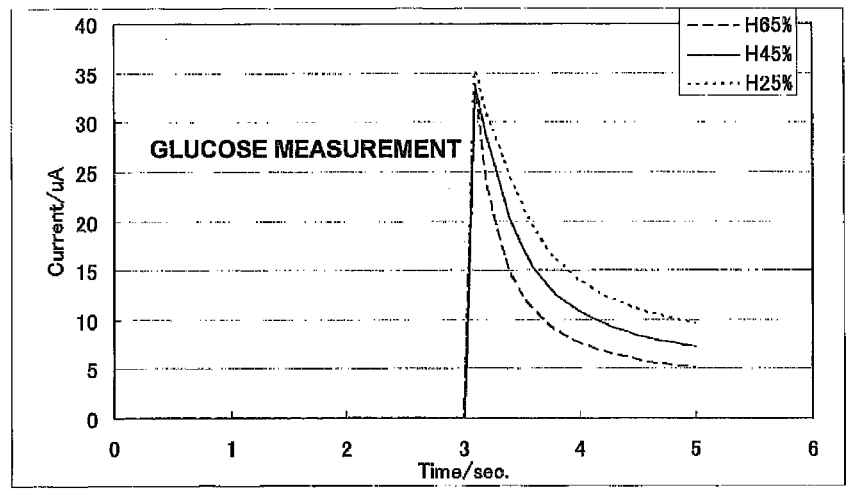
FIG. 45(a) is a graph illustrating a response current value for glucose measured in Working Example 21.
FIG. 45(b) is a graph illustrating a response current value for temperature and Hct measured in Working Example 21.
Figure 45:
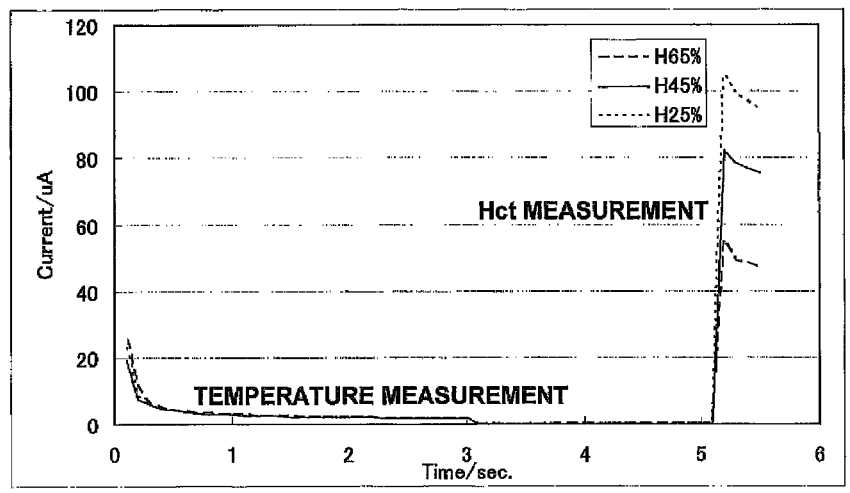
Figure 46:
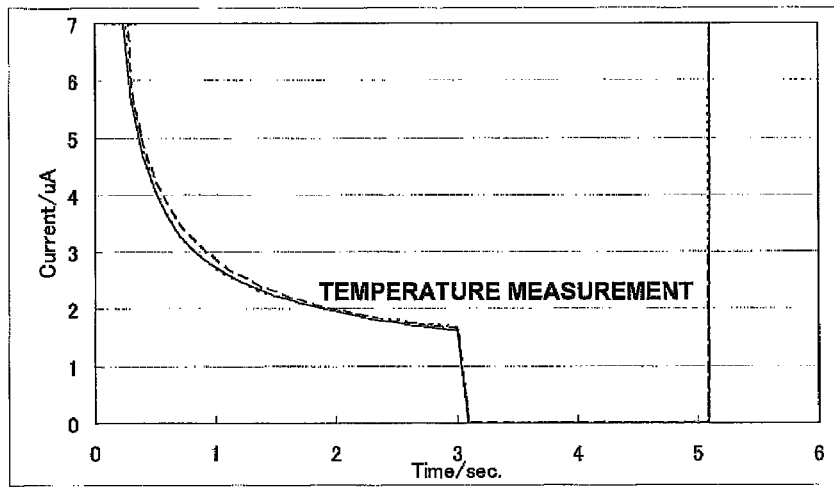
FIG. 46(a) is a graph illustrating a response current value for temperature measurement in Working Example 21.
Figure 46:
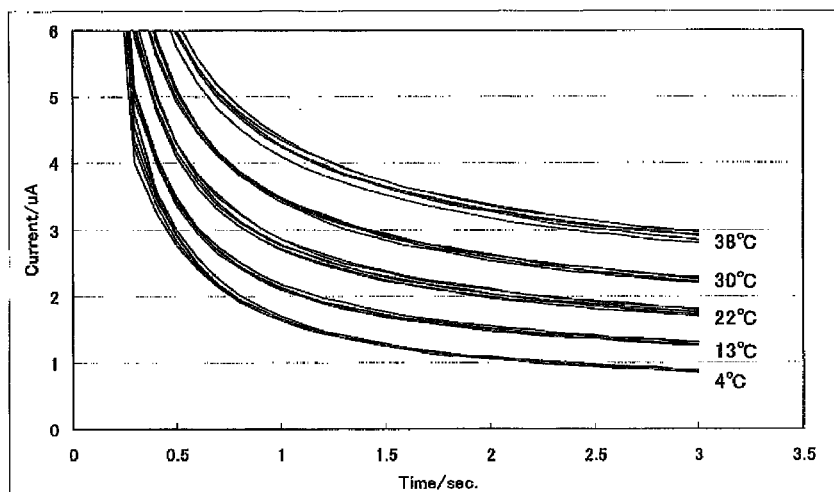

The measurement results are illustrated by the graph in FIG. 45(a) and FIG. 45(b). These graphs illustrate that a response current value according to the hematocrit value can be obtained when using glucose or Hct (hematocrit) as a measurement target. Furthermore as illustrated in FIG. 46(a), a response current value can be obtained in relation to a predetermined temperature as illustrated in FIG. 46(b) in relation to temperature.

According to Working Example 21, it is shown that measurement in sequence is possible in relation to respective features such as glucose, temperature or Hct.

The measurement sequence of glucose, temperature and Hct is not fixed to the sequence above, and may be executed in an arbitrary sequence. For example, the sequence of temperature, Hct and glucose is possible.

Figure 47:
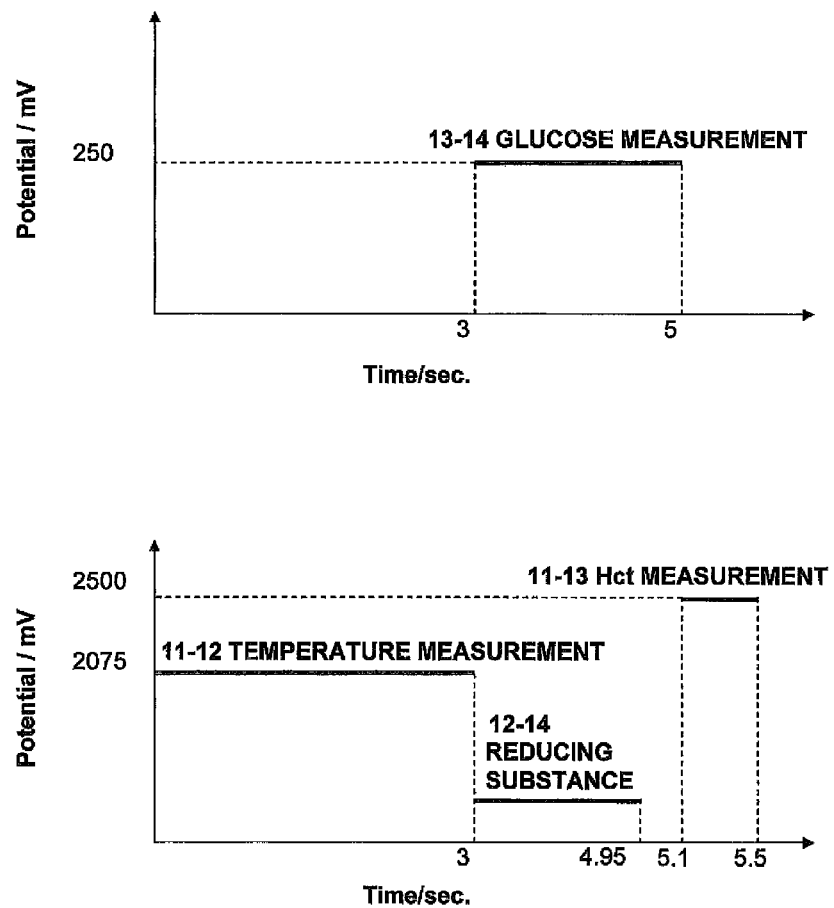
FIG. 47 illustrates another measurement sequence in Working Example 21.

As illustrated in FIG. 47, measurement is possible in relation to features including glucose, temperature, Hct and a reducing substance. In other words, as illustrated in FIG. 47, a voltage may be applied from 0 seconds to 3.0 seconds to electrode 11 and electrode 12 (electrodes 11-12 in FIG. 47), from 3.0 seconds to 4.95 seconds to electrode 12 and electrode 14 (electrodes 12-14 in FIG. 47), then substantially at the same time, from (3 seconds to 5.0 seconds), to electrode 13 and electrode 14 (electrodes 13-14 in FIG. 47), and from 5.1 seconds to 5.5 seconds to electrode 11 and electrode 13 (electrodes 11-13 in FIG. 47). This configuration also obtains a response current that corresponds to the respective conditions.

When measuring two or more features at the same time, care is required to avoid mixing combinations of the working electrode and the counter electrode. For example, when measuring glucose at the same time as temperature, it is preferred to measure the response current of the glucose measurement with electrode 13 and electrode 14 (electrodes 13-14 in FIG. 47), and the response current of the temperature measurement with electrode 11 and electrode 12 (electrodes 11-12 in FIG. 47). When the glucose response current flows between electrodes 13-12 or the temperature response current flows between electrodes 11-14, the desired response current cannot be obtained. As a result, when measuring two or more features at the same time, it is important to select suitable combinations of electrodes for application of voltage, suitable application voltage and application time in order to avoid the mixing as described above.

Modified Example 1

As illustrated in FIG. 6(a), in another embodiment, the step of determining the analyte concentration in the blood sample in step S4 (concentration determination step) was explained with reference to an example including step S101 to step S106. However the invention is not limited in this regard.

Figure 48:
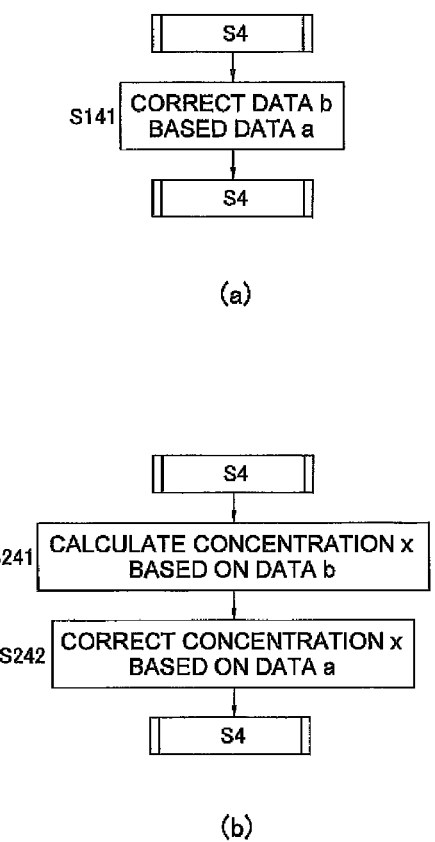
FIG. 48(a) and FIG. 48(b) is a flowchart illustrates a measurement method for analyte concentration in a blood sample in a biosensor system according to a first modified example according to the present invention.
Figure 50:
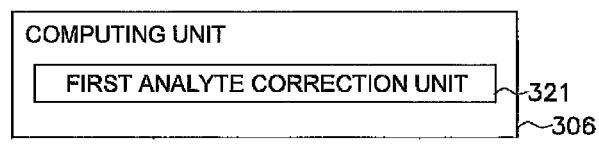
FIG. 50(a) and FIG. 50(b) is a circuit diagram for a biosensor system according to the first modified example according to the present invention.
Figure 50:
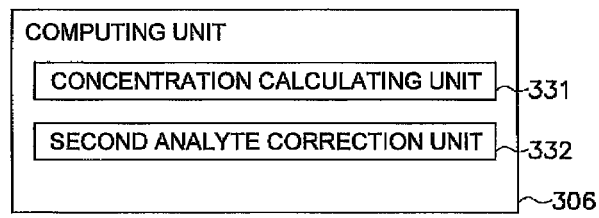

For example, as illustrated in FIG. 48(a), the concentration determination step S4 may include a step 141 for correcting the data b based on the data a. The computing unit (concentration determination unit) 306 in the biosensor system 100 (refer to FIG. 4) includes a first analyte correcting unit 321 configured to correct the data b based on the data a as illustrated in FIG. 50(a).

Furthermore, as illustrated in FIG. 48(b), the concentration determination step S4 may include a step S241 for calculating of the concentration x of the analyte in the blood sample based on the data b and a step S242 for correcting the concentration x based on the data a. The computing unit (concentration determination unit) 306 in the biosensor system 100 (refer to FIG. 4) includes a concentration calculating unit 331 configured to calculate a concentration x of an analyte in the blood sample based on data b, and a second analyte correcting unit 332 configured to correct a concentration x based on the data a as illustrated in FIG. 50(b).

Figure 49:
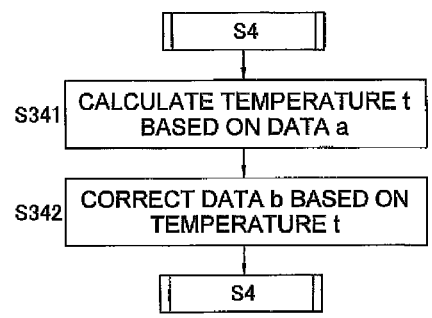
FIG. 49(a) and FIG. 49(b) is a flowchart illustrates a measurement method for analyte concentration in a blood sample in a biosensor system according to the first modified example according to the present invention.
Figure 49:
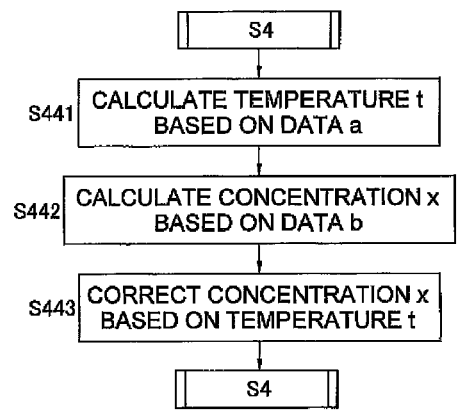
Figure 51:
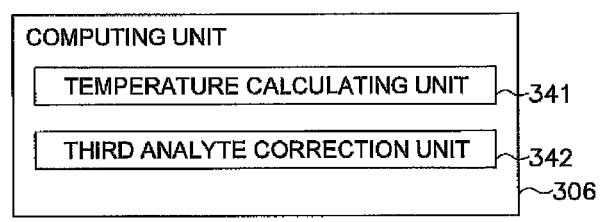
FIG. 51(a) and FIG. 51(b) is a circuit diagram for a biosensor system according to the first modified example according to the present invention.
Figure 51:
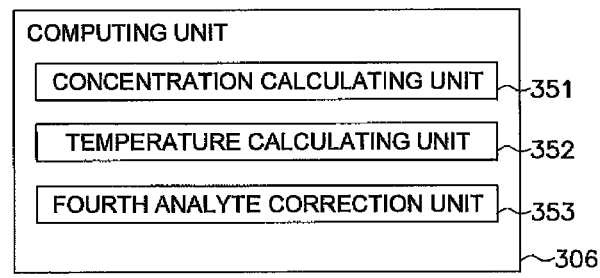

As illustrated in FIG. 49(a), the concentration determination step S4 may include a step S341 for calculating the temperature t of the blood sample based on the data a, and a step S342 for correcting the data b based on the temperature t. The computing unit (concentration determination unit) 306 in the biosensor system 100 (refer to FIG. 4) includes a temperature calculating unit 341 configured to calculate a temperature t of the blood sample based on data a, and a third analyte correcting unit 342 configured to correct the data b based on the temperature t as illustrated in FIG. 51(a).

As illustrated in FIG. 49(b), the concentration determination step S4 may include a step S441 for calculating the temperature t of the blood sample based on the data a, and a step S442 for calculating the concentration x of the analyte in the blood sample based on the data b. The computing unit (concentration determination unit) 306 in the biosensor system 100 (refer to FIG. 4) includes a temperature calculating unit 351 configured to calculate a temperature t of the blood sample based on data a, a concentration calculating unit 352 configured to calculate a concentration x of the analyte in the blood sample based on the data b, and a fourth analyte correcting unit 353 configured to correct the concentration x based on the temperature t as illustrated in FIG. 51(b).

Modified Example 2

Figure 52:
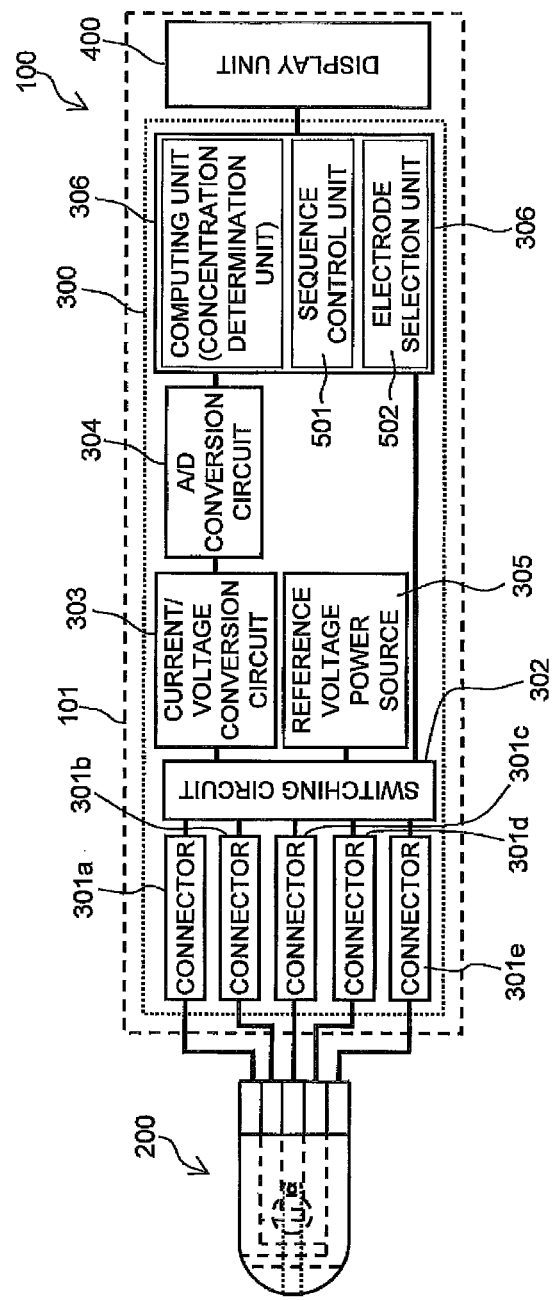
FIG. 52 is a circuit diagram for a biosensor system according to a second modified example according to the present invention.

The control circuit 300 in the above embodiment as illustrated in FIG. 52 may be further provided with a sequence control unit 501 and an electrode selection unit 502.

The sequence control unit 501 may control the control circuit 300 to simultaneously measure at least two features when measuring temperature, glucose, hematocrit, or a reducing substance. Furthermore the sequence control unit 501 may control the control circuit 300 to perform independent measurements when measuring temperature, glucose, hematocrit, or a reducing substance. The sequence of measuring these respective features is arbitrary. The sequence control unit 501 may control the control circuit 300 to perform independent measurements in the sequence of temperature, glucose and a reducing substance, and hematocrit when measuring temperature, glucose, hematocrit, or a reducing substance.

The electrode selection unit 502 may control the control circuit 300 to perform measurements through independent electrodes when measuring temperature, glucose, hematocrit, or a reducing substance.

During measurement of an analyte in a blood sample, the present invention suppresses the production of a measurement error caused by temperature when executing measurements, and therefore has useful value in broad technical areas that require high measurement accuracy.

REFERENCE NUMBERS 11, 12, 13, 14, 15 ELECTRODE (VOLTAGE APPLICATION PORTION)
16 DISCHARGE PORT
17 BLOOD SAMPLE INTRODUCTION PORT
20 REACTION REAGENT LAYER
31 PORTION OF ELECTRODE 11 FACING CAPILLARY
32 PORTION OF ELECTRODE 12 FACING CAPILLARY
33 PORTION OF ELECTRODE 13 FACING CAPILLARY
34 PORTION OF ELECTRODE 14 FACING CAPILLARY
35 PORTION OF ELECTRODE 15 FACING CAPILLARY
40 CAPILLARY
41 MEASURING UNIT A (TEMPERATURE MEASURING UNIT)
42 MEASURING UNIT B (ANALYTE MEASURING UNIT)
100 BIOSENSOR SYSTEM
101 MEASURING DEVICE
102 MOUNTING PORT
103 DISPLAY UNIT
200 SENSOR CHIP
201 INSULATING PLATE
202 SPACER
203 COVER
204 NOTCH
210 SENSOR CHIP
300 CONTROL CIRCUIT
301a, 301b, 301c, 301d, 301e CONNECTOR
302 SWITCHING CIRCUIT
303 CURRENT/VOLTAGE CONVERSION CIRCUIT
304 ANALOG/DIGITAL (A/D) CONVERSION CIRCUIT
305 REFERENCE VOLTAGE POWER SOURCE
306 COMPUTING UNIT (CONCENTRATION DETERMINATION UNIT)
307 TEMPERATURE MEASURING UNIT
308 COMPUTING UNIT
309 CONCENTRATION CALCULATING UNIT
310 TEMPERATURE CALCULATING UNIT
311 CONCENTRATION CALCULATING UNIT
312 ENVIRONMENTAL TEMPERATURE MEASURING UNIT
313 COMPARISON UNIT
314 CORRECTION UNIT
315 ENVIRONMENTAL TEMPERATURE MEASURING UNIT
321 FIRST ANALYTE CORRECTION UNIT
331 CONCENTRATION CALCULATING UNIT
332 SECOND ANALYTE CORRECTION UNIT
341 TEMPERATURE CALCULATING UNIT
342 THIRD ANALYTE CORRECTION UNIT
351 TEMPERATURE CALCULATING UNIT
352 CONCENTRATION CALCULATING UNIT
353 FOURTH ANALYTE CORRECTION UNIT
400 DISPLAY UNIT
501 SEQUENCE CONTROL UNIT
502 ELECTRODE SELECTION UNIT
S STEP

The invention claimed is:

1. A method for measuring a concentration of an analyte in a blood sample using a sensor chip, the sensor chip including a capillary and a pair of electrodes, the method including:
   acquiring data a related to a temperature of the blood sample, based on a dimension of a current flowing in the blood sample by applying a first voltage to the pair of electrodes in contact with the blood sample, the first voltage being set so as to reduce an effect of hematocrit on a temperature measurement result;
   acquiring data b related to the concentration of the analyte, based on a dimension of a current flowing in the blood sample by applying a second voltage that is equal to or less than the first voltage, utilizing a reaction mediated by an oxidoreductase that uses the analyte in the blood sample as a substrate; and
   measuring a concentration that determines the analyte concentration in the blood sample based on the data a and the data b, wherein
   the first voltage is between 1.0V and 3.0V, and the second voltage is between 0.05V and 1.0V.

2. The method according to claim 1, further includes correcting the data b based on the data a.

3. The method according to claim 1, further includes:
   calculating a concentration x of the analyte in the blood sample based on the data b; and
   correcting the concentration x based on the data a.

4. The method according to claim 1, further includes:
   calculating a temperature t of the blood sample based on the data a; and
   correcting the data b based on the temperature t.

5. The method according to claim 1, further includes:
   calculating a temperature t of the blood sample based on the data a;
   calculating a concentration x of the analyte in the blood sample based on the data b; and
   correcting the concentration x based on the temperature t.

6. The method according to claim 1, wherein the data a is acquired before the data b is acquired.

7. A method for measuring a concentration of an analyte in a blood sample using a sensor chip, the sensor chip including a capillary and a pair of electrodes, the method including:
   acquiring data a related to a temperature of the blood sample, based on a dimension of a current flowing in the blood sample by applying a first voltage to the pair of electrodes in contact with the blood sample, the first voltage being set so as to reduce an effect of hematocrit on a temperature measurement result;
   acquiring data b related to the concentration of the analyte, based on a dimension of a current flowing in the blood sample by applying a second voltage that is equal to or less than the first voltage, utilizing a reaction mediated by an oxidoreductase that uses the analyte in the blood sample as a substrate; and
   measuring a concentration that determines the analyte concentration in the blood sample based on the data a and the data b, wherein
   the data a related to the temperature of the blood sample contains a temperature, and the data b related to the concentration of the analyte contains a glucose concentration.

8. The method according to claim 7, wherein
the data b related to the concentration of the analyte contains hematocrit,
the data a related to the temperature of the blood sample contains a temperature, and
the data b related to the concentration of the analyte further contains a glucose concentration.

9. The method according to claim 7, wherein
the data b related to the concentration of the analyte contains a concentration or an amount of a reducing substance,
the data a related to the temperature of the blood sample contains a temperature, and
the data b related to the concentration of the analyte further contains a glucose concentration.

10. The method according to claim 7, wherein
at least two features of the data contained in the data a and the data b are measured at the same time,
the data a related to the temperature of the blood sample contains a temperature, and
the data b related to the concentration of the analyte contains a glucose concentration.

11. The method according to claim 10, wherein
the data contained in the data a and the data contained in the data b are measured independently.

12. The method according to claim 7, wherein
the data contained in the data a and the data contained the data b are measured in order of temperature, glucose concentration, concentration or amount of a reducing substance, and hematocrit,
the data a related to the temperature of the blood sample contains a temperature, and
the data b related to the concentration of the analyte contains a glucose concentration.

13. The method according to claim 10, wherein
the data contained in the data a and the data contained in the data b are measured through independent electrodes.

* * * * *